US007803920B2

(12) United States Patent
Yamanaka

(10) Patent No.: US 7,803,920 B2
(45) Date of Patent: Sep. 28, 2010

(54) ECAT16 GENE EXPRESSED SPECIFICALLY IN ES CELLS AND UTILIZATION OF THE SAME

(75) Inventor: Shinya Yamanaka, 2-9-7-1401, Dougashiba, Tennoji-ku, Osaka-shi, Osaka 543-0033 (JP)

(73) Assignees: Shinya Yamanaka, Osaka-shi (JP); Dainippon Sumitomo Pharma Co., Ltd., Osaka-shi (JP)

( * ) Notice: Subject to any disclaimer, the term of this patent is extended or adjusted under 35 U.S.C. 154(b) by 278 days.

(21) Appl. No.: 11/576,331

(22) PCT Filed: Sep. 27, 2005

(86) PCT No.: PCT/JP2005/017689

§ 371 (c)(1), (2), (4) Date: May 2, 2007

(87) PCT Pub. No.: WO2006/035741

PCT Pub. Date: Apr. 6, 2006

(65) Prior Publication Data

US 2008/0299548 A1 Dec. 4, 2008

(30) Foreign Application Priority Data

Sep. 29, 2004 (JP) ............................ 2004-282864

(51) Int. Cl.
*C07H 21/02* (2006.01)

(52) U.S. Cl. .................................................... 536/23.1

(58) Field of Classification Search ................. 435/23.1
See application file for complete search history.

(56) References Cited

U.S. PATENT DOCUMENTS

| | | | |
|---|---|---|---|
| 6,146,888 | A | 11/2000 | Smith et al. |
| 2002/0009786 | A1 | 1/2002 | Tang et al. |
| 2003/0017480 | A1 | 1/2003 | Ota et al. |
| 2004/0137460 | A1 | 7/2004 | Yamanaka et al. |

FOREIGN PATENT DOCUMENTS

| | | | |
|---|---|---|---|
| EP | 1 403 366 | A1 | 3/2004 |
| JP | 2005-110565 | A | 4/2005 |
| WO | WO 0166752 | A2 * | 9/2001 |
| WO | WO 02/097090 | A1 | 12/2002 |
| WO | WO 03/029271 | A2 | 4/2003 |
| WO | WO 2004/067744 | A1 | 8/2004 |
| WO | WO 2005/035562 | A1 | 4/2005 |
| WO | WO 2005/080598 | A1 | 9/2005 |

OTHER PUBLICATIONS

Bortvin et al. Development, 130: 1673-1680, 2003.*

Takahashi et al. Biochem. Society Transactions, 33(6): 1522-1525, 2005.*

Imamura et al., *BMC Developmental Biology*, 6(1): 34 (Jul. 21, 2006).

Wang et al., "*Mus musculus* ring finger protein 17 (Rnf17) mRNA, complete cds.," Database EMBL, EBI accession No. EMBL: AF285585 (Apr. 12, 2001).

Wang et al., "*Homo sapiens* ring finger protein 17 long isoform (RNF17) mRNA, complete cds.," Database EMBL, EBI accession No. EMBL: AF285602 (Apr. 12, 2001).

Yoshizaki et al., *Neuroscience Letters*, 363: 33-37 (2004).

Bortvin et al., *Development*, 130: 1673-1680 (2003).

Collins et al., *Proc. Natl. Acad. Sci. USA*, 99(26): 16899-16903 (Dec. 24, 2002).

Gerhard et al., *Genome Research*, 14: 2121-2127 (2004).

Kawai et al., *Nature*, 409: 685-690 (Feb. 8, 2001).

Mitsui et al., *Cell*, 113: 631-642 (May 30, 2003).

Okazaki et al., *Nature*, 420: 563-573 (Dec. 5, 2002).

Ota et al., *Nature Genetics*, 36(1): 40-45 (Jan. 2004).

Takahashi et al., *Nature*, 423: 541-545 (May 29, 2003).

Takeda et al., *Nucleic Acid Research*, 20(17): 4613-4620 (1992).

Yamanaka et al., *Experimental Medicine*, 21(15): 2109-2112 (2003).

Amano et al., *The 27th Annual Meeting of the Molecular Biology Society of Japan*, Kobe Port Island, Kobe, Japan, p. 760, 2PB-238 (Dec. 8-12, 2004).

Tokuzawa et al., *The 27th Annual Meeting of the Molecular Biology Society of Japan*, Kobe Port Island, Kobe, Japan, p. 760, 2PB-235 (Dec. 8-12, 2004).

* cited by examiner

*Primary Examiner*—Thaian N Ton
(74) *Attorney, Agent, or Firm*—Leydig, Voit & Mayer, Ltd.

(57) ABSTRACT

The present invention relates to an ES cell detection marker containing a polynucleotide derived from any one of ECAT15-1 gene, ECAT15-2 gene, ECAT16 gene, Rnf17 gene and LOC380905(TDRD4) gene.

3 Claims, 3 Drawing Sheets

ECAT16 GENE EXPRESSED SPECIFICALLY IN ES CELLS AND UTILIZATION OF THE SAME

INCORPORATION-BY-REFERENCE OF MATERIAL SUBMITTED ON COMPACT DISC

Incorporated by reference in its entirety herein is a computer-readable nucleotide/amino acid sequence listing submitted concurrently herewith and identified as follows: 169,030 bytes ASCII (Text) file named "701403SequenceListing.txt," created Mar. 29, 2007.

TECHNICAL FIELD

The present invention relates to a gene with ES cell (embryonic stem cell)-specific expression and utilization thereof.

BACKGROUND ART

Embryonic stem cells (ES cells) are stem cells established from an inner cell mass of mammalian blastocyst, and can be infinitely grown while maintaining their potential for differentiating into all types of cells (pluripotency). ES cell was first established in mouse in 1981, and gave rise to a milestone technique of gene function analysis using knockout mouse. Moreover, ever since establishment of human ES cell was reported in 1998, application to regenerative medicine has been highly expected. That is, functional recovery is designed by transplanting myocardial cells or nerve cells differentiated from the ES cell into patients with cardiac infarction or neurodegenerative disease.

While the cell transplantation therapy as represented by bone marrow transplantation in leukemia has already been put to practice, two problems of ensured supply of sufficient cells for transplantation and suppression of rejection. Using ES cell that divides semipermanently, the problem of ensured supply of sufficient cells can be solved altogether. Moreover, by combining the somatic cell clone technique, the rejection reaction can also be overcome. When ES cell is established from a clone embryo prepared from the somatic cell of the patient and used for transplantation, rejection cannot occur since the cell contains the same genes as those of the patient. Therefore, ES cell has a potential of solving both the two problems associated with the cell transplantation therapy.

Although ES cell has such a huge potential, since establishment and maintenance of human ES cell is difficult as compared to mouse ES cell, the development of certain establishment technique and culture technique is necessary. To establish a human ES cell, an embryo needs to be sacrificed. When combined with the somatic cell clone technique, it leads to the easy preparation of a human clone. To solve such an ethical problem, the development of a technique to directly produce a pluripotent ES-like cell from a somatic cell without using an embryo has been desired.

In such technique development, a gene specifically expressed in pluripotent cells such as ES cells ((ES cell associated transcript gene, hereinafter ECAT gene) plays an important role.

The ECAT gene becomes a marker to determine whether a cell is an ES cell. In addition, by combining the regulatory region that causes ES cell specific expression of ECAT gene and a drug resistant gene, an ES cell can be efficiently selected from a mixed culture of many kinds of cells (see patent reference 1). Moreover, by inducing expression of an ECAT gene in a somatic cell, conversion to an ES-like cell may be promoted.

A reported ECAT gene is the transcription factor Oct3 (also called Oct4 or POU5f1; hereinafter referred to as Oct3/4) gene. Although a similar gene has been reported in humans (hOct3/4 gene; see non-patent reference 1), there is no report of demonstrating the ES-cell-specific expression of the hOct-3/4 gene.

In recent years, in search of an unknown factor that positively maintains pluripotency in both ES cell and inner cell mass, our group has found nine genes specifically expressed in ES cells on the basis of the analysis of an EST database by Digital Differential Display, and designated them as ECAT1 gene-ECAT9 gene (see patent reference 1). Of these, ECAT4 is a factor also called Nanog, and has been shown to be an essential factor for the maintenance of the totipotency (pluripotency) of ES cells (see non-patent reference 2). ECAT5 is a factor also called ERas, and has been shown to promote the growth of ES cells (see non-patent reference 3).

In the aforementioned analysis, Oct3/4, UTF1, REX1 and the like reported to show experimental pluripotent cell-specific expression have additionally been identified, and therefore, the analysis has been established to be an extremely effective screening method.

patent reference 1: U.S. Pat. No. 6,146,888 patent reference 2: WO 02/097090 non-patent reference 1: Takeda et al., Nucleic Acids Research, 20: 4613-4620 (1992)

non-patent reference 2: Mitsui, K., et al., Cell, 113: 631-642 (2003)

non-patent reference 3: Takahashi, K., et al., Nature, 423: 541-545 (2003)

DISCLOSURE OF THE INVENTION

Problems to be Solved by the Invention

The present invention aims at providing a novel ECAT gene. More particularly, the present invention aims at providing a detection method of an ES cell, a screening method for a somatic cell nuclear reprogramming substance, or a screening method for a substance for the maintenance of ES cell utilizing a novel ECAT gene (ECAT15-1 gene, ECAT15-2 gene, ECAT16 gene, Rnf17 gene or LOC380905(TDRD4) gene), and the like.

Means of Solving the Problems

The present inventors are working on the search for a new ECAT gene from the aspects of basic study of ES cell and regenerative medicine, application of ES cell to cell transplantation and the like.

For identification of a novel ECAT gene, the present inventors analyzed the EST database by Digital Differential Display to search for a candidate gene. Of the candidate genes, they took note of ECAT15-1 gene containing a SAP motif which is a DNA binding domain, and Rnf17 gene suggested to be bound with the oncogene myc, and conducted intensive studies. As a result, it has been clarified that the following five kinds of genes (1)-(5):

(1) ECAT15-1 gene (SEQ ID NOs: 1-4), (2) ECAT15-2 gene (SEQ ID NOs: 5-8), (3) ECAT16 gene (SEQ ID NOs: 17-18 and SEQ ID NOs: 33-34), (4) Rnf17 gene (SEQ ID NOs: 9-12), (5) LOC380905 gene (SEQ IDs NO: 13-16), (the above-mentioned SEQ ID NOs include the corresponding amino acid sequences), particularly ECAT15-1 gene, ECAT15-2 gene and ECAT16 gene, are ECAT genes specifically expressed in ES cell, and are marker genes characterizing the ES cell.

Since the novel ECAT genes of the present invention are all specifically expressed in ES cells, these genes or the protein encoded by the genes are effectively used for the detection of an ES cell, screening of a somatic cell nuclear reprogramming substance, screening for a substance for the maintenance of ES cell and the like.

The present invention was completed based on these findings.

Accordingly, the present invention provides the following:

(1) an ES cell detection marker comprising a polynucleotide derived from any one of ECAT15-1 gene, ECAT15-2 gene, ECAT16 gene, Rnf17 gene and LOC380905(TDRD4) gene, (2) the marker of the aforementioned (1), wherein the ECAT15-1 gene is a gene containing a base sequence described in SEQ ID NO: 1 or 3, (3) the marker of the aforementioned (1), wherein the ECAT15-2 gene is a gene containing a base sequence described in SEQ ID NO: 5 or 7, (4) the marker of the aforementioned (1), wherein the ECAT16 gene is a gene containing a base sequence described in SEQ ID NO: 17 or 33, (5) the marker of the aforementioned (1), wherein the Rnf17 gene is a gene containing a base sequence described in SEQ ID NO: 9 or 11, (6) the marker of the aforementioned (1), wherein the LOC380905(TDRD4) gene is a gene containing a base sequence described in SEQ ID NO: 13 or 15, (7) the marker of any one of the aforementioned (1)-(6), which comprises a polynucleotide containing at least 15 contiguous bases and/or a polynucleotide complementary to the polynucleotide, (8) an ES cell detection marker comprising a polynucleotide containing at least 15 contiguous bases in any one of the base sequence described in SEQ ID NO: 1, 3, 5, 7, 9, 11, 13, 15, 17 or 33, and/or a polynucleotide complementary to the polynucleotide, (9) the marker of any one of the aforementioned (1)-(8), which is used as a probe or primer for the detection of an ES cell,

(10) an ES cell detection marker comprising an antibody recognizing any one of ECAT15-1, ECAT15-2, ECAT16, Rnf17 and LOC380905(TDRD4),

(11) the marker of the aforementioned (10), wherein the ECAT15-1 is a protein containing the amino acid sequence described in SEQ ID NO: 2 or 4,

(12) the marker of the aforementioned (10), wherein the ECAT15-2 is a protein containing the amino acid sequence described in SEQ ID NO: 6 or 8,

(13) the marker of the aforementioned (10), wherein the ECAT16 is a protein containing the amino acid sequence described in SEQ ID NO: 18 or 34,

(14) the marker of the aforementioned (10), wherein the Rnf17 is a protein containing the amino acid sequence described in SEQ ID NO: 10 or 12,

(15) the marker of the aforementioned (10), wherein the LOC380905(TDRD4) is a protein containing the amino acid sequence described in SEQ ID NO: 14 or 16,

(16) a method for detecting an ES cell, which comprises the following steps (a), (b) and (c):

(a) a step for binding RNA derived from a test cell or a complementary polynucleotide transcribed therefrom, and the marker of any one of the aforementioned (1)-(9), (b) a step for measuring the RNA derived from a test cell or the complementary polynucleotide transcribed therefrom, which has been bound with the marker, with the above-mentioned marker as an index, (c) a step for determining whether or not the test cell is an ES cell, based on the measurement results of the above-mentioned (b),

(17) a method for detecting an ES cell, which comprises the following steps (a), (b) and (c):

(a) a step for binding a protein derived from a test cell and the marker of any one of the aforementioned (10)-(15), (b) a step for measuring the protein derived from a test cell, which has been bound with the marker, with the above-mentioned marker as an index, (c) a step for determining whether or not the test cell is an ES cell, based on the measurement results of the above-mentioned (b),

(18) a screening method for a somatic cell nuclear reprogramming substance, which comprises the following steps (a) and (b):

(a) a step for bringing into contact with each other a somatic cell comprising a gene wherein a marker gene is present at a position permitting expression control by the expression control region of the ECAT 15-gene, ECAT15-2 gene, ECAT16 gene, Rnf17 gene or LOC380905(TDRD4) gene and a test substance, (b) a step following the aforementioned step (a), for determining the presence or absence of the emergence of cells expressing the marker gene, and selecting a test substance allowing the emergence of the cells as a somatic cell nuclear reprogramming substance candidate,

(19) the screening method of the aforementioned (18), wherein the marker gene is a drug resistant gene, a fluorescent protein gene, a luminescent enzyme gene, a chromogenic enzyme gene or a gene comprising a combination thereof,

(20) the screening method of the aforementioned (18) or (19), which comprises the following steps (a) and (b):

(a) a step for bringing into contact with each other a somatic cell comprising a gene resulting from knocking in a gene comprising a drug resistant gene to the ECAT15-1 gene, ECAT15-2 gene, ECAT16 gene, Rnf17 gene or LOC380905 (TDRD4) gene and a test substance, (b) a step following the aforementioned step (a), for determining the presence or absence of surviving cells in a selection medium, and selecting a test substance allowing the emergence of the surviving cells as a somatic cell nuclear reprogramming substance candidate,

(21) a knock-in mouse comprising a gene resulting from knocking in a marker gene to ECAT15-1 gene, ECAT15-2 gene, ECAT16 gene, Rnf17 gene or LOC380905(TDRD4) gene,

(22) use of the knock-in mouse of the aforementioned (21) as a source of the somatic cell used in the screening method of any of the aforementioned (18) to (20),

(23) a somatic cell comprising a gene wherein a marker gene is present at a position permitting expression control by the expression control region of ECAT15-1 gene, ECAT15-2 gene, ECAT16 gene, Rnf17 gene or LOC380905(TDRD4) gene,

(24) the somatic cell of the aforementioned (23), which comprises a gene resulting from knocking in a marker gene to ECAT15-1 gene, ECAT15-2 gene, ECAT16 gene, Rnf17 gene or LOC380905(TDRD4) gene,

(25) a selection method for an ES-like cell, which comprises the following steps (a) and (b):

(a) a step for bringing into contact with each other a somatic cell comprising a gene wherein a marker gene is present at a position permitting expression control by the expression control region of the ECAT15-1 gene, ECAT15-2 gene, ECAT16 gene, Rnf17 gene or LOC380905(TDRD4) gene and a somatic cell nuclear reprogramming substance, (b) a step following the aforementioned step (a), for selecting a cell expressing the marker gene as an ES-like cell,

(26) the selection method of the aforementioned (25), which comprises the following steps (a) and (b):

(a) a step for bringing into contact with each other a somatic cell comprising a gene wherein a drug resistant gene is present at a position permitting expression control by the expression control region of the ECAT15-1 gene, ECAT15-2 gene, ECAT16 gene, Rnf17 gene or LOC380905(TDRD4) gene, and a somatic cell nuclear reprogramming substance, (b) a step following the aforementioned step (a), for selecting a surviving cell in a selection medium as an ES-like cell,

(27) use of the somatic cell of the aforementioned (23) or (24) for the screening method of any one of the aforementioned (18)-(20) or the selection method of any of the aforementioned (25)-(26),

(28) a screening method for a substance for the maintenance of undifferentiated state and pluripotency of ES cells, which comprises the following steps (a) and (b):

(a) a step for bringing an ES cell comprising a gene wherein a marker gene is present at a position permitting expression control by the expression control region of the ECAT15-1 gene, ECAT15-2 gene, ECAT16 gene, Rnf17 gene or LOC380905(TDRD4) gene into contact with a test substance in a medium not allowing the maintenance of undifferentiated state and pluripotency of ES cells, (b) a step following the aforementioned step (a), for determining the presence or absence of cells expressing the marker gene, and selecting a test substance allowing the occurrence of the cells as a candidate substance for the maintenance of undifferentiated state and pluripotency of ES cells,

(29) the screening method of the aforementioned (28), which comprises the following steps (a) and (b):

(a) a step for bringing an ES cell comprising a gene resulting from knocking in a gene comprising a drug resistant gene to the ECAT15-1 gene, ECAT15-2 gene, ECAT16 gene, Rnf17 gene or LOC380905(TDRD4) gene into contact with a test substance in a medium not allowing the maintenance of undifferentiated state and pluripotency of ES cells, (b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells,

(30) an ES cell comprising a gene wherein a marker gene is present at a position permitting expression control by the expression control region of the ECAT15-1 gene, ECAT15-2 gene, ECAT16 gene, Rnf17 gene or LOC380905(TDRD4) gene,

(31) the ES cell of the aforementioned (30), which comprises a gene resulting from knocking in a marker gene to the ECAT15-1 gene, ECAT15-2 gene, ECAT16 gene, Rnf17 gene or LOC380905(TDRD4) gene,

(32) use of the ES cell of the aforementioned (30) or (31) in the screening method described in (28) or (29) above,

(33) a conjugate of a protein containing any one of ECAT15-1, ECAT15-2, ECAT16, Rnf17 and LOC380905(TDRD4) and a substance that promotes uptake of the protein into a cell,

(34) the conjugate of the aforementioned (33), which is a fusion protein of a protein containing any one of ECAT15-1, ECAT15-2, ECAT16, Rnf17 and LOC380905(TDRD4) and a protein that promotes uptake of the protein into a cell,

(35) a polynucleotide containing a base sequence encoding the fusion protein of the aforementioned (34),

(36) an expression vector containing the polynucleotide of the aforementioned (35),

(37) a cell into which the expression vector of the aforementioned (36) has been introduced,

(38) an agent for maintaining the function of an ES cell, which comprises a protein containing any one of ECAT15-1, ECAT15-2, ECAT16, Rnf17 and LOC380905(TDRD4), or the conjugate of the aforementioned (33) or (34), as an active ingredient,

(39) an agent for maintaining the function of an ES cell, which comprises, as an active ingredient, a polynucleotide containing any one of the ECAT15-1 gene, ECAT15-2 gene, ECAT16 gene, Rnf17 gene and LOC380905(TDRD4) gene, or an expression vector containing the same,

(40) a polynucleotide of ECAT16 gene, which is any one of the following (a)-(d):

(a) a polynucleotide containing the base sequence described in SEQ ID NO: 17 or 33, (b) a polynucleotide containing a base sequence encoding the amino acid sequence described in SEQ ID NO: 18 or 34, (c) a polynucleotide having a homology of 70% or more with the polynucleotide of the aforementioned (a) or (b), and encoding a protein having the function of ECAT16, (d) a polynucleotide encoding a protein having the function of ECAT16, which hybridizes to the polynucleotide (complementary strand) of the aforementioned (a) or (b) under stringent conditions,

(41) an ECAT16 protein, which is any one of the following (a)-(c):

(a) a protein containing the amino acid sequence described in SEQ ID NO: 18 or 34, (b) a protein having a homology of 70% or more with the protein of the aforementioned (a), and having the function of ECAT16, (c) a protein containing an amino acid sequence of the aforementioned (a) wherein one or plural amino acids are substituted, deleted and/or added, and having the function of ECAT16,

(42) a polynucleotide having the base sequence described in SEQ ID NO: 1 or 5,

(43) a protein having the amino acid sequence described in SEQ ID NO: 2 or 6,

(44) an expression vector containing the polynucleotide of the aforementioned (40) or (42),

(45) a cell into which the expression vector of the aforementioned (44) has been introduced,

(46) a method for producing a recombinant protein, which comprises cultivating the cell of the aforementioned (45) under the conditions where the expression vector of the aforementioned (44) can be expressed,

(47) an antibody specifically binding with the protein of the aforementioned (41) or (43),

(48) a polynucleotide containing at least 15 contiguous bases which is specific to the polynucleotide of the aforementioned (40) or (42), and/or a polynucleotide complementary to the polynucleotide,

(49) a polypeptide containing at least 6 contiguous amino acids, which is specific to any of the proteins of the aforementioned (41) and (43),

(50) a genetically modified animal obtained by artificially inserting the polynucleotide of any of the aforementioned (40) and (42) into a chromosome, or knocking out either polynucleotide,

(51) an antisense nucleic acid or a short interfering RNA (siRNA) complementary to the polynucleotide of any of the aforementioned (40) and (42),

(52) a complex of ECAT15-1 and ECAT15-2,

(53) the agent for maintaining the function of an ES cell of the aforementioned (38), which comprises, as an active ingredient, the complex of the aforementioned (52), or a conjugate thereof and a substance promoting uptake of the complex into a cell, and

(54) the agent for maintaining the function of an ES cell of the aforementioned (39), which comprises the following (a) and (b) as an active ingredient:

(a) a polynucleotide containing ECAT15-1 gene or an expression vector containing same, (b) a polynucleotide containing ECAT15-2 gene or an expression vector containing same.

EFFECT OF THE INVENTION

Since the ECAT15-1 gene, ECAT15-2 gene, ECAT16 gene, Rnf17 gene and LOC380905(TDRD4) gene in the present invention are specifically expressed in an ES cell, these genes or proteins encoded by the genes can be effectively used for the detection of an ES cell, screening for a somatic cell nuclear reprogramming substance, screening for a ES cell maintaining substance and the like.

BEST MODE FOR EMBODYING THE INVENTION

Abbreviations for amino acids, (poly)peptides, (poly) nucleotides and the like used in the present description are based on the IUPAC-IUB rules [IUPAC-IUB Communication on Biological Nomenclature, Eur. J. Biochem., 138:9 (1984)], "Guideline for the Preparation of Descriptions etc. Including Base Sequences or Amino Acid Sequences" (edited by the Japan Patent Office), or abbreviations in common use in relevant fields.

The term "gene (ECAT15-1 gene, ECAT15-2 gene, ECAT16 gene, Rnf17 gene, LOC380905(TDRD4) gene)" as used herein sometimes refer not only to the cDNA (mRNA), but also to the genomic DNA, depending on the technical contents.

In the present specification, the "polynucleotide" is used to encompass any of RNA and DNA.

In the present specification, the "antibody" encompasses a polyclonal antibody, a monoclonal antibody, a chimeric antibody, a single chain antibody and a part of the above-mentioned antibody having antigen bindability such as a Fab fragment, a fragment generated by a Fab expression library and the like.

In the present specification, the "ECAT15-1 gene" refers to a mouse ECAT15-1 gene containing the base sequence described in SEQ ID NO: 1, a human ECAT15-1 gene containing the base sequence described in SEQ ID NO: 3, or a gene containing a base sequence similar to such base sequences.

In the present specification, the "ECAT15-2 gene" refers to a mouse ECAT15-2 gene containing the base sequence described in SEQ ID NO: 5, a human ECAT15-2 gene containing the base sequence described in SEQ ID NO: 7, or a gene containing a base sequence similar to such base sequences.

In the present specification, the "ECAT16 gene" refers to a mouse ECAT16 gene containing the base sequence described in SEQ ID NO: 17, a human ECAT16 gene containing the base sequence described in SEQ ID NO: 33, or a gene containing a base sequence similar to such base sequences.

In the present specification, the "Rnf17 gene" refers to a mouse Rnf17 gene containing the base sequence described in SEQ ID NO: 9, a human Rnf17 gene containing the base sequence described in SEQ ID NO: 11, or a gene containing a base sequence similar to such base sequences.

In the present specification, the "LOC380905(TDRD4) gene" refers to a gene called a LOC380905 gene or TDRD4 gene, specifically, a mouse LOC380905 gene containing the base sequence described in SEQ ID NO: 13, a human TDRD4 gene (human homologous gene of mouse LOC380905) containing the base sequence described in SEQ ID NO: 15, or a gene containing a base sequence similar to such base sequences.

The "gene comprising a similar base sequence" as used above refers to a gene comprising a base sequence resulting from the deletion, substitution or addition of one or more bases in any of the base sequences shown by the aforementioned sequence identification numbers and a gene comprising a base sequence having a high homology to any of the base sequences shown by the aforementioned sequence identification numbers can be mentioned.

"A gene comprising a base sequence having a high homology" as used herein refers to a gene comprising a base sequence having a homology of 70% or more, preferably 80% or more, more preferably 90% or more, and particularly preferably 95% or more, to the base sequence shown by any of the aforementioned sequence identification numbers can be mentioned. As other embodiment, a gene that hybridizes to the base sequences (complementary strand) shown by the aforementioned SEQ ID NOs. under stringent conditions can be mentioned. Stringent conditions as mentioned herein can be adjusted by changing the temperatures, salt concentrations and the like during the hybridization reaction and washing as appropriate, and are set according to desired homology; for example, hybridization conditions involving a salt concentration of 6×SSC and a temperature of 65° C. can be mentioned.

When such "gene comprising a similar base sequence (to each ECAT gene in the present invention)" is used as a marker, it only needs to characteristically detect an ES cell-specific expression of each ECAT gene. When it is used as the below-mentioned agent for maintaining the function of an ES cell, it only needs to have an ES cell function-maintaining activity similar to that of each ECAT gene.

In the present specification, the "ECAT15-1" refers to a mouse ECAT15-1 protein containing the amino acid sequence described in SEQ ID NO: 2, a human ECAT15-1 protein containing the amino acid sequence described in SEQ ID NO: 4, or a protein containing an amino acid sequence similar to such amino acid sequences.

In the present specification, the "ECAT15-2" refers to a mouse ECAT15-2 protein containing the amino acid sequence described in SEQ ID NO: 6, a human ECAT15-2 protein containing the amino acid sequence described in SEQ ID NO: 8, or a protein containing an amino acid sequence similar to such amino acid sequences.

In the present specification, the "ECAT16" refers to a mouse ECAT16 protein containing the amino acid sequence described in SEQ ID NO: 18, a human ECAT16 protein containing the amino acid sequence described in SEQ ID NO: 34, or a protein containing an amino acid sequence similar to such amino acid sequences.

In the present specification, the "Rnf17" refers to a mouse Rnf17 protein containing the amino acid sequence described in SEQ ID NO: 10, a human Rnf17 protein containing the amino acid sequence described in SEQ ID NO: 12, or a protein containing an amino acid sequence similar to such amino acid sequences.

In the present specification, the "LOC380905(TDRD4)" refers to a mouse LOC380905 protein containing the amino acid sequence described in SEQ ID NO: 14, a human TDRD4 protein (human homologous protein of mouse LOC380905) containing the amino acid sequence described in SEQ ID NO: 16, or a protein containing an amino acid sequence similar to such amino acid sequences.

In the aforementioned, the "protein comprising a similar amino acid sequence (to each ECAT gene in the present invention)" refers to a protein encoded by the aforementioned "gene comprising a similar base sequence (to each ECAT gene in the present invention). Specifically, a protein containing the amino acid sequence having a homology of 70% or more, preferably 80% or more, more preferably 90% or more, particularly preferably 95% or more, with the amino acid sequence shown by the aforementioned SEQ ID NO can be mentioned.

When such protein comprising a similar amino acid sequence (to each ECAT in the present invention) is used as an antigen for producing a marker (antibody), it only needs to characteristically have a similar antigenicity as each ECAT. When it is used as the below-mentioned agent for maintaining the function of an ES cell, it only needs to have an ES cell function-maintaining activity similar to that of each ECAT.

(1) ES Cell Detection Marker (1-1) Polynucleotide

Beginning with the finding that ECAT15-1 gene, ECAT15-2 gene, ECAT16 gene, Rnf17 gene and LOC380905 (TDRD4) gene (hereinafter sometimes to be referred to as the gene of the present invention) are specifically expressed in ES cell, the present invention is based on the finding that whether or not the test cell is an ES cell can be detected by detecting the presence or absence of expression of these genes and the level of expression, as mentioned above. Specifically the present invention provides an ES cell detection marker consisting of a polynucleotide specific to any one of these ECAT15-1 gene, ECAT15-2 gene, ECAT16 gene, Rnf17 gene and LOC380905(TDRD4) gene.

The "ES cell" includes an ES-like cell in addition to ES cell. The "ES-like cell" means a cell having ES cell properties, that is, a cell in undifferentiated state and having pluripotency.

Here, the "specific polynucleotide" refers to a polynucleotide having a length that permits distinguishing and specifying each of the aforementioned genes from other genes. The gene of the present invention includes genes (ECAT16 gene, Rnf17 gene and LOC380905(TDRD4) gene) having overlapping gene sequences. Since these genes are genes specifically expressed in an ES cell, there is no problem using a polynucleotide binding with two or more kinds of ECAT16 gene, Rnf17 gene and LOC380905(TDRD4) gene as a marker. Thus, the ECAT16 gene, Rnf17 gene and LOC380905 (TDRD4) gene are each to be excluded from the category of "other genes". Specifically, even if a polynucleotide recognizes two or more kinds of ECAT16 gene, Rnf17 gene and LOC380905(TDRD4) gene, it is included in the category of the aforementioned "specific polynucleotide" as long as it does not recognize other irrelevant gene.

In addition, interspecies differences (e.g., between human and mouse) regarding the same factor is to be excluded from the category of "other genes". To be specific, even if a polynucleotide recognizes ECAT15-1 genes from two or more species (e.g., mouse and human), ECAT15-2 genes from two or more species (e.g., mouse and human), ECAT16 genes from two or more species (e.g., mouse and human), Rnf17 genes from two or more species (e.g., mouse and human), or LOC380905(TDRD4) genes from two or more species (e.g., mouse and human), it is included in the category of the aforementioned "specific polynucleotide" as long as it does not recognize other irrelevant gene.

Concretely, the ES cell detection marker of the present invention can distinguish and specify one gene from other genes, when it contains 15 bases in general. Accordingly, specific examples of the marker of the present invention include an ES cell detection marker consisting of a polynucleotide containing at least 15 contiguous bases from the base sequences of the aforementioned ECAT15-1 gene, ECAT15-2 gene, ECAT16 gene, Rnf17 gene and LOC380905 (TDRD4) gene and/or a polynucleotide complementary thereto.

More specifically, the marker of the present invention includes an ES cell detection marker consisting of a polynucleotide containing at least 15 contiguous bases from the base sequence described in any of SEQ ID NOs: 1, 3, 5, 7, 9, 11, 13, 15, 17 and 33 and/or a polynucleotide complementary thereto.

Here, the complementary polynucleotide (complementary strand, reverse strand) refers to a polynucleotide in a complementary relationship in terms of bases, such as a relationship of A:T or G:C relative to the base, with a full-length sequence of a polynucleotide consisting of the base sequence of the aforementioned gene of the present invention, or a partial sequence having a base sequence of at least a contiguous 15 base length from said base sequence. However, this complementary strand is not limited to one forming a completely complementary sequence to the base sequence of the target sense strand, but may have a complementary relationship of the level permitting hybridization to the target sense strand under stringent conditions. Here, the stringent conditions can be determined based on the melting temperature (Tm) of nucleic acid binding a complex or a probe, as taught in Berger and Kimmel (1987, Guide to Molecular Cloning Techniques Methods in Enzymology, Vol. 152, Academic Press, San Diego Calif.). For example, as the washing conditions after hybridization, conditions of generally approximately "1×SSC, 0.1% SDS, 37° C." can be mentioned. It is preferable that the complementary strand remain hybridized to the target sense strand even after washing under such conditions. While the conditions are not particularly limited, more stringent hybridizing conditions include washing conditions of approximately "0.5×SSC, 0.1% SDS, 42° C.", still more stringent hybridizing conditions include washing conditions of approximately "0.1×SSC, 0.1% SDS, 65° C.". To be specific, as such complementary strand, a strand consisting of a base sequence in a completely complementary relationship with the base sequence of the target sense strand, and a strand consisting of a base sequence having a homology of at least 90%, preferably 95%, with said strand.

Here, the polynucleotide of the sense strand includes one having the base sequence of the gene of the present invention, or a partial sequence thereof, and further, a strand consisting of a base sequence in a complementary relationship with the base sequence of the above-mentioned complementary strand.

Furthermore, the above-mentioned polynucleotide of sense strand and the polynucleotide of complementary strand (reverse strand) may be used as a marker in the form of a single strand or a double strand. In addition, the aforementioned polynucleotide labeled for detection is also encompassed in the category of the polynucleotide of the present invention.

Concretely, the ES cell detection marker of the present invention may be a polynucleotide consisting of the base sequence (full-length sequence) of the gene of the present invention, or a polynucleotide consisting of a complementary sequence thereof.

It may be a polynucleotide consisting of a partial sequence of the above-mentioned full-length sequence or the complementary sequence thereof, as long as it selectively (specifically) recognizes the gene of the present invention or a polynucleotide derived from the gene. In this case, the partial sequence includes a polynucleotide having an at least 15 contiguous base length optionally selected from the base sequence of the above-mentioned full-length sequence or the complementary sequence.

The "selectively (specifically) recognizes" here refers to, for example, that the gene of the present invention or a polynucleotide derived therefrom can be specifically detected by the Northern blot method, and that the gene of the present invention or a polynucleotide derived therefrom can be specifically produced by the RT-PCR method. However, the expression is not limited thereto and may include any as long as those of ordinary skill in the art can determine that the above-mentioned detection product or resultant product derives from the gene of the present invention.

The marker of the present invention can be designed based on, for example, the base sequence of a mouse ECAT15-1 gene shown by SEQ ID NO: 1, human ECAT15-1 gene shown by SEQ ID NO: 3, mouse ECAT15-2 gene shown by SEQ ID NO: 5, human ECAT15-2 gene shown by SEQ ID NO: 7, mouse Rnf17 gene shown by SEQ ID NO: 9, human Rnf17 gene shown by SEQ ID NO: 11, mouse LOC380905 gene shown by SEQ ID NO: 13, human TDRD4 gene shown by SEQ ID NO: 15, mouse ECAT16 gene shown by SEQ ID NO: 17, or human ECAT16 gene shown by SEQ ID NO: 33, utilizing, for example, primer 3 (HYPERLINK http://www.genome.wi.mit.edu/cgi-bin/primer/primer3.cgi http://www.genome.wi.mit.edu/cgi-bin/primer/primer3.cgi) or vector NTI (manufactured by Infomax). To be specific, a primer or probe candidate sequence, which is obtained by applying the aforementioned base sequence of the gene of the present invention to a primer 3 or vector NTI software, or a sequence containing at least a part of the sequence, can be used as a primer or probe. Specific examples include primers consisting of the base sequences described in SEQ ID NOs: 19-32.

While the marker of the present invention only needs to have an at least 15 contiguous base length as mentioned above, the length can be appropriately selected and set according to the specific use of the marker.

(1-2) Polynucleotide as a Probe or Primer

Detection of whether a test cell is an ES cell can be performed by evaluating the presence or absence of the expression or the expression level (expression amount) of the gene of the present invention in the test cell.

In this case, the above-mentioned marker of the present invention can be utilized as a primer for specifically recognizing and amplifying RNA, produced by the expression of the gene of the present invention, or a polynucleotide derived therefrom, or a probe for specifically detecting the RNA or a polynucleotide derived therefrom.

For use of the marker of the present invention as a detection primer for ES cells, a marker having a base length of generally 15 bp-100 bp, preferably 15 bp-50 bp, more preferably 15 bp-35 bp can be mentioned. More preferably, a marker having a base length of 20 bp-35 bp can be mentioned. For use as a detection probe, a marker having a base length of generally 15 bp-number of bases of full sequence, preferably 15 bp-1 kb, more preferably 100 bp-1 kb, can be mentioned.

The marker of the present invention can be utilized as a primer or probe in a known method for specifically detecting a particular gene, such as Northern blot method, RT-PCR method, in situ hybridization method, DNA chip and the like, according to a conventional method. By the utilization, the presence or absence of the expression of the gene of the present invention or an expression level (expression amount) thereof in a test cell can be evaluated.

As a measurement target sample, a total RNA prepared from a test cell according to a conventional method may be used, or various polynucleotides prepared further from the RNA may be used. In addition, a cell may be directly used as a measurement target sample.

(1-3) Antibody

The present invention provides an antibody capable of specifically recognizing, as an ES cell detection marker, any of ECAT15-1, ECAT15-2, ECAT16, Rnf17 and LOC380905 (TDRD4) (hereinafter sometimes to be referred to as the protein of the present invention).

Specifically, as the antibody, an antibody capable of specifically recognizing mouse ECAT15-1 containing the amino acid sequence described in SEQ ID NO: 2, human ECAT15-1 containing the amino acid sequence described in SEQ ID NO: 4, mouse ECAT15-2 containing the amino acid sequence described in SEQ ID NO: 6, human ECAT15-2 containing the amino acid sequence described in SEQ ID NO: 8, mouse Rnf17 containing the amino acid sequence described in SEQ ID NO: 10, human Rnf17 containing the amino acid sequence described in SEQ ID NO: 12, mouse LOC380905 containing the amino acid sequence described in SEQ ID NO: 14, human TDRD4 containing the amino acid sequence described in SEQ ID NO: 16, mouse ECAT16 containing the amino acid sequence described in SEQ ID NO: 18 or human ECAT16 containing the amino acid sequence described in SEQ ID NO: 34 can be mentioned. Such antibody is useful as a detection tool of whether the test cell is an ES cell, by detecting the presence or absence of the expression of the protein of the present invention or the level thereof in the test cell.

Here, the "an antibody specifically recognizing (the protein of the present invention)" means a similar specificity as the aforementioned "specific polynucleotide". That is, even if an antibody recognizes two or more kinds of the ECAT16, Rnf17 and LOC380905(TDRD4), it is included in the category of the aforementioned "specific antibody" as long as it does not recognize other irrelevant protein.

In addition, even if an antibody recognizes ECAT15-1 from two or more species (e.g., mouse and human), ECAT15-2 from two or more species (e.g., mouse and human), ECAT16 from two or more species (e.g., mouse and human), Rnf17 from two or more species (e.g., mouse and human), or LOC380905(TDRD4) from two or more species (e.g., mouse and human), it is included in the category of the aforementioned "specific antibody" as long as it does not recognize other irrelevant protein.

The form of the antibody of the present invention is not particularly limited, and the antibody may be a polyclonal antibody for which the protein of the present invention is an immunizing antigen, or a monoclonal antibody against the protein. Moreover, an antibody showing antigen bindability to a polypeptide consisting of at least generally 8 contiguous amino acids, preferably 15 amino acids, more preferably 20 amino acids, of the amino acid sequence of the protein of the present invention is also included in the antibody of the present invention.

The production methods of these antibodies are already well known, and the antibody of the present invention can also be produced according to such conventional methods (Current Protocol in Molecular Biology, Chapter 11.12-11.13 (2000)). Specifically, when the antibody of the present invention is a polyclonal antibody, it can be obtained by using the protein of the present invention expressed in and purified from *Escherichia coli* etc., according to a conventional method, or synthesizing an oligopeptide having a partial amino acid sequence of the protein of the present invention according to a conventional method, to immunize a non-human animal such as domestic rabbit and the like, and obtaining the antibody from the serum of the immunized animal according to a conventional method. On the other hand, in the case of a monoclonal antibody, it can be obtained by immunizing a non-human animal such as mouse and the like with the protein of the present invention expressed in and purified from *Escherichia coli* etc., according to a conventional method, or an oligopeptide having a partial amino acid sequence of the protein, preparing a hybridoma cell by cell fusion of the obtained spleen cell and a myeloma cell and affording the antibody therefrom (Current protocols in Molecular Biology edit. Ausubel et al. (1987) Publish. John Wiley and Sons. Section 11.4-11.11).

The protein of the present invention to be used as an immunizing antigen for the production of the antibody can be obtained by manipulations comprising DNA cloning based on the sequence information (SEQ ID NOs: 1, 3, 5, 7, 9, 11, 13, 15, 17, 33) of the gene provided by the present invention, construction of each plasmid, transfection to host, culture of transformant and protein recovery from the culture. These manipulations can be performed according to methods known to those of ordinary skill in the art, or the methods as described (Molecular Cloning, T. Maniatis et al., CSH Laboratory (1983), DNA Cloning, DM. Glover, IRL PRESS (1985)) and the like.

To be specific, the protein as an immunizing antigen for the production of the antibody of the present invention can be obtained by preparing a recombinant DNA (expression vector) capable of expressing a gene encoding the protein of the present invention in a desired host cell, introducing the vector into the host cell to give a transformant, culturing the transformant and recovering the object protein from the obtained culture. In addition, a partial peptide of the protein of the present invention can also be produced by a general chemical synthesis method (peptide synthesis), based on the information (SEQ ID NOs: 2, 4, 6, 8, 10, 12, 14, 16, 18, 34) of amino acid sequence provided by the present invention.

The antibody of the present invention may also be prepared using an oligopeptide having a partial amino acid sequence of the protein of the present invention. The oligo(poly)peptide used for the production of the antibody desirably has immunogenicity similar to that of the protein of the present invention. Preferably, an oligo(poly)peptide having such immunogenicity and consisting of at least generally 8 contiguous amino acids, preferably 15 amino acids, more preferably 20 amino acids, of the amino acid sequence of the protein of the present invention can be mentioned.

An antibody against the oligo(poly)peptide can also be produced using various adjuvants for the host to enhance the immunological reaction. With no limitation, the adjuvant includes Freund's adjuvant, mineral gel such as aluminum hydroxide, surface active substances such as lysolecithin, pluronic polyol, polyanion, peptide, oil emulsion, keyhole limpet hemocyanin and dinitrophenol, and human adjuvants such as BCG (Bacillus Calmette-Guerin), *Corynebacterium parvum* and the like.

Since the antibody of the present invention specifically binds with the protein of the present invention, the protein of the present invention (ECAT15-1, ECAT15-2, ECAT16, Rnf17 or LOC380905(TDRD4)) can be specifically detected utilizing the antibody. That is, the antibody is useful as a probe for detecting the presence or absence of the expression of the protein of the present invention in a test cell or tissue.

(2) Detection Method of ES Cell

The present invention provides a detection method of ES cell utilizing the aforementioned marker of the present invention.

Specifically, the ES cell detection method of the present invention comprises measuring the gene expression level of the gene of the present invention (ECAT15-1 gene, ECAT15-2 gene, ECAT16 gene, Rnf17 gene or LOC380905 (TDRD4) gene) contained in a test cell, and the protein level (ECAT15-1, ECAT15-2, ECAT16, Rnf17 or LOC380905 (TDRD4)) derived from the gene, and determining whether the test cell is an ES cell.

The detection method of the present invention specifically includes the following.

(2-1) Cases where RNA is Utilized as Measurement Target

When RNA is utilized as a measurement target, ES cell can be detected by a method specifically comprising the following steps (a), (b) and (c):

(a) a step for binding RNA derived from a test cell or a complementary polynucleotide transcribed therefrom, and the marker of the present invention (a polynucleotide derived from any one of ECAT15-1 gene, ECAT15-2 gene, ECAT16 gene, Rnf17 gene or LOC380905(TDRD4) gene), (b) a step for measuring the RNA derived from a test cell or the complementary polynucleotide transcribed therefrom, which has been bound with the marker, with the above-mentioned marker as an index, (c) a step for determining whether or not the test cell is an ES cell, based on the measurement results of the above-mentioned (b).

When RNA is utilized as a measurement target, the detection method of the present invention is performed by detecting and measuring the expression level of the gene of the present invention in the RNA. To be specific, using the marker of the present invention consisting of the aforementioned polynucleotide as a primer or probe, a known method such as the Northern blot method, the RT-PCR method, the DNA chip analysis method, the in situ hybridization analysis method and the like is performed.

When the Northern blot method is utilized, the presence or absence of the expression of the gene of the present invention in RNA and the expression level thereof can be detected and measured using the marker of the present invention as a probe.

To be specific, a method comprising labeling the marker of the present invention (complementary strand) with a radioisotope ($^{32}P$, $^{33}P$ and the like: RI), a fluorescent substance and the like and hybridizing the marker with RNA derived from a test cell, which has been transferred to a nylon membrane and the like according to a conventional method, and detecting a double strand formed by the marker and RNA by measuring the signal derived from the label of the marker (RI or fluorescent substance) using an X-ray film and the like, or detecting and measuring by a radiation detector (BAS-1800II, manufactured by FUJI FILM), a fluorescence detector and the like can be mentioned. Alternatively, a method comprising labeling a marker (probe DNA) according to the protocol using the AlkPhos Direct Labeling and Detection System (manufactured by Amersham Pharmacia Biotech), hybridizing the marker with RNA derived from a test cell, and detecting and measuring the signal derived from the label of the marker by multi bioimager STORM860 (manufactured by Amersham Pharmacia Biotech) can also be employed.

When the RT-PCR method is utilized, the presence or absence of the expression of the gene of the present invention in RNA and the expression level thereof can be detected and measured using the marker of the present invention as a primer. To be specific, a method comprising preparing cDNA from RNA derived from a test cell according to a conventional method, hybridizing the marker of the present invention (a pair of primers) therewith, performing the PCR method according to a conventional method using the cDNA as a template to amplify the region of the target gene (the gene of the present invention), and detecting the obtained amplified double stranded DNA can be mentioned. For detection of the amplified double stranded DNA, a method comprising detection by staining with ethidium bromide after agarose gel electrophoresis, a method comprising performing the above-mentioned PCR using a primer previously labeled with RI or a fluorescent substance and detecting the produced labeled double stranded DNA, a method comprising transferring the produced double stranded DNA to a nylon membrane and the like according to a conventional method, hybridizing the labeled marker of the present invention as a probe with the DNA and detecting the DNA and the like can be used. The produced labeled double stranded DNA product can be assayed by Agilent 2100 Bioanalyzer (manufactured by Yokogawa Analytical Systems) and the like. In addition, it is possible to prepare an RT-PCR reaction solution using SYBR Green RT-PCR Reagents (manufactured by Applied Biosystems) according to the protocol, carry out the reaction in the ABI PRIME 7700 Sequence Detection System (manufactured by Applied Biosystems) and detect the reaction product.

When DNA chip analysis is utilized, a method comprising preparing a DNA chip comprising the marker of the present invention attached as a DNA probe (single strand or double strand), hybridizing the chip with cRNA prepared from RNA derived from a test cell by a conventional method, binding the formed DNA-cRNA double strand with a labeled probe prepared using the marker of the present invention and detecting the double strand can be mentioned.

(2-2) Cases where Protein is Used as Measurement Target

When protein is used as a measurement target, the detection method of the present invention for ES cell is performed by detecting the protein of the present invention (ECAT15-1, ECAT15-2, ECAT16, Rnf17 or LOC380905(TDRD4)) in the test cell. Specifically, ES cell can be detected by a method comprising the following steps (a), (b) and (c):

(a) a step for binding a protein derived from a test cell and the marker of the present invention (antibody recognizing any of ECAT15-1, ECAT15-2, ECAT16, Rnf17 and LOC380905 (TDRD4)), (b) a step for measuring the protein derived from the test cell, which has been bound with the marker, with the above-mentioned marker as an index, (c) a step for determining whether or not the test cell is an ES cell, based on the measurement results of the above-mentioned (b).

More specifically, a method comprising using the marker of the present invention relating to the antibody and a test cell, a test cell extract and the like as a sample, and detecting and quantitating the protein of the present invention by a known method such as the Western blot method, the immunohistological staining method and the like can be mentioned.

The Western blot method can be performed using the marker of the present invention as a primary antibody, thereafter an antibody labeled with a radioisotope such as $^{125}I$ and the like, a fluorescent substance, an enzyme such as horseradish peroxidase (HRP) and the like (antibody bound with primary antibody) as a secondary antibody, detecting and measuring the signal derived from the radioisotope, fluorescent substance and the like of the obtained labeled compound using an X-ray film and the like, radiation measurement device (BAS-1800II: manufactured by FUJI FILM and the like), a fluorescence detector and the like. In addition, after using the marker of the present invention as a primary antibody, detection can be performed using the ECL Plus Western Blotting Detection System (manufactured by Amersham Pharmacia Biotech) according to the protocol, and the measurement can be performed using multi bioimager STORM860 (manufactured by Amersham Pharmacia Biotech).

(2-3) Detection of ES Cell

Whether or not an ES cell (ES-like cell) can be performed by measuring the expression amount (level) of any of the genes of the present invention or the expression amount (level) of any of the proteins of the present invention in a test cell. When any of the genes or proteins of the present invention is expressed, or when the expression level is high as compared to the expression in a somatic cell, the test cell can be determined to be an ES cell. It is desirable to concurrently confirm expression of other genes with ES cell-specific expression such as Oct3/4 and Nanog (ECAT4).

(3) Screening of Somatic Cell Nuclear Reprogramming Substance or ES Cell Undifferentiated State Pluripotency Maintaining Substance and the Like As described in Reference Example 1, the present inventors prepared somatic cells (lymphocytes) from a knock-in mouse in which a βgeo marker gene had been knocked in ECAT3 gene, which is a gene with ES cell-specific expression like the gene of the present invention. The somatic cells were cultured under the culturing conditions of ES cell and selected with G418. As a result, all cells died, and no drug resistant colony was obtained. In contrast, when the aforementioned somatic cells were fused with normal ES cells, cultured under the culturing conditions of ES cell and selected with G418, the surviving cells emerged. The surviving cells were analyzed and, as a result, they expressed ECAT4 and Oct3/4 and were found to be ES-like cells having the properties of ES cell. From the foregoing experimental results, it has been clarified that the ES-like cells emerged because fusion of somatic cell and ES cell initialized (reprogrammed) the nucleus of the somatic cell, and βgeo substituted by ECAT3 gene was expressed to provide the drug resistance.

As mentioned above, a somatic cell containing a gene wherein a marker gene is present at a position permitting expression control by the expression control region of a gene with ES cell-specific expression expresses the marker gene only upon conversion to an ES-like cell. In other words, conversion to ES-like cell can be easily monitored by the expression of a marker gene such as drug resistance and the like. Utilizing the property, a nuclear reprogramming factor inducing the conversion of a somatic cell to an ES-like cell can be efficiently screened for using expression of a marker gene as evidenced by drug resistance and the like as an index. Similarly, using the aforementioned expression of a marker gene as an index, an ES-like cell can be efficiently selected.

Moreover, the aforementioned system of "conversion to ES-like cell is easily monitored by the expression of a marker gene such as drug resistance and the like" can also be applied to the screening of a substance maintaining undifferentiated state and pluripotency of ES cell. Since the aforementioned system of the present invention enables easy monitoring of the ES cell state based on the expression of a marker gene such as drug resistance and the like, for example, a (candidate) substance maintaining undifferentiated state and pluripotency of ES cell can be easily screened for by adding a test substance to the ES cell under culturing conditions incapable of maintaining the ES cell state and examining the presence or absence of cell expressing the marker gene.

There have already been filed patent applications for the foregoing screening methods and the like (Japanese Patent Application No. 2004-276572, filing date: Sep. 24, 2004 (priority date: Feb. 19, 2004), applicant: Shinya Yamanaka, Sumitomo Pharmaceuticals Co., Ltd.) (thereafter international application was filed on Feb. 16, 2005. International Application No.: PCT/JP2005/002842, International Publication No.: WO2005/080598).

The "ES-like cell" produced in the above by conversion from a somatic cell due to a nuclear reprogramming substance refers to a cell having the properties of ES cell, namely, a cell in undifferentiated state and having pluripotency.

In the following, "the gene of the present invention" may refer to a genomic gene according to the common technical knowledge.

(3-1) The Screening Method of the Present Invention for Somatic Cell Nuclear Reprogramming Substance The present invention provides a screening method for a somatic cell nuclear reprogramming substance, which comprises the following steps (a) and (b):

(a) a step for bringing into contact with each other a somatic cell comprising a gene wherein a marker gene is present at a position permitting expression control by the expression control region of a ECAT15-1 gene, ECAT15-2 gene, ECAT16 gene, Rnf17 gene or LOC380905(TDRD4) gene and a test substance, (b) a step following the aforementioned step (a), for determining the presence or absence of the emergence of cells expressing the marker gene, and selecting a test substance allowing the emergence of the cells as a somatic cell nuclear reprogramming substance candidate, The aforementioned "marker gene" refers to any gene that enables cell sorting and selection by introducing the marker gene into cells. Specifically, a drug resistant gene, a fluorescent protein gene, a luminescent enzyme gene, a chromogenic enzyme gene or a gene comprising a combination thereof can be mentioned.

Specifically, as the drug resistant gene, the neomycin resistance gene (neo), tetracycline resistance gene (tet), kanamycin resistance gene, zeocin resistance gene (zeo), hygromycin resistance gene (hygro) and the like can be mentioned. When cells are cultured using a medium comprising each drug (referred to as a selection medium), only those cells incorporating and expressing the drug resistant gene survive. Therefore, by culturing cells using a selection medium, it is possible to easily select cells comprising a drug resistant gene.

Specifically, as the fluorescent protein gene, the GFP (green fluorescent protein) gene, YFP (yellow fluorescent protein) gene, RFP (red fluorescent protein) gene, aequorin gene and the like can be mentioned. Cells expressing these fluorescent protein genes can be detected using a fluorescence microscope. The cells can also be selected by separation and selection using a cell sorter and the like on the basis of differences in fluorescence intensity, or by subjecting the cells to limiting dilution to obtain a cell density of not more than one cell per well, then culturing and growing the cells, and detecting cells (wells) producing fluorescence under a fluorescence microscope. Furthermore, it is also possible to allow colonies to form on a soft agar medium and the like, and to select colonies under a fluorescence microscope and the like.

Specifically, as the luminescent enzyme gene, the luciferase gene and the like can be mentioned. Cells expressing these luminescent enzyme genes can be detected by measuring the amount of luminescence using a luminescence photometer with the addition of a luminescent substrate. The cells can also be selected by subjecting the cells to limiting dilution to obtain a cell density of not more than one cell per well, then culturing and growing the cells, collecting a portion of the cells from each well, and measuring the presence or absence of luminescence with the addition of a luminescent substrate using a luminescence photometer.

Specifically, as the chromogenic enzyme gene, the β galactosidase gene, β glucuronidase gene, alkaline phosphatase gene, or secreted alkaline phosphatase SEAP gene and the like can be mentioned. Cells expressing these chromogenic enzyme genes can be detected by examining for chromogenic in the presence of a chromogenic substrate. The cells can also be selected by subjecting the cells to limiting dilution to obtain a cell density of not more than one cell per well, then culturing and growing the cells, collecting a portion of the cells from each well, and adding a chromogenic substrate to examine for chromogenic.

Specifically, as the gene comprising a combination of these marker genes, the β geo gene, which is the fusion gene of the neomycin resistance gene (neo) and the β galactosidase gene (β-gal), can be mentioned.

All the above-described marker genes are well known to those skilled in the art; vectors harboring such a marker gene are commercially available from Invitrogen, Inc., Amersham Biosciences, Inc., Promega, Inc., MBL (Medical & Biological Laboratories Co., Ltd.) and the like.

Of the aforementioned marker genes, a drug resistant gene or a gene comprising the drug resistant gene is particularly preferable because of the ease of cell selection.

The "somatic cell" as mentioned above refers to any cell except cells that maintain undifferentiated state and pluripotency, such as normal ES cells. Specifically, as examples, (1) tissue stem cells (somatic stem cells) such as neural stem cells, hematopoietic stem cells, mesenchymal stem cells, and spermatogonial stem cells, (2) tissue progenitor cells, (3) differentiated cells such as lymphocytes, epithelial cells, myocytes, and fibroblasts, (4) cells obtained by depriving ES cells of their undifferentiated state and pluripotency by any technique, (5) cells that are fused cells of somatic cells and ES cells, and that do not have an undifferentiated state and pluripotency, and the like can be mentioned.

In the screening method of the present invention, somatic cells comprising a gene wherein a marker gene is present at a position permitting expression control by the expression control region of the gene of the present invention are used as the cells for screening.

The "expression control region" as mentioned herein refers to a region for regulating the expression (transcription) of a gene, meaning a region comprising "a promoter region" or "promoter and enhancer regions".

There are various known methods of allowing a marker gene to be present at a position permitting expression control by the expression control region of the gene of the present invention; the marker gene may be allowed to be present using any method well known to those skilled in the art. There are roughly two cases: (3-1-1) a case where a marker gene is allowed to be present utilizing an individual (mouse), and (3-1-2) a case where a marker gene is allowed to be present in a cellular level without utilizing an individual.

(3-1-1) Method of Allowing a Marker Gene to be Present Utilizing an Individual (Mouse)

When a marker gene is allowed to be present utilizing an individual (mouse), the marker gene is allowed to be present at a position on the genome for expression control by the expression control region of the gene of the present invention. In this case, the gene of the present invention present in the individual may be present in an expressible form, and may be present in a destroyed form.

The expression control region of a gene is normally present upstream of exon 1. Therefore, to ensure that a marker gene undergoes expression control by the expression control region of the gene of the present invention, it is desirable that the marker gene be present downstream of the exon 1 initiation site of the gene of the present invention. In this case, the marker gene may be present at any position, as long as it is downstream of the exon 1 initiation site.

(3-1-1-a) Cases where the Gene of the Present Invention is Destroyed

Although any method well known to those skilled in the art may be used to destroy the gene of the present invention, the most commonly used technique comprises targeted-destroying the gene of the present invention by homologous recombination using a vector that harbors a marker gene, and that causes homologous recombination at an optionally chosen position in the gene of the present invention (hereinafter referred to as targeting vector), to allow the marker gene to be present instead at that position. Thus destroying the gene of the present invention and allowing a marker gene to be present at that position is referred to as "knocking in a marker gene to the gene of the present invention".

That is, as specific examples of the screening method for the somatic cell nuclear reprogramming substance of the present invention, the present invention provides a screening method comprising the following (a) and (b):

(a) a step for bringing into contact with each other a somatic cell comprising a gene resulting from knocking in a gene comprising a drug resistant gene to the ECAT15-1 gene, ECAT15-2 gene, ECAT16 gene, Rnf17 gene or LOC380905 (TDRD4) gene and a test substance, (b) a step following the aforementioned step (a), for determining the presence or absence of surviving cells in a selection medium, and selecting a test substance allowing the emergence of the surviving cells as a somatic cell nuclear reprogramming substance candidate.

Although there are various known methods of knocking in a marker gene, the promoter trap method is suitably used out of them. The promoter trap method comprises inserting a targeting vector not harboring a promoter into a genome by homologous recombination, and allowing the expression of a marker gene by an endogenous promoter (promoter of the gene of the present invention) if homologous recombination has occurred accurately. Specific examples of the method of allowing a marker gene to be present at a position permitting expression control by the expression control region of the gene of the present invention by the promoter trap method are given below.

First, the genomic sequence of the gene of the present invention required for targeting is determined. The genomic sequence can be determined utilizing already publicly known sequence information, if available in, for example, the public database Mouse Genome Resources (http://www.ncbi.nlm.nih.gov/genome/guide/mouse/) and the like. If no sequence information is available, by screening a genomic library available to those skilled in the art by PCR and the like using a part of the gene of the present invention shown by SEQ ID NO:1, 3, 5, 7, 9, 11, 13, 15, 17 or 33 as a primer, it is possible to isolate a genomic clone comprising the desired genome region of the gene of the present invention, and to determine the genomic base sequence. As examples of the genomic library used here, the mouse BAC (bacterial artificial chromosome) library (Invitrogen), the PAC (P1-derived artificial chromosome) library (Invitrogen) and the like can be mentioned.

Next, on the basis of the genomic DNA sequence of the gene of the present invention identified above, the genome region of the gene of the present invention to be replaced by the marker gene is determined (hereinafter referred to as genome region A of the gene of the present invention). The 5'-side region (5'-arm) and the 3'-side region (3'-arm) flanking the genome region A of the gene of the present invention are amplified by performing PCR with genomic DNA as the template and the like. Here, as the genomic DNA serving as the template, the genomic DNA of a mouse BAC clone comprising the gene of the present invention and the like can be mentioned. A primer for the PCR can be designed on the basis of the sequence of the aforementioned genomic DNA of the gene of the present invention. The amplified 5'-arm and 3'-arm are inserted into respective sides flanking the marker gene cassette of the targeting vector for promoter trap. As examples of the targeting vector for promoter trap used here, pBSSK(−)-IRES-β geo, which comprises the IRES (internal ribosome entry site)-β geo (the fusion gene of the β galactosidase and neomycin resistance genes) cassette (Mountford P. et al., Proc. Natl. Sci. USA, 91:4303-4307 (1994)), a similar vector comprising the IRES-Hygro (hygromycin resistance gene) cassette and the like can be mentioned. Here, the IRES-Hygro cassette can be prepared by replacing the β geo portion of the aforementioned IRES-β geo cassette with Hygro (Invitrogen) and the like.

Next, the prepared targeting vector is linearized by digestion with restriction endonuclease, and this is introduced into ES cells by electroporation and the like.

As examples of the ES cells used for the introduction, ES cells such as RF8 cells (Meiner, V. et al., Proc. Natl. Acad. Sci. USA, 93: 14041-14046 (1996)), JI cells (Li, E. et al., Cell, 69:915-926 (1992)), CGR8 cells (Nichols, J. et al., Development, 110:1341-1348 (1990)), MG1.19 cells (Gassmann, M. et al., Proc. Natl. Acad. Sci., USA, 92:1292-1296 (1995)), and commercially available mouse ES cells 129SV (No. R-CMTI-1-15, R-CMTI-1A), mouse ES cells C57/BL6 (No. R-CMTI-2A), and mouse ES cells DBA-1 (No. R-CMTI-3A) (all available from Dainippon Pharmaceutical Co., Ltd.) and the like can be mentioned.

Introduction of the targeting vector to ES cells is performed by electroporation (see Meiner, V. et al., Proc. Natl. Acad. Sci. USA, 93: 14041-14046 (1996) and the like), the calcium phosphate method, the DEAE-dextran method, the electroporation method, the method using a lipid for transfection (Lipofectamine, Lipofectin; Invitrogen) and the like. Subsequently, ES cells incorporating the targeting vector are selected on the basis of the characteristics of the marker gene used (e.g., drug resistant gene). The accurate occurrence of homologous recombination in the ES cells selected can be confirmed by Southern blot using a portion of the gene of the present invention as the probe and the like. Thus, ES cells heterozygously comprising a gene resulting from knocking in a marker gene to the gene of the present invention (genomic gene) can be prepared.

The cultivation of ES cells may be performed using any method known to those skilled in the art. In the case of RF8 cells, for example, a medium of the composition: 15% FBS, 0.1 mM Non Essential Amino Acids (GIBCO BRL), 2 mM L-glutamine, 50 U/ml penicillin-streptomycin, 0.11 mM 2-ME (GIBCO BRL)/Dulbecco's Modified Eagle Medium (DMEM), and the like can be mentioned. A commercially available prepared medium (e.g., No. R-ES-101 from Dainippon Pharmaceutical Co., Ltd. and the like) can also be used.

When feeder cells are used in the cultivation of ES cells, the feeder cells used may be fibroblasts prepared from a mouse embryo by a conventional method or cells of STO cell line derived from a fibroblast (Meiner, V. et al., Proc. Natl. Acad. Sci. USA, 93: 14041-14046 (1996)), and may be a commercial product. As examples of the commercial product, feeder cells such as PMEF-N, PMEF-NL, PMEF-H, and PMEF-HL (all available from Dainippon Pharmaceutical Co., Ltd.) can be mentioned. It is desirable that the feeder cells be used for culturing the ES cells after their growth is stopped by mitomycin C treatment.

When the aforementioned feeder cells are not used in the cultivation of ES cells, the cultivation can be performed with the addition of an LIF (Leukemia Inhibitory Factor). As the LIF, mouse recombinant LIF, rat recombinant LIF (Nippon Chemi-Con Corporation and the like) and the like can be mentioned.

Next, ES cells comprising the aforementioned targeting vector are introduced into a mouse to prepare a knockout mouse (marker gene knock-in mouse). The method of preparing the marker gene knock-in mouse is well known to those skilled in the art. Specifically, a chimeric mouse is prepared by injecting the aforementioned ES cells to mouse (e.g., C57BL/6 and the like) blastocysts, and transplanting the blastocysts into the uterus of a female mouse made to become pseudopregnant (ICR and the like). Subsequently, a heterozygous mutant mouse wherein a marker gene has been heterozygously knocked in is prepared by mating the chimeric mouse and an ordinary mouse (C57BL/6 and the like). By mating such heterozygous mutant mice, a homozygous mutant mouse wherein the marker gene has been homozygously knocked in is obtained.

Regarding the foregoing production of the knock-in mice, refer to ECAT3 knock-in mouse (Tokuzawa, Y., et al., Molecular and Cellular Biology, 23(8): 2699-2708 (2003)), ECAT4 knock-in mouse (Mitsui, K., et al., Cell, 113: 631-642 (2003)), ECAT5 knock-in mouse (Takahashi, K., K. Mitsui, and S. Yamanaka, Nature, 423 (6939): p 541-545 (2003), JP-A-2003-265166) and the like.

The somatic cells used in the screening of the somatic cell nuclear reprogramming substance of the present invention may be somatic cells isolated from the aforementioned heterozygous knock-in mouse, and may be somatic cells isolated from the homozygous knock-in mouse.

(3-1-1-b) Cases where the Gene of the Present Invention is Not Destroyed

As the technique for allowing a marker gene to be present at a position permitting expression control by the expression control region of the gene of the present invention without destroying the gene of the present invention, a technique utilizing a transgenic non-human animal prepared by introducing the BAC vector or PAC vector, wherein a marker gene is present at a position permitting expression control by the expression control region of the gene of the present invention, and the like to an individual such as a mouse or rat can be mentioned. A description is given below for the BAC vector.

The BAC clone comprising the expression control region of the gene of the present invention used here can be isolated and identified on the basis of the sequence information on the gene of the present invention, as stated in (3-1-1-a) above. Replacement of a portion of the gene of the present invention with a marker gene in the BAC clone comprising the gene of the present invention can easily be performed using, for example, Red/ET Recombination (Gene Bridges). The expression control region of each gene of the present invention is normally present upstream of the exon 1 of the gene of the present invention. Therefore, to ensure that a marker gene undergoes expression control by the expression control region of the gene of the present invention, it is desirable that the marker gene be present downstream of the exon 1 initiation site of the gene of the present invention. In this case, the marker gene may be present at any position of the gene of the present invention, as long as it is downstream of the exon 1 initiation site.

Methods of preparing a transgenic animal incorporating the thus-prepared BAC vector wherein a marker gene is present at a position permitting expression control by the expression control region of the gene of the present invention (hereinafter also referred to as the BAC vector comprising a marker gene) are well known; the transgenic animal can be prepared on the basis of, for example, extra issue of Jikken Igaku "Shin Idenshi Kogaku Handbook, 3rd revised edition" (Yodosha Co., Ltd., 1999) and the like. A description of how to prepare a transgenic animal is given below for a mouse.

The method of introducing a gene into a mouse fertilized egg is not subject to limitation; the introduction is possible by the microinjection method, the electroporation method and the like. After the introduction, the egg obtained is cultured and transplanted to the oviduct of a pseudo-dam mouse, after which the recipient mouse is grown, and a desired pup mouse is selected from among the pup mice born. This selection can be performed by, for example, examining the DNA derived from the pup mouse for the presence or absence of the introduced gene by the dot blot hybridization method or the PCR method.

The aforementioned pup mouse and a wild mouse are mated to prepare a heterozygous transgenic mouse (a mouse heterozygously comprising the introduced gene). By mating heterozygous mice, a transgenic mouse homozygously comprising the BAC vector comprising a marker gene can be obtained.

For the screening of the somatic cell nuclear reprogramming substance of the present invention, both the aforementioned somatic cell isolated from a heterozygous transgenic mouse and the somatic cell isolated from a homozygous transgenic mouse can be used. In the case of a transgenic mouse, since the gene of the present invention that the mouse innately has is not destroyed, a somatic cell derived from a homozygous transgenic mouse is preferably utilized.

Furthermore, a double transgenic mouse can be prepared by mating transgenic mice of different ECAT genes. In this case, the individual transgenic mice mated preferably comprise mutually different marker genes.

The somatic cells isolated from the above-described knock-in mouse or transgenic mouse may be any cells wherein the marker gene is not expressed (or is expressed at low expression levels). Specifically, cells other than totipotent cells such as ES cells can be mentioned; for example, (1) tissue stem cells (somatic stem cells) such as neural stem cells, hematopoietic stem cells, mesenchymal stem cells, and spermatogonial stem cells, (2) tissue progenitor cells, or (3) differentiated cells such as lymphocytes, epithelial cells, myocytes, fibroblasts can be mentioned.

(3-1-2) Method of Allowing a Marker Gene to be Present at Cellular Levels without Utilizing an Individual There are various known methods of allowing a marker gene to be present at a position permitting expression control by the expression control region of the gene of the present invention in cells without utilizing an individual; the marker gene may be allowed to be present using any method well known to those skilled in the art. Generally, a method of introducing a vector harboring a marker gene into cells can be mentioned.

The cells used for the transfection may be somatic cells or ES cells. The somatic cells used here may be somatic cells derived from any species such as mouse, human, or monkey. The somatic cells may be primary culture cells or an established line of cells; specifically, primary culture cells such as mouse embryonic fibroblasts (MEF), bone marrow derived mesenchymal stem cells, or spermatogonial stem cells, and established lines of cells like NIH3T3 and the like can be mentioned. As the ES cells, human or simian ES cells, as well as the mouse ES cells mentioned above, can be used. Here, as the human ES cells, KhES-1, KhES-2 or KhES-3 (all available from Stem Cell Research Center, Institute for Frontier Medical Sciences, Kyoto University) and the like can be mentioned; as the simian ES cells, cynomolgus monkey ES cells (Asahi Techno Glass Corporation) can be mentioned. When these ES cells are used in the screening of the present invention, they should be used after being deprived of their undifferentiated state and pluripotency by any technique.

For vector introduction into cells, an ordinary method of introduction suitable to the aforementioned host cell may be used. Specifically, the calcium phosphate method, the DEAE-dextran method, the electroporation method, the method using a lipid for transfection (Lipofectamine, Lipofectin; Invitrogen) and the like can be mentioned.

As the vector used for the introduction, the BAC vector and the PAC vector, which are vectors enabling cloning up to about 300-kb DNA, plasmid vectors, and the targeting vector described in (3-1-1) above and the like can be mentioned. Hereinafter described are methods of preparing a somatic cell wherein a marker gene is present at a position permitting expression control by the expression control region of the gene of the present invention using each of these vectors.

(3-1-2-a) Cases where the BAC Vector or the PAC Vector is Used

By utilizing the BAC vector or PAC vector comprising the expression control region of the gene of the present invention, it is possible to allow a marker gene to be present at a position permitting expression control by the expression control region of the gene of the present invention. A description is given below for the BAC vector.

The BAC clone comprising the expression control region of the gene of the present invention used here (hereinafter referred to as the BAC clone comprising the gene of the present invention) can be isolated and identified on the basis of the sequence information on the gene of the present invention, as stated in (3-1-1) above. Replacement of a portion of the gene of the present invention with a marker gene in the BAC clone comprising the gene of the present invention can easily be performed using, for example, Red/ET Recombination (Gene Bridges). The expression control region of each gene of the present invention is normally present upstream of the exon 1 of the gene of the present invention. Therefore, to ensure that a marker gene undergoes expression control by the expression control region of the gene of the present invention, it is desirable that the marker gene be present downstream of the exon 1 initiation site of the gene of the present invention. In this case, the marker gene may be present at any position, as long as it is downstream of the exon 1 initiation site.

By introducing the thus-prepared BAC vector wherein a marker gene is present at a position permitting expression control by the expression control region of the gene of the present invention to a somatic cell, the cell can be provided as a somatic cell for the screening of the present invention. The BAC vector introduced here may be one kind of BAC vector, and may be two or more kinds of BAC vectors comprising different gene of the present invention. To enable the easy selection of the cell incorporating the BAC vector in a selection medium, it is preferable that a gene comprising a drug resistant gene (hereinafter referred to as a second drug resistant gene) be inserted into the BAC vector. In this case, to enable the expression in the somatic cell, it is necessary that a promoter expressed in the somatic cell be added to the 5' side or 3' side of the second drug resistant gene. Although the second drug resistant gene may be the same kind of drug resistant gene as the marker gene present at a position permitting expression control by the expression control region of the gene of the present invention, and may be a different kind of drug resistant gene, it is desirable that the second drug resistant gene be a different kind of drug resistant gene. When the same kind of drug resistant gene is used, it is possible to previously add the loxP sequence or FRT sequence to both ends of the second drug resistant gene, and select cells incorporating the BAC vector in a selection medium, and then cleaving out the second drug resistant gene with the recombinase Cre or FLP.

When a second drug resistant gene is not inserted into the BAC vector, unlike in the aforementioned case, a second expression vector harboring the second drug resistant gene may be co-transfected with the aforementioned BAC vector, and selection may be performed using a selection medium. In that case, it is desirable that the transfection be performed using the BAC vector in large excess compared with the second expression vector.

When the BAC vector wherein a marker gene is present at a position permitting expression control by the expression control region of the aforementioned gene of the present invention has been introduced into ES cells, ES cells incorporating and expressing the marker gene can be selected on the basis of the properties of the marker gene used. Subsequently, by allowing the differentiation of the ES cells into somatic cells, the ES cells can be converted to somatic cells used for the screening of the present invention. Because ES cells differentiate during culturing conditions without feeder cells, somatic cells obtained by differentiation under these conditions and somatic cells obtained by differentiation using a differentiation inducer known to those skilled in the art, such as retinoic acid, can be used for the screening of the present invention. Here, as examples of the somatic cells differentiated from ES cells, tissue stem cells, tissue progenitor cells, or somatic cells (nerve cells, dermal corneal cells, myocardial cells, skeletal muscle cells, blood cells, islet cells or pigment cells and the like) can be mentioned.

(3-1-2-b) Cases where a Promoter-Free Plasmid Vector is Used

By inserting the fusion gene of the expression control region of the gene of the present invention and a marker gene into a promoter-free plasmid vector and transforming cells therewith, cells for the screening of the present invention can be prepared.

As examples of the vector used here, promoter-free plasmid vectors such as pBluescript (Stratagene) and pCR2.1 (Invitrogen) can be mentioned.

As examples of the expression control region of the gene of the present invention used here, an about 1-kb portion, preferably an about 2-kb portion, upstream of the transcription initiation site of the gene can be mentioned.

The expression control region of each gene of the present invention can be identified by, for example, a technique comprising (i) a step for determining the 5' end by an ordinary method such as the 5'-RACE method (performed using, for example, the 5' full Race Core Kit (manufactured by Takara Shuzo Co., Ltd.) and the like), the oligo cap method, or S1 primer mapping; and (ii) a step for acquiring a 5'-upstream region using the Genome Walker Kit (manufactured by CLONTECH Laboratories Japan, Ltd.) and the like, and determining the promoter activity of the upstream region obtained, and the like. By fusing a marker gene to the 3' side of the thus-identified expression control region of the gene of the present invention, and inserting this into the aforementioned plasmid vector, a plasmid vector wherein the marker gene is present at a position for expression control by expression control region of the gene of the present invention can be prepared.

By introducing the vector thus prepared into a somatic cell or ES cell in the same manner as (3-1-2-a) above, a somatic cell for the screening of the present invention can be prepared.

(3-1-2-c) Cases where a Targeting Vector is Used

By introducing the targeting vector described in (3-1-1) above into a somatic cell or ES cell, a somatic cell for the screening of the present invention can also be prepared.

When the aforementioned targeting vector is introduced into a somatic cell, it is more preferable to use a somatic cell obtained by allowing a gene comprising a drug resistant gene (second drug resistant gene) to be present on the targeting vector in the same manner as (3-1-2-a) above, or co-transfecting a second expression vector comprising a second drug resistant gene with the targeting vector, in order to enable the easy selection of cells incorporating the vector in a selection medium, and selecting using a selection medium, for the screening of the present invention. In the latter case, it is desirable that the transfection be performed using the aforementioned targeting vector in large excess compared with the second expression vector.

When the aforementioned targeting vector is introduced into an ES cell, a cell incorporating and expressing the marker gene can be selected based on the properties of the marker gene on a targeting vector (see Tokuzawa, Y., et al., Molecular and Cellular Biology, 23(8): 2699-2708 (2003) and the like for the production method). The method for inducing an ES cell to a somatic cell is as mentioned above (3-1-2-a).

In the screening step (a) of the present invention, a somatic cell thus prepared and a test substance are brought into contact with each other.

The test substance (test sample) used here is not subject to limitation, and is exemplified by a nucleic acid, a peptide, a protein, an organic compound, an inorganic compound or a mixture thereof and the like; the screening of the present invention is specifically performed by bringing these test substances into contact with the aforementioned somatic cell. More specifically, as the test substance, a cell extract, a gene (genome, cDNA) library, an RNAi library, an antisense nucleic acid, a gene (genome, cDNA, mRNA), a protein, a peptide, a low molecular compound, a high molecular compound, a natural compound and the like can be mentioned. More specifically, the ES cell shown in Reference Examples to be mentioned later, egg, cell extract of ES cell or egg (extraction fraction), cDNA library, genome library or protein library derived from ES cells or egg, or growth factor and the like can be mentioned.

As a derivation for the cDNA library, protein library or cell extract (organic compound, inorganic compound and the like), undifferentiated cells such as ES cells or eggs are preferable, as described above.

Here, a cDNA library can be constructed using a commercially available cDNA library construction kit (e.g., CloneMinor cDNA library construction kit (Invitrogen) or Creator SMART cDNA library construction kit (BD Biosciences) and the like). A protein library can be constructed with reference to WO 00/71580 and the like.

These test substances are brought into contact with somatic cells in an embodiment incorporatable into the somatic cells. For example, when the test sample is a nucleic acid (cDNA library and the like), it is introduced into a somatic cell using calcium phosphate, DEAE-dextran, a lipid for transfection or electric pulse and the like.

The conditions of contact of a somatic cell and a test substance are not subject to limitation, as long as they are culturing conditions (temperature, pH, medium composition and the like) that do not kill the cell, and that are suitable for the incorporation of the test substance.

Cell culture is performed under culture conditions for ES cell before, at, or after, the aforementioned contact of a somatic cell and a test substance. The cultivation of ES cells may be performed using any method known to those skilled in the art. In the case of RF8 cells, for example, a medium of the composition: 15% FBS, 0.1 mM Non Essential Amino Acids (GIBCO BRL), 2 mM L-glutamine, 50 U/ml penicillin-streptomycin, 0.11 mM 2-ME (GIBCO BRL)/Dulbecco's Modified Eagle Medium (DMEM), and the like can be mentioned. A commercially available prepared medium (e.g., No. R-ES-101 from Dainippon Pharmaceutical Co., Ltd. and the like) can also be used.

When feeder cells are used in the cultivation of ES cells, the feeder cells used may be fibroblasts prepared from a mouse embryo by a conventional method or cells of an STO cell line derived from a fibroblast (Meiner, V. et al., Proc. Natl. Acad. Sci. USA, 93: 14041-14046 (1996)), and may be a commercial product. As examples of the commercial product, feeder cells such as PMEF-N, PMEF-NL, PMEF-H, and PMEF-HL (all available from Dainippon Pharmaceutical Co., Ltd.) can be mentioned. It is desirable that the feeder cells be used for culturing the ES cells after their growth is stopped by mitomycin C treatment.

When the aforementioned feeder cells are not used in the cultivation of ES cells, the cultivation can be performed with the addition of an LIF (Leukemia Inhibitory Factor). As the LIF, mouse recombinant LIF, rat recombinant LIF (Nippon Chemi-Con Corporation and the like) and the like can be mentioned.

Although the number of days for the aforementioned culture conditions for ES cell is variable as appropriate depending on cell condition and the like, it is preferably about 1 day to 3 days.

When a gene comprising a drug resistant gene is used as the marker gene, selection with a medium comprising the corresponding drug (selection medium) is performed. The drug may be contained in the medium at the time of contact of a somatic cell and a test substance, and may be contained after the contact. Furthermore, the aforementioned drug may be contained in the medium after cultivation under culture conditions for ES cell.

Following the aforementioned step, the presence or absence of the emergence of cells expressing the marker gene is determined, and a test substance allowing the emergence of the cells is elected as a somatic cell nuclear reprogramming substance candidate (step (b)). The step (b) is described below.

When the marker gene is a gene comprising a drug resistant gene, cells expressing the marker gene can be selected by cultivation using a selection medium as described above. Cells expressing the marker gene can be detected by observation using a fluorescence microscope when the marker gene is a fluorescent protein gene, by adding a luminescent substrate when the marker gene is a luminescent enzyme gene, and by adding a chromogenic substrate when the marker gene is a chromogenic enzyme gene.

If cells expressing the marker gene are detected compared with non-addition of the test substance (including cases where the expression amount has increased), the test sample (test substance) used here is selected as a somatic cell nuclear reprogramming substance candidate.

The aforementioned screening can be repeatedly performed at any frequency as necessary. For example, when a mixture such as a cDNA library or a cell extract is used in the first screening, a somatic cell nuclear reprogramming factor candidate substance can finally be selected by repeatedly performing the same screening with the mixture divided (fractionated) in the second screening and beyond.

As an example of increasing the screening efficiency, a screening system wherein a test substance is added to fused cells of somatic cells and ES cells is effective, rather than using the aforementioned somatic cells as is for the screening. Accordingly, the screening method of the present invention includes a screening method for a somatic cell nuclear reprogramming substance comprising the following steps (a) and (b):

(a) a step for bringing into contact with each other a fused cell (somatic cell) of a somatic cell comprising a gene wherein a marker gene is present at a position permitting expression control by the expression control region of an ECAT15-1 gene, ECAT15-2 gene, ECAT16 gene, Rnf17 gene or LOC380905(TDRD4) gene, and a test substance, (b) a step following the aforementioned step (a), for determining the presence or absence of the emergence of cells expressing the marker gene, and selecting a test substance allowing the emergence of the cells as a somatic cell nuclear reprogramming substance candidate.

"Fused cells" as mentioned herein refers to fused cells of somatic cells and ES cells, wherein the aforementioned marker gene is not expressed (or is expressed at lower expression levels). If the number of colonies increases with the addition of a test substance compared with the number of ES-like-cell colonies resulting from fusion of somatic cells and ES cells, the test substance can be selected as a somatic cell nuclear reprogramming substance candidate.

Whether or not the somatic cell nuclear reprogramming substance (candidate) selected by the screening of the present invention reprograms the nucleus of the somatic cell can be confirmed by determining (1) whether or not the ES-like-cell converted from a somatic cell by the nuclear reprogramming factor (candidate) is expressing an ES cell marker gene such as Oct3/4 or Ecat4 (Nanog), (2) whether or not the aforementioned ES cell differentiates in vitro with retinoic acid stimulation and the like, (3) whether or not a chimeric mouse is born after injection of the aforementioned ES cells into mouse blastocysts, and the like.

(3-2) Knock-In Mouse of the Present Invention and New Application for the Knock-In Mouse (Use as a Source of the Somatic Cell for the Screening of the Present Invention)

The present invention provides a knock-in mouse comprising a gene resulting from knocking in a marker gene to a ECAT15-1 gene, ECAT15-2 gene, ECAT16 gene, Rnf17 gene or LOC380905(TDRD4) gene and an application of the knock-in mouse as a source of the somatic cell used in the screening of the present invention. Regarding the method of preparing the knock-in mouse and the like, the same as described in detail in "(3-1) Screening method of the somatic cell nuclear reprogramming substance of the present invention" above applies.

(3-3) Somatic Cell of the Present Invention

The present invention provides a somatic cell containing a gene wherein a marker gene is present at a position permitting expression control by the expression control region of the gene of the present invention. That is, the present invention provides a somatic cell containing a gene wherein a marker gene is present at a position permitting expression control by the expression control region of ECAT15-1 gene, ECAT15-2 gene, ECAT16 gene, Rnf17 gene or LOC380905(TDRD4) gene. Specifically, a somatic cell containing a gene wherein a marker gene is knocked in ECAT15-1 gene, ECAT15-2 gene, ECAT16 gene, Rnf17 gene or LOC380905(TDRD4) gene is mentioned.

Regarding the method of preparing the somatic cell and the like, the same as described in detail in "(3-1) Screening method of the present invention for somatic cell nuclear reprogramming substance" above applies. The somatic cell of the present invention is effectively used in the aforementioned screening method of the present invention or the ES-like cell selection method of the present invention described below.

(3-4) ES-Like Cell Selection Method of the Present Invention

The present invention also provides an ES-like cell selection method comprising the following steps (a) and (b):

(a) a step for bringing into contact with each other a somatic cell comprising a gene wherein a marker gene is present at a position permitting expression control by the expression control region of a ECAT15-1 gene, ECAT15-2 gene, ECAT16 gene, Rnf17 gene or LOC380905(TDRD4) gene, and a somatic cell nuclear reprogramming substance, (b) a step following the aforementioned step (a), for selecting cells expressing the marker gene as ES-like cells.

A somatic cell wherein a marker gene is present at a position permitting expression control by the expression control region of the gene of the present invention as described with respect to the aforementioned screening method of the present invention is also effectively used for selecting ES-like cells. For example, it is desirable, with stem cell therapy in mind, that an ES-like cell emerging with stimulation of a human somatic cell with a nuclear reprogramming substance be separated (purified) from other cells (somatic cells), and used for subsequent treatment. Because the system of the present invention is a system enabling the easy selection of ES-like cells with the expression of a marker gene such as a drug resistant gene as the index, as described above, it can be effectively used in selecting and separating ES-like cells.

The ES-like cell selection method of the present invention can be used for all purposes of selecting (separating) ES cells not only in the aforementioned treatment of humans, but also in various in vitro and in vivo studies concerning ES cells.

All of the aforementioned methods, namely 1) the method of preparing a somatic cell comprising a gene wherein a marker gene is present at a position permitting expression control by the expression control region of the gene of the present invention, 2) the method of bringing into contact with each other the somatic cell and a somatic cell nuclear reprogramming substance, and 3) the method of selecting cells expressing the marker gene, are the same as those described in "(3-1) Screening method of the present invention for somatic cell nuclear reprogramming substance". When a gene comprising a drug resistant gene as the marker gene is used, cells expressing the marker gene can easily be selected (separated) by cultivation in a selection medium. When a fluorescent protein gene, a luminescent enzyme gene, or a chromogenic enzyme gene is used as the marker gene, the cell can be selected (separated) by utilizing a cell sorter, the limiting dilution method or the soft agar colony method and the like.

"The nuclear reprogramming substance" as mentioned above refers to a substance involved in somatic cell nuclear reprogramming as obtained in the aforementioned screening of the somatic cell nuclear reprogramming substance. In Reference Examples below, cells expressing the marker gene are selected as ES-like cells using ES cells themselves as a somatic cell nuclear reprogramming substance.

It is desirable, with treatment of humans in mind, that the somatic cell used in the ES-like cell selection method be a human somatic cell comprising a vector harboring a marker gene inserted at a position permitting expression control by the expression control region of the gene of the present invention. Specifically, a somatic cell prepared as described below is used.

Specifically, first, somatic cells are prepared by isolating a patient somatic cell from a human and the like. As the somatic cell, somatic cells involved in disease, somatic cells involved in disease treatment and the like can be mentioned. Any vector described in section (3-1-2) above is introduced into this human somatic cell. Specifically, it is desirable that the BAC vector (BAC vector wherein a marker gene is present downstream of the expression control region of the gene of the present invention) or the PAC vector be introduced. The BAC vector (PAC vector) introduced here may be one kind of BAC vector, and may be two or more kinds of BAC vectors comprising different gene of the present invention. By adding a nuclear reprogramming substance to this BAC vector-incorporating cell, ES-like cells are allowed to emerge. These ES-like cells are selected depending on the properties of the marker gene used. For example, when a drug resistant gene is used as the marker gene, ES-like cells can easily be selected with the drug resistance as the index by selection with a selection medium after addition of a nuclear reprogramming substance.

(3-5) Screening Method of the Present Invention for Substance for the Maintenance of Undifferentiated State and Pluripotency of ES Cells The present invention provides a screening method for a substance for the maintenance of undifferentiated state and pluripotency of ES cells, which comprises the following steps (a) and (b):

(a) a step for bringing an ES cell comprising a gene wherein a marker gene is present at a position permitting expression control by the expression control region of ECAT15-1 gene, ECAT15-2 gene, ECAT16 gene, Rnf17 gene or LOC380905 (TDRD4) gene, into contact with a test substance in a medium not allowing the maintenance of undifferentiated state and pluripotency of ES cells, (b) a step following the aforementioned step (a), for determining the presence or absence of cells expressing the marker gene, and selecting a test substance allowing the occurrence of the cells as a candidate substance for the maintenance of undifferentiated state and pluripotency of ES cells.

When ES cells wherein a marker gene is present at a position permitting expression control by the expression control region of the gene of the present invention are cultured in a medium not allowing the maintenance of ES cell properties (undifferentiated state and pluripotency), the expression of the marker gene disappears or decreases. On the other hand, if a substance for the maintenance of undifferentiated state and pluripotency of ES cells is present in the aforementioned medium, the expression of the marker gene persists. By utilizing this property, a substance (candidate) for the maintenance of undifferentiated state and pluripotency of ES cells can easily be screened.

The ES cell used in the aforementioned screening step (a) may be any ES cell, as long as it comprises a gene wherein a marker gene is present at a position permitting expression control by the expression control region of the gene of the present invention. Specifically, for example, ES cells derived from the knock-in mouse described in (3-1-1-a) above, ES cells derived from the transgenic mouse described in (3-1-1-b) above, ES cells comprising the BAC vector or PAC vector described in (3-1-2-a) above, ES cells comprising the plasmid vector described in (3-1-2-b) above, or ES cells comprising the targeting vector described in (3-1-2-c) above can be mentioned.

"The medium not allowing the maintenance of undifferentiated state and pluripotency of ES cells" used in the aforementioned screening step (a) may be any medium, as long as it is a medium not allowing the maintenance of ES cell properties or a medium not allowing the maintenance of undifferentiated state. For example, because it is known that serum or feeder cells are essential for the maintenance of mouse ES cells (maintenance of undifferentiated state and pluripotency) at low densities, the same conditions as the culture conditions for the ES cells, but deprived of serum or feeder cells or both, can be mentioned. Also, because feeder cells are essential for the maintenance of human ES cells (maintenance of undifferentiated state and pluripotency), the same conditions as culture conditions for human ES cell, but deprived of feeder cells, can be mentioned. Furthermore, in the case of human ES cells, because cells that differentiate even in the presence of feeder cells emerge, the culture may be performed in the presence of feeder cells.

Specifically, the same conditions as the culture conditions for ES cell described in the literature (Meiner, V. L., et al., Proc. Natl. Acad. Sci. USA, 93(24): p 14041-14046 (1996)), but deprived of serum or feeder cells or both, and the like can be mentioned as examples.

The aforementioned step (a) is performed by bringing the aforementioned ES cell into contact with a test substance in a medium not allowing the maintenance of undifferentiated state and pluripotency of ES cells. The test substance is brought into contact with the ES cell before, at, or after the ES cells are transferred to the medium not allowing the maintenance of undifferentiated state and pluripotency.

The test substance (test sample) used in this screening is not subject to limitation, and is exemplified by a nucleic acid, a peptide, a protein, an organic compound, an inorganic compound or a mixture thereof and the like; the screening of the present invention is specifically performed by bringing these test substances into contact with the aforementioned ES cell. As the test substance, a secretion product of cells, serum, a cell extract, a gene (genome, cDNA) library, an RNAi library, a nucleic acid (genome, cDNA, mRNA), an antisense nucleic acid, a low molecular compound, a high molecular compound, a protein, a peptide, a natural compound and the like can be mentioned. Specifically, animal serum or a fraction thereof, a secretion product of feeder cells or a fraction thereof and the like can be mentioned.

These test substances (test samples) are brought into contact with ES cells in an embodiment incorporatable into the ES cells. For example, when the test substance is a nucleic acid (cDNA library and the like), it is introduced into ES cells using calcium phosphate, DEAE-dextran, or a lipid for transfection.

When a gene comprising a drug resistant gene as the marker gene is used, selection is performed with a medium comprising the corresponding drug (selection medium). The drug may be contained in the medium at the time of contact of the ES cell and the test substance, and may be contained after the contact. Furthermore, the aforementioned drug may be contained in the medium after cultivation in a medium not allowing the maintenance of undifferentiated state and pluripotency of ES cells in the presence of a test substance.

After the aforementioned step (a), the presence or absence of cells expressing the marker gene is determined, and a test substance allowing the occurrence of the cells is selected as a candidate substance for the maintenance of undifferentiated state and pluripotency of ES cells (step (b)). Regarding the step (b), the same as described in "(1) Screening method of the present invention for somatic cell nuclear reprogramming substance" above applies. If cells expressing the marker gene are observed, the test sample (test substance) used here is selected as a candidate substance for the maintenance of undifferentiated state and pluripotency of ES cells.

The aforementioned screening can be repeatedly performed at any frequency as necessary. For example, when a mixture such as a secretion product of feeder cells or serum is used in the first screening, a candidate substance for the maintenance of undifferentiated state and pluripotency of ES cells can finally be selected by repeatedly performing the same screening with the mixture divided (fractionated) in the second screening and beyond.

Note that when screening is performed using a mixture as the test sample as described above, a substance that promotes the growth of ES cells is possibly be selected along with a substance for the maintenance of undifferentiated state and pluripotency of ES cells. Specifically, when a mixture (fraction A) is subjected to the aforementioned screening method of the present invention, and if surviving cells are confirmed and the number of the surviving cells increases, it is considered that the fraction contains a substance that promotes the growth of ES cells along with a substance for the maintenance of undifferentiated state and pluripotency of ES cells (of course there are some cases wherein a single substance has the properties of the two substances). In that case, the fraction A is further fractionated; if surviving cells are observed but the number of cells does not increase when one resulting fraction (fraction B) is subjected to the screening of the present invention, and also if no surviving cells are observed when the other resulting fraction (fraction C) is subjected to the screening of the present invention, it is considered that the fraction B contains a substance for the maintenance of undifferentiated state and pluripotency of ES cells, whereas the fraction C contains a substance that promotes the growth of ES cells. The screening of the present invention is also useful in selecting such a substance (candidate) that promotes the growth of ES cells.

In addition, when the surviving cells are confirmed and the surviving cells maintained immortalized state, an ES cell immortalization maintaining substance can also be selected in the same manner as in the aforementioned ES cell growth promoting (candidate) substance.

Whether or not the (candidate) substance maintaining undifferentiated state and pluripotency of ES cell selected by the aforementioned screening by the present invention maintains the undifferentiated state and pluripotency of ES cell can be confirmed by examining various abilities of the ES cell by culturing the ES cell under the culturing conditions afforded by adding the candidate to a medium incapable of maintaining the undifferentiated state and pluripotency of the ES cell. Specifically, it can be confirmed by examining, for example, (1) whether or not an ES cell marker gene such as Oct3/4 and Ecat4(Nanog) is expressed in the ES cell cultured under the aforementioned culturing conditions, (2) whether or not the aforementioned ES cell is differentiated in vitro due to a retinoic acid stimulation etc., (3) whether or not a chimeric mouse is born by injection of the aforementioned ES cell into mouse blastcyst and the like.

(3-6) ES Cell of the Present Invention

The present invention provides an ES cell comprising a gene wherein a marker gene is allowed to be present at a position permitting expression control by the expression control region of an ECAT gene. That is, the present invention provides an ES cell comprising a gene wherein a marker gene is allowed to be present at a position permitting expression control by the expression control region of ECAT15-1 gene, ECAT15-2 gene, ECAT16 gene, Rnf17 gene or LOC380905 (TDRD4) gene. The method of preparing the ES cell and the like are as described in detail in (3-1) above. The ES cell of the present invention is effectively used in a screening method for a substance for the maintenance of undifferentiated state and pluripotency of ES cells.

(4) Conjugate with Protein Intracellular Uptake-Promoting Substance

The present invention provides a conjugate of a protein containing any one of ECAT15-1, ECAT15-2, ECAT16, Rnf17 and LOC380905(TDRD4) and a substance that promotes intracellular uptake of the protein.

The protein of the present invention is specifically expressed in an ES cell found by an analysis method similar to that for ECAT4(Nanog) and ECAT5(ERas), and is involved in the functional maintenance of the ES cell. To exhibit an action relating to the functional maintenance of an ES cell, a conjugate of the protein of the present invention and a substance promoting uptake thereof by various cells is effectively used.

Here, the "substance promoting intracellular uptake" may be any of a protein and a chemical substance.

When the intracellular uptake-promoting substance is a protein (peptide), a fusion protein of the protein and the protein of the present invention can be used. The intracellular uptake-promoting protein (peptide) includes, for example, the following (i)-(iii):

(i) HIV-derived TAT (Green and Loewnstein, Cell, 56(6), 1179-88 (1988), Frankel and Pabo, Cell, 55(6), 1189-93 (1988)), *drosophila*-derived Anntenapedia homeodomain (Vives et al., J. Biol. Chem., 272(25), 16010-7 (1997)), HSV-derived VP22 (Elliott and O'Hare, Cell, 88(2), 223-33 (1997)), or a fragment thereof;

(ii) HIV Rev fragment, flock house virus Coat (FHV Coat) fragment, brome mosaic virus Gag (BMV Gag) fragment, human T cell leukemia-II Rex (HTLV-II Rex) fragment, cowpea chlorotic mottle virus Gag (CCMV Gag) fragment, P22 N fragment, λN fragment, ϕ21N fragment or yeast PRP6 fragment (J. Biol. Chem., 276, 5836-5840 (2001));

(iii) peptide having oligoarginine (J. Biol. Chem., 276, 5836-5840 (2001), J. Biol. Chem., 277(4), 2437-2743 (2002)).

As the fragment of the aforementioned (i), since the protein transduction domain (hereinafter "PTD") capable of penetrating a cellular membrane has been identified, as a fragment of HIV TAT, Anntenapedia homeodomain or HSV VP22, which is a protein introduction domain, a fragment of the PTD can be mentioned. It is known that a heterologous protein can be introduced into a cultured cell by fusion of the heterologous protein and PTD, and the production method thereof is also known (Fawell et al., Proc. Natl. Acad. Sci. USA, 91(2), 664-8 (1994), Elliott and O'Hare (1997), Phelan et al., Nature Biotech. 16, 440-443 (1998) and Dilber et al., Gene Ther., 6(1), 12-21 (1999), JP-B-2702285). As regards PTD of HIV TAT, it has been reported that β-galactosidase protein fused with PTD consisting of 11 amino acids derived from HIV TAT protein can infiltrate into living mouse tissue and reach any single cell (Schwarze et al., Science, 285(5433), 1569-72 (1999)).

As the fragment of HIV TAT, specifically, those described in the aforementioned known literatures and the like can be mentioned, with preference given to the HIV TAT fragment described in JP-B-2702285.

Since a basic peptide rich in arginine has an ability to penetrate a cellular membrane, and the fragment (peptide) of HIV TAT is known to have an ability to penetrate a cellular membrane even when the whole center of the molecule is substituted with arginine (J. Biol. Chem., 276, 5836-5840 (2001)), in HIV TAT fragment, Anntenapedia homeodomain fragment and HSV VP22 fragment, multiple amino acids may be substituted with arginine.

As the fragment of HIV Rev of the aforementioned (ii), HIV Rev-(34-50) peptide can be mentioned, as the fragment of FHV Coat, FHV Coat-(35-49) peptide can be mentioned, as the fragment of BMV Gag, BMV Gag-(7-25) peptide can be mentioned, and as the fragment of HTLV-II Rex, HTLV-II Rex-(4-16) peptide can be mentioned. As the fragment of CCMV Gag, CCMV Gag-(7-25) peptide can be mentioned, as the fragment of P22 N, P22 N-(14-30) peptide can be mentioned, as the fragment of λN, λN-(1-22) peptide can be mentioned, as the fragment of ϕ21N, ϕ21N-(12-29) peptide can be mentioned, and as the fragment of yeast PRP6, yeast PRP6-(129-144) peptide can be mentioned. In sequences of these fragments, multiple amino acids may be substituted with arginine.

As a peptide having the oligoarginine of the aforementioned (iii), a peptide having oligoarginine (n=5-9) is preferable, and a peptide having oligoarginine (n=6-8) is more preferable.

While the aforementioned intracellular uptake-promoting protein (peptide) may be fused at either side of the N terminal and C terminal of the protein of the present invention, it is preferably fused at the N terminal side of the protein of the present invention. In that case, a linker sequence may be inserted between the intracellular uptake-promoting protein and the protein of the present invention. The fusion protein can be produced by preparing, by a conventional method, an expression vector containing a polynucleotide encoding a fusion protein, and introducing the vector into a suitable host cell (see the below-mentioned (5) and (6) for specific examples of expression vectors and cells). Moreover, for example, the fusion protein can also be synthesized and purified in vitro using the PureGene system and the like.

When the intracellular uptake-promoting substance is a chemical substance, the chemical substance includes, for example, a compound having a P-glycoprotein-binding activity, a branched peptide having arginine and the like.

Here, the "compound having a P-glycoprotein-binding activity" refers to, for example, BCRP inhibitor. Specifically, for example, GF120918, a BCRP inhibitor, and the like can be mentioned. By chemically binding a compound having a P-glycoprotein-binding activity and the protein of the present invention, the chemical conjugate can be specifically incorporated into various somatic stem cells called SP cells.

The aforementioned "branched peptide having arginine" refers to, for example, a branched peptide having about 8 arginines, which can penetrate a cellular membrane, as described (Biochemistry, 41, 7925-7930, (2002)), and specifically, $(R_2)_4$ peptide, $(RG_3R)_4$ peptide and the like in the literature can be mentioned.

As the binding manner of the protein of the present invention and the protein intracellular uptake-promoting substance, a covalent bond and an ionic bond can be mentioned.

In the case of an ionic bond, for example, an electrostatic complex with collagen, an electrostatic complex with N-acetyl-chitosan and the like can be mentioned.

(5) ES Cell Function-Maintaining Agent

The present invention provides an agent containing a protein for maintaining the function of an ES cell, which contains, as an active ingredient, any one of the proteins of the present invention (ECAT15-1, ECAT15-2, ECAT16, Rnf17 or LOC380905(TDRD4)).

The protein of the present invention is a protein specifically expressed in an ES cell, which is found by a similar analysis method as for ECAT4(Nanog) and ECAT5(ERas), and involved in the functional maintenance of the ES cell. Here, the "functional maintenance of ES cell" refers to the involvement in the maintenance of undifferentiated state of ES cell, maintenance of pluripotency of ES cell, maintenance of growth ability of ES cell, maintenance of immortalized state of ES cell, or functional maintenance of ES cell when introduced into a cell other than the ES cell (conversion to ES-like cell, somatic cell nuclear reprogramming). Particularly, it refers to the involvement in the maintenance of undifferentiated state of ES cell and maintenance of growth ability of ES cell.

As a protein containing any one of the proteins of the present invention (ECAT15-1, ECAT15-2, ECAT16, Rnf17 or LOC380905(TDRD4)) as an active ingredient, the protein of the present invention per se can be used, and a conjugate with the aforementioned intracellular uptake-promoting substance can also be used. These protein and conjugate can be introduced into a cell in a form permitting intracellular uptake, which is well known to those of ordinary skill in the art.

Intracellular introduction in the form of a protein is reversible unlike irreversible gene transfer (chromosomal integration), and is advantageous in that the protein can be added to a medium only when necessary and can be removed from the medium when it becomes unnecessary.

In addition, a polynucleotide containing a gene encoding the protein of the present invention or a conjugate (fusion protein) can also be used as an active ingredient of an agent for maintaining the function of an ES cell. In this case, the aforementioned polynucleotide is preferably inserted into an expression vector and introduced into a cell in the form of a recombinant expression vector.

Here, the expression vector can be appropriately selected according to the host to be used, object and the like, and plasmid, phage vector, viral vector and the like can be mentioned. Specifically, for example, plasmid vectors such as pCEP4, pKCR, pCDM8, pGL2, pcDNA3.1, pRc/RSV, pRc/CMV and the like, viral vectors such as retroviral vector, adenoviral vector, adeno-associated viral vector and the like can be mentioned.

The aforementioned vector may contain a factor such as expression inducible promoter, gene encoding a signal sequence, selection marker gene, terminator and the like. In addition, it may contain a gene encoding a marker protein (marker gene).

Here, the "marker gene" refers to a gene capable of distinguishing the object transgenic cell from non-transgenic cells and, for example, a fluorescent protein gene such as GFP, and CFP and YFP, which are variants of GFP, and the like, a drug resistant gene, a luminescent enzyme gene, a chromogenic enzyme gene and the like can be mentioned. For details, refer to the aforementioned (3-1). By introduction of a vector added with such marker gene into a cell, a cell capable of expressing the gene of the present invention can be conveniently detected and selected.

Moreover, an expression vector containing the gene of the present invention can also be prepared utilizing a conditional gene expression control system. For example, a forcible expression system in which the introduced object gene expresses in the co-presence of tetracycline and does not express in the absence thereof can be mentioned (Niwa et al., (2000). Nat Genet. 24, 372-6). Moreover, as a system for on/off of the object gene expression, recombinase Cre-loxP system, recombinase FLP-FRT system and the like can also be used.

Moreover, the aforementioned vector may be a vector that disappears under given conditions. Specifically, for example, PCAG-IP vector can be mentioned.

As a method for introduction into a cell, for example, known methods of the calcium phosphate method, the DEAE-dextran method, the electroporation method, a method using a lipid for transfection (Lipofectamine, Lipofectin; Gibco-BRL), the microinjection method, the electric pulse method and the like can be mentioned.

The agent of the present invention for maintaining the function of an ES cell can be introduced into various mammalian cells. The mammalian cell refers to a cell derived from a tissue, organ etc. of a mammal, such as human, simian, mouse, rat and the like, and it may be a primary cell taken out from an individual, or a cultured cell. The kind of the cell may be one maintaining the undifferentiated state and pluripotency, such as ES cell and the like, or it may be a somatic cell ((a) tissue stem cell (somatic stem cell) such as neural stem cell, hematopoietic stem cell, mesenchymal stem cell, spermatogonial stem cell and, the like, (b) tissue progenitor cell, (c) differentiated cell such as lymphocyte, epithelial cell, myocyte, fibroblast and the like). The detail of the cells are described in the aforementioned (3) Screening of somatic cell nuclear reprogramming substance or a substance maintaining the undifferentiated state and pluripotency of ES cell.

While the amount of the agent for maintaining the function of ES cell of the present invention can be appropriately adjusted depending on the kind of cell, number of cell and the like, it is generally 0.0001 μM-1000 μM, preferably 0.0001 μM-10 μM, more preferably 0.0001 μM-1 μM, and is added as necessary to the cell.

The agent of the present invention for maintaining the function of an ES cell can be effectively used as a therapeutic drug or reagent for regenerative medicine or a reagent for the research relating to the regenerative medicine.

(6) ECAT16

(6-1) ECAT16 Gene

The present invention provides a polynucleotide of ECAT16 gene, which consists of any of the following (a)-(d):

(a) a polynucleotide containing the base sequence described in SEQ ID NO: 17 or 33, (b) a polynucleotide containing a base sequence encoding the amino acid sequence described in SEQ ID NO: 18 or 34, (c) a polynucleotide having a homology of 70% or more with the polynucleotide of the aforementioned (a) or (b), and encoding a protein having the function of ECAT16, (d) a polynucleotide hybridizing with the polynucleotide (complementary strand) of the aforementioned (a) or (b) under stringent conditions, and encoding a protein having the function of ECAT16.

The ECAT16 gene in the present invention is a long transcript wherein known Rnf17 gene and LOC380905 gene are ligated with a partial overlap between them, and is a novel gene found by the present inventors.

Here, the "ECAT16 gene" is specifically exemplified by, but not limited to, a mouse ECAT16 gene containing the base sequence described in SEQ ID NO: 17, and a gene having a homology of 70% or more with the mouse ECAT16 gene containing the base sequence described in SEQ ID NO: 17, and encoding a protein having the function of ECAT16, and a gene hybridizing with the complementary strand of the mouse ECAT16 gene containing the base sequence described in SEQ ID NO: 17 under stringent conditions, and encoding a protein having the function of ECAT16 as mentioned above are also encompassed in the category of the ECAT16 gene of the present invention. As such gene, a human ECAT16 gene (SEQ ID NO: 33) is specifically mentioned.

In addition, it is not limited to a human ECAT16 gene containing the base sequence described in SEQ ID NO: 33, and a gene having a homology of 70% or more with the human ECAT16 gene containing the base sequence described in SEQ ID NO: 33, and encoding a protein having the function of ECAT16, and a gene hybridizing with the complementary strand of the human ECAT16 gene containing the base sequence described in SEQ ID NO: 33 under stringent conditions, and encoding a protein having the function of ECAT16 are also encompassed in the category of the ECAT16 gene of the present invention.

Rnf17 gene and LOC380905 gene are not encompassed in the category of the aforementioned "ECAT16 gene".

In the aforementioned (c), the "polynucleotide having a homology of 70% or more" specifically refers to a polynucleotide containing a base sequence having a homology of 70% or more, preferably 80% or more, more preferably 90% or more, particularly preferably 95% or more, with the base sequence shown by the aforementioned SEQ ID NO. In the aforementioned (d), moreover, the "stringent conditions" refers to a gene hybridizing with the complementary strand of the gene specified by the aforementioned SEQ ID NO under stringent conditions.

The "stringent conditions" here can be determined based on the melting temperature (Tm) of the nucleic acid binding a complex or a probe, as taught in Berger and Kimmel (1987, Guide to Molecular Cloning Techniques Methods in Enzymology, Vol. 152, Academic Press, San Diego Calif.) and the aforementioned Molecular Cloning 2nd Edt. Cold Spring Harbor Laboratory Press (1989).

As the hybridization conditions, for example, conditions for hybridizing in a solution containing 6×SSC (20×SSC means 333 mM sodium citrate, 333 mM NaCl), 0.5% SDS and 50% formamide at 42° C. or conditions for hybridizing in a solution containing 6×SSC (without 50% formamide) at 65° C. and the like can be mentioned.

As the washing conditions after hybridization, the conditions of approximately "1×SSC, 0.1% SDS, 37° C." can be mentioned. The complementary strand preferably maintains the hybridized state with the target sense strand even after washing under such conditions. While not particularly limited, more stringent hybridizing conditions include washing at approximately "0.5×SSC, 0.1% SDS, 42° C." and still more stringent hybridizing conditions include washing at approximately "0.1×SSC, 0.1% SDS, 65° C.".

In the above, "having the function of ECAT16" concretely means that the protein shows the property of specifically expressing in an ES cell, which is characteristic of ECAT16, or has an action to maintain the function of ES cell, which is an action of ECAT16.

When the polynucleotide of ECAT16 gene is a duplex, a recombinant expression vector for expressing ECAT16 protein can be produced by inserting the polynucleotide in an expression vector.

The expression vector to be used here can be appropriately selected according to the host to be used, object and the like, and plasmid, phage vector, viral vector and the like can be mentioned.

For example, when the host is *Escherichia coli*, the vector includes plasmid vectors such as pUC118, pUC119, pBR322, pCR3 and the like, and phage vectors such as λZAPII, λgt11 and the like. When the host is a yeast, the vector includes pYES2, pYEUra3 and the like. When the host is an insect cell, pAcSGHisNT-A and the like can be mentioned. When the host is an animal cell, plasmid vectors such as pCEP4, pKCR, pCDM8, pGL2, pcDNA3.1, pRc/RSV, pRc/CMV and the like, viral vectors such as retroviral vector, adenoviral vector, adeno-associated viral vector and the like can be mentioned.

The aforementioned vectors may contain factors such as an expression-inducible promoter, a gene encoding a signal sequence, a selection marker gene, a terminator and the like. It may contain a gene encoding a marker protein (marker gene). As to the marker gene, refer to the aforementioned (3-1).

The aforementioned expression vector may contain a sequence corresponding to the aforementioned conditional gene expression control system (Niwa et al., (2000). Nat Genet. 24, 372-6.), recombinase Cre-loxP system, recombinase FLP-FRT system and the like. Moreover, the aforementioned vector may also be a vector (e.g., pCAG-IP vector) that disappears under certain conditions.

To facilitate isolation and purification, a sequence allowing the expression as a fusion protein with thioredoxin, His tag, GST (glutathione S-transferase) etc. may be added. In this case, a GST fusion protein vector (pGEX4T and the like) having an appropriate promoter (lac, tac, trc, trp, CMV or SV40 early promoter and the like) that functions in a host cell, a vector (pcDNA3.1/Myc-His and the like) having a tag sequence of Myc, His and the like, a vector (pET32a) expressing a fusion protein with thioredoxin and His tag, and the like can be used.

By transforming a host with the expression vector prepared above, a transformed cell containing the expression vector can be produced.

As the host used here, *Escherichia coli*, yeast, insect cell, animal cell and the like can be mentioned. As *Escherichia coli, E. coli* K-12 series HB101 strain, C600 strain, JM109 strain, DH5α strain, AD494(DE3) strain and the like can be mentioned. As the yeast, *Saccharomyces cerevisiae* and the like can be mentioned. As animal cells, L929 cell, BALB/c3T3 cell, C127 cell, CHO cell, COS cell, Vero cell, Hela cell, 293-EBNA cell and the like can be mentioned. As the insect cell, sf9 and the like can be mentioned. In addition, various cells (ES cell, somatic cell) described in the aforementioned (5) can also be used.

As a method for introducing an expression vector into a host cell, conventional introduction methods suitable for the aforementioned host cell can be used. Specifically, the calcium phosphate method, the DEAE-dextran method, the electroporation method, a method using a lipid for transfection (Lipofectamine, Lipofectin; Gibco-BRL), the electric pulse method and the like can be mentioned. After introduction, by cultivation in a conventional medium containing a selection marker, a transformed cell wherein the aforementioned expression vector has been introduced into the host cell can be selected.

By continuously culturing the transformed cell obtained above under preferable conditions, ECAT16 can be produced. The obtained protein can be further isolated and purified by a general biochemical purification means. Here, as the purification means, salting-out, ion exchange chromatography, adsorption chromatography, affinity chromatography, gel filtration chromatography and the like can be mentioned. When the protein of the present invention is expressed as a fusion protein with the aforementioned thioredoxin, His tag, GST etc., it can be isolated and purified by a purification means utilizing the properties of the fusion protein and tag.

(6-2) ECAT16 Protein

Moreover, the present invention provides ECAT16 protein which is any of the following (a)-(c):

(a) a protein containing the amino acid sequence described in SEQ ID NO: 18 or 34, (b) a protein having a homology of 70% or more with the protein of the aforementioned (a), and having the function of ECAT16 protein, (c) a protein having an amino acid sequence of the protein of the aforementioned (a), wherein one or multiple amino acids have been substituted, deleted and/or added, and having the function of ECAT16.

Here, the "ECAT16" is specifically exemplified by, but not limited to, a mouse ECAT16 protein containing the amino acid sequence described in SEQ ID NO: 18, and a protein having a homology of 70% or more with the mouse ECAT16 protein containing the amino acid sequence described in SEQ ID NO: 18, and encoding a protein having the function of ECAT16, and a mouse ECAT16 protein containing the amino acid sequence described in SEQ ID NO: 18 wherein one or multiple amino acids are substituted, deleted and/or added, and having the function of ECAT16 protein are also encompassed in the category of the ECAT16 of the present invention. As such protein, a human ECAT16 (human ECAT16 protein, SEQ ID NO: 34) is specifically mentioned.

In addition, a protein having a homology of 70% or more with the human ECAT16 protein containing the amino acid sequence described in SEQ ID NO: 34, and encoding a protein having the function of ECAT16, and a human ECAT16 protein containing the amino acid sequence described in SEQ ID NO: 34 wherein one or multiple amino acids are substituted, deleted and/or added, and having the function of ECAT16 protein are also encompassed in the category of ECAT16 of the present invention.

Rnf17 gene and LOC380905 are not encompassed in the category of the aforementioned "ECAT16".

In the aforementioned (B), the "protein having a homology of 70% or more" specifically refers to a polypeptide containing an amino acid sequence having a homology of 70% or more, preferably 80% or more, more preferably 90% or more, particularly preferably 95% or more, with the amino acid sequence shown by the aforementioned SEQ ID NO.

In the aforementioned (c), the "protein containing an amino acid sequence wherein one or multiple amino acids are substituted, deleted and/or added" refers to proteins such as an artificially prepared, what is called, an altered protein, allelic variant present in the living organism and the like.

Here, the number of mutated amino acids and mutated site in a protein is not limited as long as the activity of ECAT16 can be maintained. The index with which to determine how and how many amino acid residues should be deleted, substituted and/or added can be found using computer programs well known to those of ordinary skill in the art, such as DNA Star software. For example, the number of mutations is typically within 10% of the total amino acids, preferably within 5% of the total amino acids. The amino acids to be substituted are preferably those having the properties (polarity, charge, solubility, hydrophobicity, hydrophilicity, amphipathicity and the like of the residue) similar to those of the amino acid before substitution, from the aspect of the maintenance of protein structure. For example, Ala, Val, Leu, Ile, Pro, Met, Phe and Trp are amino acids classified as non-polar amino acids, Gly, Ser, Thr, Cys, Tyr, Asn and Gln are amino acids classified as uncharged amino acids, Asp and Glu are amino acids classified as acidic amino acids, and Lys, Arg and H is are amino acids classified as basic amino acids. Using these as indices, therefore, the amino acids belonging to the same group can be appropriately selected.

In the above, "having the function of ECAT16" concretely means that the protein shows the property of specifically expressing in an ES cell, which is characteristic of ECAT16, or has an action to maintain the function of ES cell, which is an action of ECAT16.

The above-mentioned ECAT16 protein can be obtained by cultivating the aforementioned transformant. In addition, it can also be synthesized in vitro using, for example, PureGene system and the like.

(6-3) Antibody Specifically Binding with ECAT16 Protein

The present invention provides an antibody specifically binding with ECAT16. The antibody can be produced by the method described in the aforementioned (1-3).

(6-4) Partial Polynucleotide of ECAT16 Gene

The present invention provides a polynucleotide containing at least 15 contiguous bases, which is specific to the polynucleotide of ECAT16 and/or a polynucleotide complementary to the polynucleotide (excluding Rnf17 gene and LOC380905 gene). The detail of the polynucleotide is described in the aforementioned (1-1) and (1-2).

(6-5) Partial Polypeptide of ECAT16

The present invention provides a polypeptide containing at least 6 contiguous amino acids, which is specific to ECAT16 (excluding Rnf17 and LOC380905). Here, the reason for the definition of "at least 6 amino acids" is that six amino acids are generally sufficient to distinctively define one protein from other proteins. A polypeptide preferably containing 8 amino acids, more preferably not less than 10 amino acids, is provided.

(6-6) Animal Having Genetically Modified ECAT16 Gene

The present invention provides a genetically modified animal wherein ECAT16 gene is artificially inserted into a chromosome, or knocked out. Here, the "genetically modified animal wherein ECAT16 gene is artificially inserted into a chromosome" refers to an ECAT16 gene transgenic animal, and the "genetically modified animal wherein ECAT16 gene is knocked out" refers to an ECAT16 gene knockout animal or knock-in animal.

The method for preparing the genetically modified animal is well known to those of ordinary skill in the art and, for example, it can be produced by the method described in the aforementioned (3-1).

(6-7) Antisense Nucleic Acid or siRNA of ECAT16 Gene

The present invention provides an antisense nucleic acid or siRNA of ECAT16 gene. Here, the "antisense nucleic acid" refers to an antisense polynucleotide and an antisense oligonucleotide, which is specifically exemplified by an antisense nucleic acid complementary to the base sequence described in SEQ ID NO: 17 or SEQ ID NO: 33 or a part thereof.

An antisense nucleic acid generally consists of about 10-1000, preferably about 15-500, more preferably about 16-30, bases. To prevent degradation due to hydrolase such as nuclease and the like, the phosphoric acid residue (phosphate) of each nucleotide constituting the antisense DNA is optionally substituted, for example, by a chemically modified phosphoric acid residue such as phosphorothioate, methylphosphonate, phosphorodithionate and the like. These antisense nucleic acids can be produced using a known DNA synthesizer and the like.

The aforementioned antisense nucleic acid can be hybridized with RNA of ECAT16 gene or a primary transcript capable of generating the RNA by post-transcriptional processing, and can inhibit synthesis or function of RNA of ECAT16 gene, or control/regulate expression of the ECAT16 gene via the interaction with the RNA.

It is also possible to use the antisense nucleic acid of the present invention in a special form of liposome or microsphere. As such form, a polycation (e.g., polylysine) that acts to neutralize the charge on a phosphoric acid group skeleton, hydrophobic ones such as a lipid that enhances interaction with cellular membrane, or increases nucleic acid uptake (e.g., phospholipids, cholesterol and the like) and the like can be mentioned. Preferable lipid to be added includes cholesterol and derivatives thereof (e.g., cholesterylchloroformate, cholic acid and the like). They can be attached to the 3'-end or the 5'-end of the nucleic acid, and may be attached via a base, sugar or an intramolecular nucleoside bond. As other groups, a capping group specifically configured at the 3'-end or the 5'-end of the nucleic acid, which prevents degradation by nuclease such as exonuclease, RNase and the like can be mentioned. As the capping group, hydroxyl-protecting groups known in the field, including glycol such as polyethylene glycol, tetraethylene glycol and the like, can be mentioned but the capping group is not limited thereto.

In the above, the “siRNA” refers to a short interfering RNA. Specifically, it refers to a double stranded oligoRNA complementary to a partial sequence in a coding region (including intron portion in the case of primary transcript) of mRNA of ECAT16 gene or its primary transcript. While the phenomenon of what is called RNA interference (RNAi), wherein introduction of a short double stranded RNA into a cell causes degradation of mRNA complementary to the RNA has been known for nematode, insect, plant etc., this phenomenon has recently been confirmed to occur in animal cells as well (Nature, 411(6836): p 494-498 (2001)). A double stranded oligoRNA having the RNAi activity can be prepared by synthesizing each of the sense strand and antisense strand using a DNA/RNA synthesizer, and annealing them in a suitable annealing buffer.

Each substance described in (6-1)-(6-7) above can be effectively used as a reagent for the mechanism analysis relating to ES cell or for the researches relating to regenerative medicine.

(7) ECAT15s Derived from 129 Mouse ES Cell

The present invention provides mouse ECAT15-1 gene (polynucleotide) containing the base sequence described in SEQ ID NO: 1, and mouse ECAT15-2 gene (polynucleotide) containing the base sequence described in SEQ ID NO: 5. In addition, the present invention provides mouse ECAT15-1 containing the amino acid sequence described in SEQ ID NO: 2, and mouse ECAT15-2 containing the amino acid sequence described in SEQ ID NO: 6. These base sequences and amino acid sequences of ECAT15s derived from 129 mouse ES cell are different from those of the gene registered in a public gene bank (GenBank etc.) in several amino acid residues and the genes are novel genes.

Based on the aforementioned (6-1)-(6-7), gene, protein, expression vector, transformed cell, antibody, partial polynucleotide, partial peptide, and genetically modified animal of ECAT15-1 gene and ECAT15-2 gene can also be produced.

(8) ECAT15-1 and ECAT15-2 Complex

The present invention provides a complex of ECAT15-1 and ECAT15-2. As long as a complex of ECAT15-1 and ECAT15-2 is formed, additional ECAT15-1 may be bound to form a complex, and additional ECAT15-2 may be bound to form a complex. In addition, the complex can be processed into a conjugate with a substance promoting the intracellular uptake (see the aforementioned (4)).

Such ECAT15-1 and ECAT15-2 complex, or a conjugate with a substance promoting uptake of the complex into a cell can be used as an active ingredient of the agent for maintaining the ES cell function shown in the aforementioned (5). More specifically, it can be used as an active ingredient of an agent for maintaining the undifferentiated state of ES cell and an agent for maintaining the growth ability of ES cell. Since ECAT15-1 and ECAT15-2 form a complex, they are preferably used simultaneously as an agent for maintaining the function of ES cell.

Furthermore, the present invention provides an agent of the function of an ES cell, which comprises the following (a) and (b):

(a) a polynucleotide containing ECAT15-1 gene or an expression vector containing the same, (b) a polynucleotide containing ECAT15-2 gene or an expression vector containing the same, as an active ingredient. Since these polynucleotides are expressed to form a complex, they are preferably used simultaneously for an agent for maintaining the function of ES cell.

In the above, “ECAT15-1”, “ECAT15-2”, “ECAT15-1 gene” and “ECAT15-2 gene” are not limited to particular sequences as mentioned above, and those containing an amino acid sequence or base sequence similar to the particular sequence are also included.

The present invention is explained in detail in the following by referring to Examples, which are not to be construed as limitative.

EXAMPLE 1

Identification of Genes with ES Cell-Specific Expression

To identify genes with ES cell-specific expression, an Expressed Sequence Tag (EST) database was analyzed by the Digital Differential Display method. The frequency of gene expression in the libraries derived from the following 5 kinds of cells and organs were analyzed by the Digital differential display method. The number in the parenthesis for each group is the number of analyzed clones. For Group 1 to Group 5, all the corresponding libraries were analyzed. Since the data of Group 6 contained enormous quantity, 23 libraries extracted while including organs and cells of the entire body as many kinds as possible were analyzed.

Group 1 fertilized eggs from 1-cell stage to blastocyst (49050 clones)

Group 2 ES cell or Embryonic carcinoma cells (32277 clones)

Group 3 fetus up to 8.5 days after fertilization (46728 clones)

Group 4 fetus after 9 days from fertilization (128882 clones)

Group 5 testis (65685 clones)

Group 6 other cells, tissues (272460 clones)

As regards the set expected to be specifically expressed in fertilized eggs and pluripotent cells, such as ES cell and the like, by the Digital differential display method, the mouse-derived EST database was searched using BlastN to examine if the ESTs were present only in the pluripotent cell-derived libraries.

The database and analysis program had the following URLs.

Unigene Mouse Sequence Collection http://www.ncbi.nlm.nih.gov/UniGene/Mm.Home.html Digital differential display http://www.ncbi.nlm.nih.gov/UniGene/info_ddd.html Blast search http://www.ncbi.nlm.nih.gov/BLAST/

Among the ECAT candidate genes selected based on the analysis by the Digital differential display method and EST database search by BlastN, the present inventors took note of ECAT15-1 containing a DNA binding domain, SAP (SAF-A/B, Acinus, and PIAS) motif, and Rnf17 suggested of binding with an oncogene myc. The expression of these two genes in ES cells and 13 kinds of organs was analyzed by RT-PCR. That is, expression of ECAT15-1 gene and RNF17 (RNF17, long form) gene in ES cells (undifferentiated/differentiated) and 13 kinds of organs of adult mouse was analyzed by RT-PCR. The primer sequences used were as follows.

```
[ECAT15-1]
                                        (SEQ ID NO: 19)
ECAT15-1-gw-s:    CACCATGGAGACTGCTGGAGACAAGAAG

                                        (SEQ ID NO: 20)
ECAT15-1-gw-as2:  GGACCTATTCCAGAGGAACTGTCAC

[RNF17]
                                        (SEQ ID NO: 27)
Rnf17-RT-S:       GACCGGGCTGGCTTCCTGTCACCTAGT

                                        (SEQ ID NO: 28)
Rnf17-RT-AS:      TTTACCATTTTCGGTGGCAAGGCTTCC
```

The analysis results of ECAT15-1 gene are shown in FIG. 1, and the analysis results of Rnf17 gene are shown in FIG. 2.

ECAT15-1 gene was expressed in undifferentiated ES cells (MG1.19 ES cell and RF8 ES cell), and the expression markedly decreased when the ES cells were treated with retinoic acid to induce differentiation. The expression was not detected in 13 kinds of organs of adult mouse. Rnf17 gene (Rnf17L in the Figure) was expressed only in undifferentiated ES cells (MG1.19 ES cell and RF8 ES cell) and testis. Expression in testis is highly likely derived from primordial germ cell or spermatocyte as in the case of Oct3/4 gene. From these results, it has been clarified that ECAT15-1 gene and Rnf17 gene are both genes with ES cell-specific expression.

As a gene similar to ECAT15-1 gene in the sequence and structure, ECAT15-2 gene is present. Thus, ECAT15-2 was also subjected to a similar RT-PCR analysis (FIG. 1). The primer sequences used were as follows.

```
[ECAT15-2]
                                        (SEQ ID NO: 21)
ECAT15-2-gw-s:    CACCATGTCATACTTCGGCCTGGAGACT

                                        (SEQ ID NO: 22)
ECAT15-2-gw-as2:  ACTCTACTCTTTTCTCCTTTGGCACCC
```

As a result, a similar expression pattern as with ECAT15-1 was detected, showing that the gene is a gene with ES cell-specific expression.

As for Rnf17, there is another gene LOC380905 overlapping therewith on the genome. Thus, LOC380905 was also subjected to a similar RT-PCR analysis (FIG. 2). The primer sequences used were as follows.

```
[LOC380905]
                                        (SEQ ID NO: 29)
LOC380905-RT-S:   AAGCTGGCATATGTTGAACCAAGTAAA

                                        (SEQ ID NO: 30)
LOC380905-RT-AS:  TTCATAAGATGCTAGGCCCTCTTTCAC
```

As a result, a similar expression pattern as with Rnf17 was detected, showing that the gene is a gene with ES cell-specific expression.

From the foregoing, it has been clarified that ECAT15-1 gene, ECAT15-2 gene, Rnf17 gene and LOC380905 gene are all ECAT genes showing ES cell-specific expression, and are marker genes that characterize ES cells.

EXAMPLE 2

Identification of Base Sequence and Amino Acid Sequence of Each Gene

Then, the base sequences and amino acid sequences of the aforementioned ECAT15-1 gene, ECAT15-2 gene, Rnf17 gene and LOC380905 gene were identified.

cDNAs of ECAT15-1 gene and ECAT15-2 gene were amplified from mRNA of RF8 ES cell by the RT-PCR method and the base sequences thereof were determined. The determined base sequence of mouse ECAT15-1 (mECAT15-1) is shown in SEQ ID NO: 1 and the amino acid sequence thereof is shown in SEQ ID NO: 2. The base sequence of mouse ECAT15-2 (mECAT15-2) is shown in SEQ ID NO: 5 and the amino acid sequence thereof is shown in SEQ ID NO: 6. The base sequences and amino acid sequences are different from those of the gene registered in a public gene bank (GenBank etc.) in several amino acid residues and the genes are novel genes.

As the human homologous genes of mouse ECAT15, hECAT15-1 (SEQ ID NOs: 3, 4) and hECAT15-2 (SEQ ID NOs: 7, 8) were identified from a gene database, respectively.

For mouse Rnf17 (mRnf17), SEQ ID NOs: 9 and 10 were identified and as a human homologous gene thereof, hRnf17 (SEQ ID NOs: 11, 12) were identified. In addition, for mouse LOC380905 (mLOC380905), SEQ ID NOs: 13 and 14 were identified and as a human homologous gene thereof, hTDRD4 (SEQ ID NOs: 15, 16) were identified from a gene database, respectively.

EXAMPLE 3

Identification of ECAT16 Gene

The expression of Rnf17 gene and LOC380905 gene in RF8 ES cell was examined by Northern blot analysis. As a result, an about 2 kb band corresponding to Rnf17 or LOC380905 was not confirmed when Rnf17 specific probe and LOC380905 specific probe were used, but an about 4 kb novel band alone was confirmed. The gene corresponding to the novel band was named ECAT16 gene.

Then, the expression of these genes was analyzed by RT-PCR. The primer sequences used were as follows.

```
[primers for amplification of Rnf17L ORF]
                                        (SEQ ID NO: 23)
Rnf17-S:          CACCATGGCGGCAGAGGCTTCGTCGACCGG
```

-continued

```
                                    (SEQ ID NO: 24)
Rnf17L-AS:       CTAAAACTCCACAGCCTTTGAGGGAGAATC

[primers for amplification of LOC380905 ORF]
                                    (SEQ ID NO: 25)
LOC380905-ORF-S:  CACCATGAAGTCTGAACCATACAGTGA

                                    (SEQ ID NO: 26)
LOC380905-ORF-AS: TTAGGAGGAGGAGGCCCTTCTCTCTCT

[primers for amplification of ECAT16 ORF]
                                    (SEQ ID NO: 23)
Rnf17-S:         CACCATGGCGGCAGAGGCTTCGTCGACCGG

                                    (SEQ ID NO: 26)
LOC380905-ORF-AS: TTAGGAGGAGGAGGCCCTTCTCTCTCT
```

As a result, expression was detected for every gene (ECAT16 gene, Rnf17 gene and LOC380905 gene), where the expression amount of ECAT16 gene was strikingly high. Hence, it has been clarified that the expression of Rnf17 (Rnf17L) gene and LOC380905 gene as shown in FIG. 2 was mostly the expression of ECAT16 gene, or the ECAT16 gene was the main body of the gene with ES cell-specific expression.

cDNA of ECAT16 gene was amplified from mRNA of RF8 ES cell by the RT-PCR method and the base sequence thereof was determined. The determined base sequence of mouse ECAT16 gene is shown in SEQ ID NO: 17 and the amino acid sequence is shown in SEQ ID NO: 18. The ECAT16 gene is a long transcript wherein Rnf17 gene and LOC380905 gene are ligated with a partial overlap between them, and has been confirmed to be a novel gene.

Then, human ECAT16 gene was identified cDNA of human ECAT16 gene was amplified from mRNA of the testis derived from human by the RT-PCR method and the base sequence thereof was determined. The primer sequences used for the amplification were as follows.

```
[hECAT16]
                                    (SEQ ID NO: 31)
hRnf17-S:       CACCATGGCGGCAGAGGCTTCGAAGAC

                                    (SEQ ID NO: 32)
hLOC380905-AS:  TTATTCATCTTTATCTGCAAGCCCCATTT
```

The determined base sequence of human ECAT16 gene is shown in SEQ ID NO: 33, and the amino acid sequence thereof is shown in SEQ ID NO: 34. As a result of the blastp, blastn, BLAST, blast (genome) searches, like mouse ECAT16 gene, both the base sequence and amino acid sequence of human ECAT16 gene have not been documented and the gene is novel. The homology between mouse ECAT16 and human ECAT16 at the gene level was 71%, and that at the protein level was 72.5%.

EXAMPLE 4

REFERENCE EXAMPLE 1

The Selection System for Somatic Cell Nuclear Reprogramming Substance Utilizing ECAT3 Gene The coding region of ECAT3 gene was substituted by the fusion gene (βgeo) of β galactosidase and neomycin resistance gene to knock out ECAT3 gene, and the expression of ECAT3 gene was made monitorable by X-Gal staining and drug resistance, whereby a homozygously mutated knock-in mouse (hereinafter ECAT3$^{\beta geo/\beta geo}$ mouse) was prepared. The preparation of ECAT3$^{\beta geo/\beta geo}$ mouse was based on the description of Tokuzawa, Y., et al., Molecular and Cellular Biology, 23(8): 2699-2708 (2003).

Next, lymphocytes were collected from the thymus of the ECAT3$^{\beta geo/\beta geo}$ mouse by a conventional method. These cells were cultured under the culture conditions for ES cell described in the literature (Meiner, V. L., et al., Proc. Natl. Acad. Sci. USA, 93(24): p 14041-14046 (1996)) for 2 days, and selection with G418 (0.25 mg/ml) was performed. As a result, all these lymphocytes died, with absolutely no drug resistant colony obtained. It was also confirmed that all normal ES cells died at this G418 concentration.

Next, lymphocytes derived from the ECAT3$^{\beta geo/\beta geo}$ mouse and RF8 cells were electrically fused in accordance with the method of Tada et al. (Tada, M., et al., Curr. Biol., 11(19): p 1553-1558 (2001)), the resulting fused cells were cultured on feeder cells (STO cells) under the aforementioned culture conditions for ES cell for 2 days, and selection was performed with G418 (0.25 mg/ml); a large number of ES-cell-like colonies were obtained. These colonies were isolated and cultured, and RNA was recovered. Because Northern blotting revealed that these cells expressed Oct3/4 or ECAT4 (Nanog) in all clones, and also because transplantation of these clones to mouse blastocysts resulted in the formation of a chimeric mouse, it was demonstrated that the cells selected with G418 were ES-like cells surely having ES cell properties. Analysis of these cells by flow cytometry (FACS) showed that the size (Forward scatter) about doubled and the DNA content quadrupled. From these results, it was found that these colonies had become resistant to G418 because lymphocyte nuclear reprogramming (conversion to ES cells) occurred as a result of fusion of lymphocytes derived from the ECAT3$^{\beta geo/\beta geo}$ mouse and normal ES cells. Hence, somatic cells derived from the ECAT3$^{\beta geo/\beta geo}$ mouse become drug-resistant only when converted to ES-like cells. Therefore, it was demonstrated that by utilizing this property, ES-like cells can be selected and a nuclear reprogramming factor that induces conversion to ES-like cells can easily be screened.

EXAMPLE 5

Targeting and Functional Analysis of ECAT15-1 and ECAT15-2

1. Experimental Method

1) Screening of BAC

To obtain a BAC clone of ECAT15, a DNA pool of mouse BAC library (Research Genetics Co., Catalog No. 96021) was screened by PCR according to the manual. Primers (5': ECAT15-BAC-S2: AGATTCATTTACTTCACCGCTCCATCATAC/3': ECAT15-BAC-AS2: TCCTGGTAATAAAATTCCGTCGCTGTTG) (SEQ ID NO: 35 and 36, respectively) designed at about 2 kb upstream of 1$^{st}$ exon of ECAT15-1 were used as the primers. The reaction conditions are described in the following.

Reaction solution (25 μL): 2 mM of dNTP, 5 pmol of 5' and 3' primers, 1 unit of rTaq polymerase, 100 ng of template DNA. Temperature conditions: 94° C. for 5 sec, (94° C. for 2 sec, 55° C. for 2 sec, 72° C. for 5 min)×55 cycles, 68° C. for 5 min, and 4° C. After PCR reaction, the products were subjected to electrophoresis in 2.0% agarose gel containing EtBr, and a screening was performed for clones from which about 560 bp band was amplified. As a result, #290 plate was newly obtained from which such a clone was identified. Because the #290 plate was a 384-well plate, first, a DNA pool was produced in which the contents of 4 wells were brought into 1 well. The PCR was performed under the same conditions with this pool as a template to determine a pool containing the subject clone. Finally, the PCR was performed with each DNA contained in the pool as a template to ultimately obtain a clone comprising both 15-1 and 15-2 of ECAT15 gene. The obtained BAC clone was cultured with shaking in 500 ml of LB medium (12.5 μg/mL of chloramphenicol) overnight at 37° C., the bacteria were harvested, after that the BAC clone was purified with nucleobond kit (MACHEREY-NAGEL Co.). Upon the purification, the clone was suspended by slowly shaking by a shaker, avoiding a vigorous shaking, for example by vortex. For facilitating the lysis of the cells, the cell precipitate was completely suspended by adding 23 mL of S1 solution and shaking, and then to the suspension was added 1 mL of lysozyme chloride (50 mg/mL) and the suspension was further shaken at room temperature for 5 min. After that, the S2 and S3 solutions were mixed therewith by a pipette until a uniform suspension was formed, and then shaken for 5 min on ice. After column purification, DNA was subjected to isopropanol precipitation, washed with 70% ethanol, then air dried for 3-5 min, dissolved in 10 mM Tris-HCl (pH 8.0), and stored at 4° C.

2) Production of BAC Targeting Vector

A BAC targeting vector was produced as described below, using a BAC clone comprising ECAT15-1 and 15-2 and having about 140 kbp in the full-length, along with Rec/ET which is a recombinant enzyme derived from *Escherichia coli.*

1) Design of Oligo for Homologous Recombination by Rec/ET

A targeting vector was produced, wherein a neomycin resistance gene cassette was introduced into 15-1 segment and a hygromycin resistance gene cassette was introduced into 15-2 segment. For this purpose, segments to be introduced into BAC were produced by PCR with selection markers (a neomycin resistance gene and a hygromycin resistance gene) as a template. As the primers for this PCR, total 74 bp of oligos comprising 24 bp of a segment homologous to the template and 50 bp of a segment homologous to the BAC were used. For the segment homologous to the BAC, the absence of the repetitive sequence therein was confirmed to design the oligos (RepeatMasker2: http://ftp.genome.washington.edu/).

```
Primers used for 15-1 segment
15-1recomb5'-s
                                        (SEQ ID NO: 37)
(5'-CCGCTCGAAGTGGCCTTGCGCGAGACCCTGGGGCCCGGGTGTAGAT
GTGTTGGCAGAACATATCCATCGC-3')

15-1recomb 3'-as
                                        (SEQ ID NO: 38)
(5'-GTGGAATATATGACATCAAATACAACCAGCAGTCGTCCATCAGGGG
ATGACTATCAACAGGTTGAACTGATGGC-3')

Primers used for 15-2 segment
15-2-5'Recomb-s
                                        (SEQ ID NO: 39)
(5'-CTGGGAGTAAAATGAAACTGTTTCCTTGCTAAAGGAGTAAATCGTC
TCAGCCCTATGCTACTCCGTCGAAGTTC-3')

15-2recomb3'-as
                                        (SEQ ID NO: 40)
(5'-ACTACTGCCAGTTGATGACTGCTGGAGCACGGAGAGCCATCAGCAG
TCAGCTGGCAGTTTATGGCGGGCGTCCT-3')
```

(2) PCR Conditions

The reaction was performed with KOD+ under the following conditions.

94° C. for 1 min.

20 cycles; 1' 94° C. for 2 sec; 1' 68° C. for 2 min

68° C. for 5 min, followed by holding at 4° C.

(3) Transformation with Rec/ET Expression Plasmid

DH10B which comprises ECAT15 BAC was cultured overnight at 37° C. in 1.0 mL of LB medium containing 12.5 μg/mL of chloramphenicol. A 30 μL aliquot thereof was added to 1.4 mL of the fresh medium as above, and the culture was incubated at 37° C. for 2 hr. The culture was centrifuged at 11000 rpm for 30 sec, and the supernatant was discarded. The pellet was resuspended in Milli-Q water, the suspension was re-centrifuged, and the supernatant was discarded. The pellet was suspended in 40 μL of Milli-Q water, 200 ng of pSC-101-BAD-gbaA vector was added to the suspension, then the suspension was transferred into 1 mm cuvette and subjected to electroporation (BioRad Electroporator: 1350 V, 10 μF, 600 Ohms). The suspension was transferred into an Eppendorf tube with 1 mL of LB medium, and cultured at 30° C. for 70 min. When cultured at 37° C., introduced Rec/ET expression plasmid disappears. The culture was incubated overnight at 30° C. in LB plate containing 12.5 μg/mL of chloramphenicol and 10 μg/mL of tetracycline with light shielding.

(4) Recombination Reaction with Rec/ET

A viable colony was cultured overnight at 30° C. in LB plate containing 12.5 μg/mL of chloramphenicol and 10 μg/mL of tetracycline with light shielding. A 30 μL aliquot thereof was added to 1.4 mL of the fresh medium as above, and the culture was incubated at 37° C. for 2 hr. L-arabinose was added to the culture at a final concentration of 0.2%, and the culture was incubated at 30° C. for 1 hr. The culture was centrifuged at 11000 rpm for 30 sec, and the supernatant was discarded. The pellet was resuspended in Milli-Q water, the suspension was re-centrifuged, and the supernatant was discarded. The pellet was suspended in 40 μL of Milli-Q water, 0.3 μg of the oligos (PCR products) produced above was added to the suspension, and then the suspension was transferred into 1 mm cuvette and subjected to electroporation (BioRad Electroporator: 1350 V, 10 μF, 600 Ohms). The suspension was transferred into an Eppendorf tube with 1 mL of LB medium, and cultured at 30° C. for 70 min. The culture was incubated overnight at 30° C. on LB plate containing 12.5 μg/mL of chloramphenicol and antibiotics corresponding to the selection markers (15-1 segment: 50 μg/mL of kanamycin, and 15-2 segment: 50 μg/mL of hygromycin). A BAC targeting vector was obtained from a viable colony.

(5) BAC Gene Targeting

The obtained BAC targeting vector was treated with SalI (NEB) overnight for linearization, subjected to phenol-chloroform extraction followed by ethanol precipitation, and dissolved in PBS. On the day before, confluent RF8 cells were subcultured to 10 cm cell culture plate at 1:2, and on the day, after washing with PBS, treated with trypsin and recovered into a 15 ml tube. The suspension was centrifuged at 800 rpm for 5 min to remove the supernatant, and the pellet was resuspended in 800 μL of PBS. To this cell suspension was added 20 μg of the linearized targeting vector, and the suspension was transferred into a cuvette for electroporation (BM Equipment. Co.). The electroporation was performed on Gene pullser II (BIO-RAD. Co.) at a setting of 0.25 kV, 500 μF, and infinite resistance. The suspension was let stand for 15 min at room temperature, seeded onto MSTO being cultured on a 100 mm cell culture plate at 1:2, and cultured in an incubator. On the next day of the electroporation, the medium was exchanged with ES medium, and since day 2, the selection was performed by adding 250 μg/mL of G418 (SIGMA. Co.) and 100 μg/mL of hygromycin (SIGMA. Co.). 10 days after, colonies were picked up with a micropipette, transferred into a 96-well plate containing 20 μL of trypsin to perform trypsin treatment, neutralized by adding 180 μL of ES medium, and then subcultured onto MSTO in a 24-well plate. When the cells reached confluence, the cells were treated with trypsin, a fraction thereof was subcultured onto 24-well plate coated with 0.1% gelatin for genome extraction, and the remaining was frozen as a whole plate with cell freezing medium added. When the cells subcultured for genome extraction reached confluence, the cells were washed twice with PBS to extract the genome.

(6) Southern Blotting

10 μg of the extracted genomic DNA was treated with Bcl I (NEB) overnight, and subjected to electrophoresis in 0.7% agarose gel. The gel after electrophoresis was soaked in denaturing buffer (0.5 M NaOH, 1.5 M NaCl), and shaken at 50 rpm for 30 min at room temperature. The gel was rinsed with the distilled water, and soaked in neutralizing buffer (0.5 M Tris-HCl pH7.0, 1.5 M NaCl), and shaken at 50 rpm for 30 min at room temperature. The gel was rinsed with the distilled water, soaked in 20×SSC (3 M NaCl, 0.3 M Na citrate pH7.0), shaken at 50 rpm for 30 min at room temperature, and then blotted overnight onto a nylon membrane (Hybond N, Amersham Biosciences) according to the manual of TURBOBLOTTER Rapid Downward Transfer System/Stack Tray (Schleicher & Schuell). On the next day, the DNA transfer to the nylon membrane was confirmed. The nylon membrane was washed with 2×SSC, and radiated with UV to fix the DNA to the nylon membrane. The membrane was transferred into a hybridization bottle, 7 ml of PerfectHyb Plus HYBRIDIZATION Buffer (SIGMA. Co.) was added thereto, and prehybridization was performed for 1 hr at 68° C. A probe to be used to confirm the genotype of ECAT 15 was prepared as following. A fragment obtained by PCR with ECAT15 BAC as a template, and ECAT15-3' probe-s (5'-GCTCCAAATGACCACAAGACTAACAGGC-3') (SEQ ID NO: 41) and ECAT15-3' probe-as (5'-GTGCACATTCCTCCAAGTAGGTAT GAA A -3') (SEQ ID NO: 42) was labeled with [32P]-dCTP using Rediprime II Random Prime Labeling System (Amersham Biosciences. Co.). The radiation intensity of the labeled probe was measured by liquid scintillation. $1.2\times10^7$ dpm of the probe was treated at 100° C. for 5 min, added to a bottle containing the membrane after prehybridization, and hybridization was performed at 68° C. for 3 hr. After 3 hr, the membrane was washed at room temperature for 5 min by adding an appropriate amount of first wash buffer (2×SSC, 10% SDS). Then, the membrane was washed twice at 68° C. for 20 min by adding an appropriate amount of second wash buffer (0.2×SSC, 10% SDS). After washing, the membrane was wrapped in a plastic wrap, exposed overnight on an imaging plate (Fuji. Co.), and on the next day, analyzed using BAS 5000 (Fuji. Co.).

(7) Quantitative PCR

Design of Quantitative PCR Primers, Taq Man Probe

Taq man probe was 20-30 bases long avoiding G at the 5' end. Continuous Gs not less than 4 was avoided. Primers were designed to sandwich this probe between them. To design the above segments, the absence of the repetitive sequence therein was confirmed (RepeatMasker2). The segments which targeted 15-1, 15-2, and Nanog gene as a control were designed (Cell, 113, p 631-642 (2003)). PCR was performed therewith as following.

Quantitative PCR Reaction Conditions:

2× buffer 6.25 μl; primers 1.25 μL, 1.25 μl; taq man probe 1.25 μl; template 0.5 μl; DDW 2 μl; Total 12.5 μl 94° C. for 3 min; 94° C. for 2 sec, 50° C. for 15 sec, 72° C. for 1 min (40 cycles); holding at 72° C.

```
Primers used:
                                    (SEQ ID NO: 43)
Q15-1-s2     (5'-AGAAGAGAAGAATGAGCGTTACAAT-3'),

                                    (SEQ ID NO: 44)
Q15-1-as2    (5'-GGATTCTAAATTCCTTCCTAACAAA-3'),

                                    (SEQ ID NO: 45)
Q15-2-s      (5'-ATGAATACAGTGTATTTACCAGTGT-3'),

                                    (SEQ ID NO: 46)
Q15-2-as     (5'-GAGCTACTACTGCCAGTTGATGACT-3'),

                                    (SEQ ID NO: 47)
Qnanog-s     (5'-GTCCTTAGAAGTTGCTGTAATGTAA-3'),

                                    (SEQ ID NO: 48)
Qnanog-as    (5'-TCACATAATTATGATTTTAACAGGC-3')

Buffer: QuickGoldSt ar Mastermix Plus
(NIPPON GENE Co.)
Taq man Probes (NIPPON EGT Co.)
                                    (SEQ ID NO: 49)
15-1Taq      (5'-CGGGTGTAGATGTGTTAGGAGAGGA-3'),

                                    (SEQ ID NO: 50)
15-2Taq      (5'-CCTGCAGCTGAACTGACTGCTG-3'),

                                    (SEQ ID NO: 51)
nanogTaq     (5'-TGAATCGAACTAACGTCTGGACGTC-3')
ABI PRISM 7300 (Applied Biosystems Co.)
```

2. Results

As the result of the screening of BAC (Bacterial artificial chromosome), ECAT15 BAC clone comprising full-length ECAT15-1 and 15-2 and having about 140 kbp in the full-length was obtained. ECAT15 BAC targeting vector was produced from this BAC using a recombinant enzyme Rec/ET. In this vector, from $2^{nd}$ exon to $7^{th}$ exon of 15-1 is replaced by a neomycin resistance gene, and from $2^{nd}$ exon to $7^{th}$ exon of 15-2 is replaced by a hygromycin resistance gene (FIG. 3).

This targeting vector was introduced into ES cells (RF8), and investigated to determine whether the resistance marker was introduced by PCR. As a result, the introduction in 15-1 segment (18/18 clones) was confirmed. Moreover, the introduction into 15-2 segment was confirmed as well. When this clone was used in Southern blotting for confirmation of the homologous recombination, a 19.5 kb band to be present only in the homologous recombinant was detected in some clones (3/18 clones) (FIG. 4).

By Southern blotting, confirmation of the homologous recombination was difficult since a site with the possibility of homologous recombination ranged over not less than 40 kb at 5' side, and therefore, quantitative PCR was performed for confirmation. It was expected that the amount of PCR amplification of the recombined segment in a genome of the homologous recombinant should have been halved compared with that in a normal genome. As a result of screening with 15-1 segment, the value was halved in 3 clones. At the same time, when a genome of Nanog (+/−) clone (Cell, 113, p 631-642 (2003)) already confirmed to be a homologous recombinant was used as a control, the value was halved as expected. A similar result was obtained with 15-2 segment in these three clones.

A clone confirmed with both the above described quantitative PCR and Southern blotting was taken to be ECAT15-1 and 2 double heterozygous mutant cell. The 15-1 and 15-2 heterozygous mutant ES cell tended to grow more slowly and more likely to differentiate compared with a control cell (i.e., a cell undergoing no homologous recombination). It is confirmed from these results, that ECAT15 plays an important role in the growth and the maintenance of the undifferentiated state of ES cells.

EXAMPLE 6

Analysis of Protein Complex of CAT15-1 and ECAT15-2

1. Experimental Method

1) Construction of Vector

GATEWAY Cloning Technology (Invitrogen. Co.) was utilized for most of the vector constructions in this study. This procedure results in a recombination reaction between an entry vector having the subject gene and a destination vector effecting the expression in *Escherichia coli* and animal cells, which enables rapid production of an expression vector having the subject gene. The PCR reaction was performed with RF8 cDNA products using the following primers:

```
                                        (SEQ ID NO: 52)
ECAT15-gw-s     (5'-CACCATGGAGACTGCTGGAGACAAGAA
                G-3'),

                                        (SEQ ID NO: 53)
ECAT15-1-gw-as  (5'-TTATCCTTCGAGGCTCTTAGTCAA-3'),

                                        (SEQ ID NO: 54)
ECAT15-2-gw-s   (5'-CACCATGTCATACTTCGGCCTGGAGAC
                T-3'),

                                        (SEQ ID NO: 55)
ECAT15-2-gw-as  (5'-TGTCTACGGCGGCATATTTGGGGG-3'),
```

the PCR products were introduced into pENTR-D-TOPO with TOPO cloning (Invitrogen. Co.) to give pENTR-ECAT15-1 and 2. These vectors and pCAG-Myc-gw-IP or pCAG-Flag-gw-IP vectors were used with GETEWAY Cloning Technology (Invitrogen Co.) to give pCAG-Myc-ECAT15-1, pCAG-Myc-ECAT15-2, pCAG-Flag-ECAT15-1 and pCAG-Flag-ECAT15-2. For production of antibodies, pDEST17 which is an expression vector in *Escherichia coli*, and pENTR-ECAT15-1 or 2 were reacted to give pDEST17-ECAT15-1, 2.

2) Purification of Recombinant Protein and Production of Antibody pDEST17-ECAT15-1 and 2 were introduced into *Escherichia coli* BL21-AI for expression of the recombinant proteins, and the bacteria were seeded onto LB plate containing carbenicillin (100 μg/mL). On the next day, single colonies were picked up, and cultured in 5 mL of LB liquid medium containing carbenicillin (100 μg/mL) at 37° C. until O.D.=0.6. L-arabinose was added to the culture at a final concentration of 0.2%, and the culture was incubated for 4 hr. The bacteria were harvested, 3 ml of Buffer A (0.01 M Tris-HCl pH8.0, 6 M Guanidine Hydrochloride, 0.1 M $NaH_2PO_4$/$Na_2HPO_4$) per 1 g of the weight of the bacteria was added thereto, and the culture was shaken for 1 hr at room temperature. The culture was centrifuged at 10000 G for 30 min to recover the supernatant. 1 ml of Ni-NTA agarose (QIAGEN) washed with Buffer A was added thereto, and the mixture was stirred for not less than 1 hr at room temperature. This mixture solution was applied to 2 ml volume of polystyrene column (PIERCE), the excess buffer was allowed to fall freely. The column was washed twice with 4 ml of Buffer C (0.01 M Tris-HCl pH6.3, 8 M Urea, 0.1 M $NaH_2PO_4$), and then the recombinant protein was eluted with 0.5 ml of Buffer E (0.01 M Tris-HCl pH4.5, 8 M Urea, 0.1 M $NaH_2PO_4$). The elution was performed 4 times, and the harvested recombinant protein was dialyzed overnight against 6 M Urea/PBS with Slide-A-Lyzer Cassette (PIERCE).

Thereafter, to a fraction was added the equal volume of 2× sample buffer (100 mM Tris-HCl pH6.8, 4% SDS, 10% 2-ME, 14% glycerol, 0.0 2% BPB), and the mixture was heat treated at 100° C. for 5 min. The presence and the amount of the recombinant protein were confirmed with SDS-gel electrophoresis and CBB staining. New Zealand White (10-week-old, female) was used as an animal for production of an antibody. For the first immunization, the animal was subcutaneously injected with an emulsion formed by mixing about 200 μg of an antigen protein (0.5 ml) and the equal volume of ADJUVANT COMPLETE FREUND (DIFCO Co.) at about 5 points on the back. 4 weeks after the first immunization, for the second or later immunization, the animal was subcutaneously injected with an emulsion formed by mixing 200 μg of an antigen protein and the equal volume of ADJUVANT INCOMPLETE FREUND at about 5 points on the back in the same manner. For the second or later immunization, the immunization injection was performed up to 5 times, once every two weeks. A week after the second immunization injection, about 20 ml of the blood was drawn from the rabbit ear artery every two weeks. The drawn blood was warmed at 37° C. for 1 hr, let stand overnight at 4° C., and then centrifuged at 3000 rpm for 10 min, and the supernatant was recovered. The supernatant was further centrifuged at 15000 rpm for 10 min, and the supernatant was recovered. This serum was used in Western blotting to confirm the titer of the obtained antibody. On the next week of the $5^{th}$ immunization, the blood was drawn from the ear artery as possible, and then the blood was entirely drawn by heart puncture. The blood was treated as above described to give anti-ECAT15-1 and 15-2 serum.

3) Immunoprecipitation with Transiently Overexpressing Cell

MG1.19 ES cell was transfected with the above described pCAG-Myc-ECAT15-1, pCAG-Myc-ECAT15-2, PCAG-Flag-ECAT15-1 or pCAG-Flag-ECAT15-2 by Lipofectamine 2000 with combinations of Myc-tagged ECAT15-2 (hereinafter Myc15-2) and Flag-tagged ECAT15-1 (hereinafter Flag15-1), Myc-tagged ECAT15-1 (hereinafter Myc15-1) and Flag15-1, or Myc15-2 and Flag-tagged ECAT15-2 (hereinafter Flag15-2). First, the vector is added to 250 μl of DMEM. Lipofectamine 2000 is added to another 250 μl of DMEM. Both were mixed, and the mixture was let stand for 20 min. The cells on a 6-well plate were washed with PBS, and then the above described mixture was added thereto. After 4 hr, 2 ml of the culture medium was added thereto. After 24 hr, the proteins were recovered. At the same time, cells were prepared as control wherein Flag15-1, 2 or pCAG-IP (Mock) were expressed. The NP40 were added to the buffer at 0.05%, the mixture was sonicated, and the supernatant was recovered. 5 μL of Normal mouse IgG Ac was added thereto, and the mixture was rotated at 4° C. for 30 min. 15 μL of cMyc (9E10) Ac was added to the supernatant, and the mixture was rotated at 4° C. for 2 hr. The mixture was centrifuged at 12000 rpm for 10 sec, and the precipitate was washed 4 times with a buffer having NaCl (final 150 mM) and NP40 (final 0.05%) added. SDS sample buffer was added to beads and treated at 100° C. for 5 min, and Western blotting was performed.

4) Immunoprecipitation with an Endogenous Protein

Proteins were recovered from MG1.19 ES cells, and washed with the above described buffer. The NP40 were added to the buffer at 0.05% and the mixture was sonicated, and the supernatant was recovered. 5 μL of Normal mouse IgG Ac was added thereto, and the mixture was rotated at 4° C. for 30 min. 7.5 μl of normal anti-15-1 or 2 serum was added to the supernatant, and the mixture was rotated at 4° C. for 2 hr. 10 μl of Protein A-Sepharose was added thereto, and the mixture was rotated for 1 hr. The mixture was centrifuged at 12000 rpm for 10 sec, and washed 4 times with a buffer having NaCl (final 150 mM) and NP40 (final 0.05%) added. SDS sample buffer was added to beads and treated at 100° C. for 5 min, and the mixture was analyzed by Western blotting.

2. Results

Flag15-1 and Myc15-2 were forcedly expressed and immunoprecipitated with anti-Myc antibody, as a result, co-precipitation of Flag15-1 was detected (FIG. 5, left). Myc15-1 and Flag15-1 were forcedly expressed and immunoprecipitated with Myc, as a result, co-precipitation of Flag15-1 was detected (FIG. 5, middle). And, Myc15-2 and Flag15-2 were forcedly expressed and immunoprecipitated with Myc, as a result, co-precipitation of Flag15-2 was detected (FIG. 5, right). From these results, it is believed that ECAT15-1 and ECAT15-1, ECAT15-2 and ECAT15-2, and ECAT15-1 and ECAT15-2 bind each other within cells.

To investigate whether the above described results are true for endogenous proteins, immunoprecipitation was performed with antiserum. As a result, 15-1 and 15-2 were detected in immunoprecipitation with ani-15-1 antiserum. 15-1 and 15-2 could be also detected in immunoprecipitation with ani-15-2 antiserum (FIG. 6). From these results, it is believed that ECAT15-1 and ECAT15-2 bind each other within cells.

INDUSTRIAL APPLICABILITY

The present invention newly provides five kinds of ECAT genes (ECAT15-1 gene, ECAT15-2 gene, ECAT16 gene, Rnf17 gene, LOC380905 gene) specifically expressed in ES cells. The genes with ES cell-specific expression of the present invention and proteins encoded thereby are effectively used for the detection of ES cell, screening for a somatic cell nuclear reprogramming substance, screening for an ES cell maintaining substance and the like.

Sequence Listing Free Text

Figure 1:
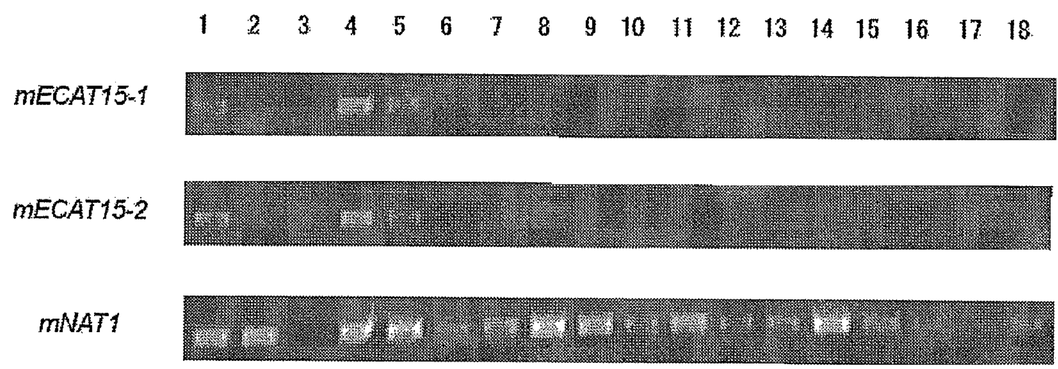
FIG. 1 shows the results of RT-PCT analysis of the expression of mECAT15-1 and mECAT15-2 in ES cells and 13 kinds of organs of adult mouse. As a positive control, the expression of mNAT1 was also analyzed. lane 1: undifferentiated MG1.19 ES cell, lane 2: differentiated MG1.19 ES cell, lane 3: undifferentiated RF8 ES cell (RT minus control), lane 4: undifferentiated RF8 ES cell, lane 5: differentiated RF8 ES cell, lane 6: brain, lane 7: heart, lane 8: kidney, lane 9: testis, lane 10: spleen, lane 11: muscle, lane 12: lung, lane 13: stomach, lane 14: ovary, lane 15: thymus, lane 16: liver, lane 17: skin, lane 18: intestine.
Figure 2:
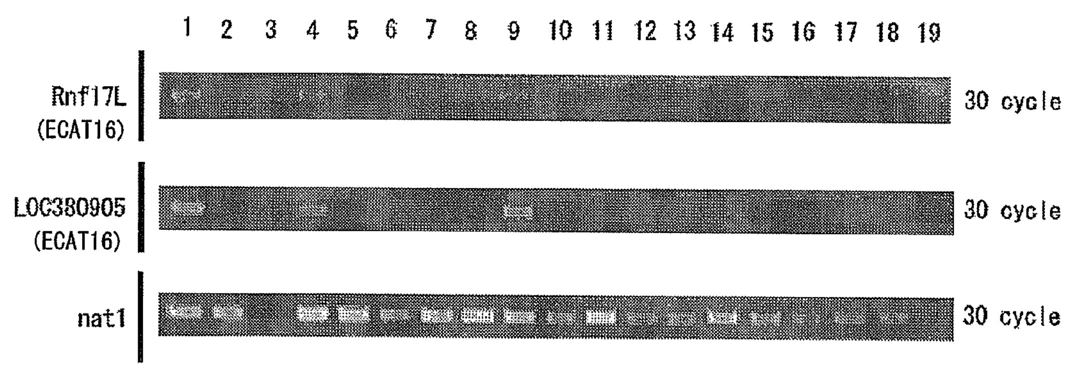
FIG. 2 shows the results of RT-PCT analysis of the expression of ECAT16 (mRnf17, LOC380905) in ES cells and 13 kinds of organs of adult mouse. As a positive control, the expression of mNAT1 was also analyzed. lane 1: undifferentiated MG1.19 ES cell, lane 2: differentiated MG1.19 ES cell, lane 3: undifferentiated RF8 ES cell (RT minus control), lane 4: undifferentiated RF8 ES cell, lane 5: differentiated RF8 ES cell, lane 6: brain, lane 7: heart, lane 8: kidney, lane 9: testis, lane 10: spleen, lane 11: muscle, lane 12: lung, lane 13: stomach, lane 14: ovary, lane 15: thymus, lane 16: liver, lane 17: skin, lane 18: intestine, lane 19: water (negative control).
Figure 3:
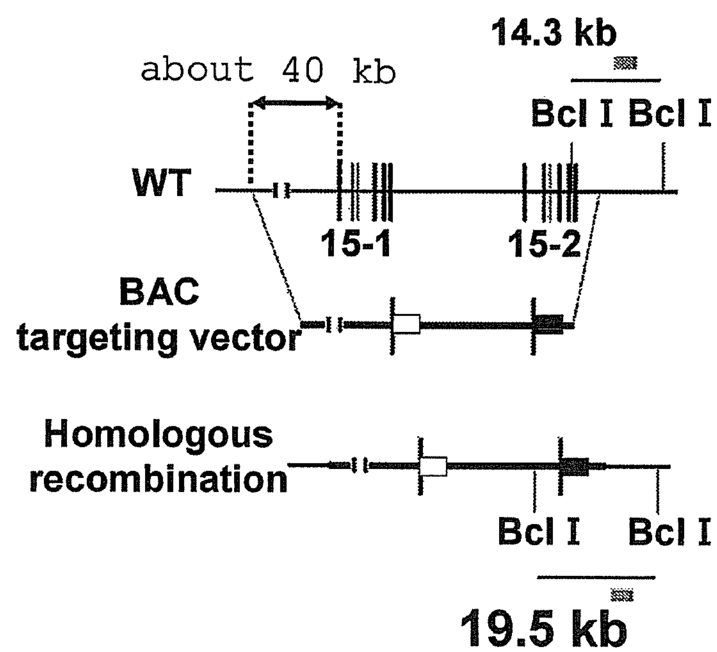
FIG. 3 shows the schematic diagram of the ECAT15 gene targeting vector, and destruction of ECAT15 gene using the same. In the Figure, the upper panel shows the positions of ECAT15-1 and ECAT15-2 genes on a wild-type genome, the middle panel shows the schematic diagram of the BAC targeting vector, and the lower panel shows the schematic diagram of the genome after homologous recombination. In the Figure, moreover, open squares show a neomycin resistance gene and black squares show a hygromycin resistance gene.
Figure 4:
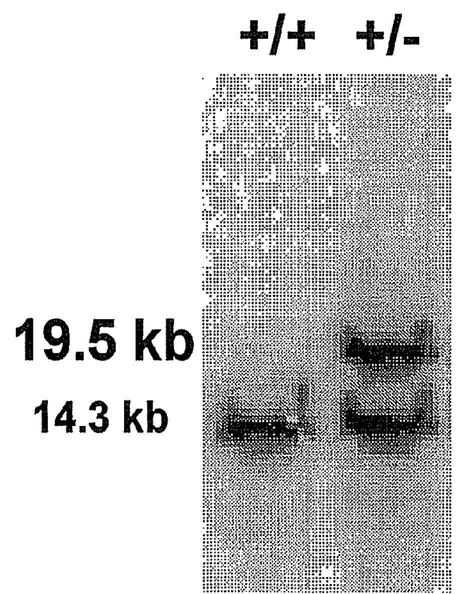
FIG. 4 shows the results of a Southern blot analysis confirming the homologous recombination of the ECAT15 gene. In the Figure, +/+ shows the results of a normal ES cell, and +/− shows the results of ECAT15 gene heterozygous mutant ES cell.
Figure 5:
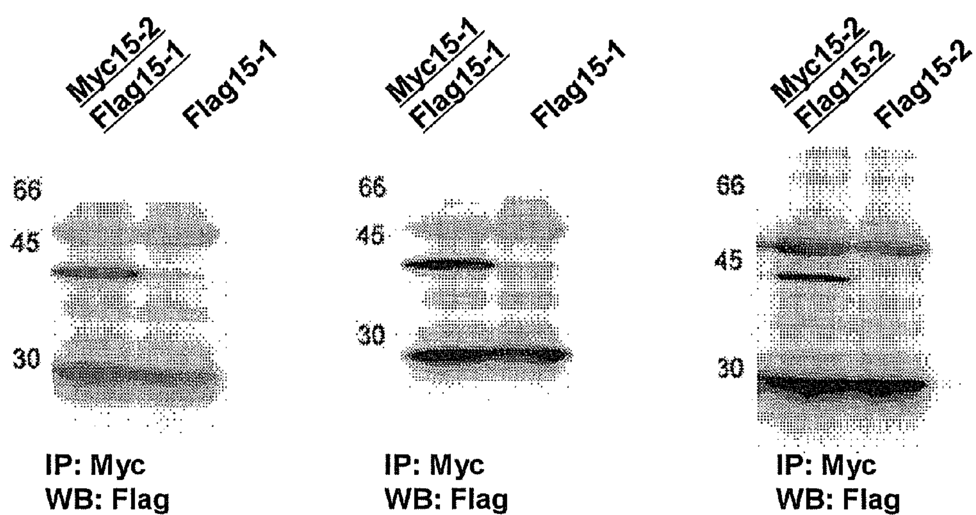
FIG. 5 shows formation of an ECAT15 protein complex. In the Figure, the left panel shows binding of ECAT15-1 and ECAT15-2, the middle panel shows binding of ECAT15-1 and ECAT15-1, and the right panel shows binding of ECAT15-2 and ECAT15-2. In the Figure, IP means immunoprecipitation, and WB means Western blot.
Figure 6:
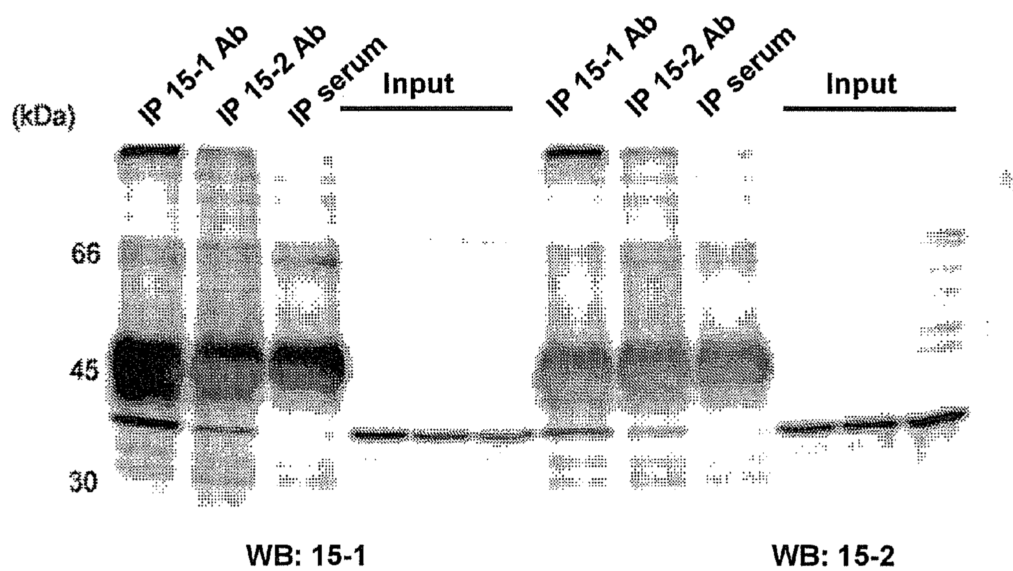
FIG. 6 shows formation of an ECAT15 protein (endogenous) complex. In the Figure, the left panel shows the results of immunoprecipitation with an anti-ECAT15-1 antibody, and the right panel shows the results of immunoprecipitation with an anti-ECAT15-2 antibody. In the Figure, moreover, Input shows the results of the cell extract before immunoprecipitation.

The base sequences shown in SEQ ID NO: 19-SEQ ID NO: 32 are primers.

The base sequences shown in SEQ ID NO: 35-SEQ ID NO: 48 are primers.

The base sequences shown in SEQ ID NO: 49-SEQ ID NO: 51 are probes.

The base sequences shown in SEQ ID NO: 52-SEQ ID NO: 55 are primers.

The invention claimed is:

1. An isolated polynucleotide selected from the group consisting of one of the following (a)-(c):

(a) a polynucleotide comprising SEQ ID NO: 17, (b) a polynucleotide having a homology of 95% or more with the polynucleotide of the aforementioned (a), which is specifically expressed in a mouse embryonic stem (ES) cell, and (c) a polynucleotide having a homology of 70% or more with the polynucleotide of the aforementioned (a), which is specifically expressed in a human ES cell.

2. A composition consisting of the following (a) and (b):

(a) a polynucleotide containing at least 15 contiguous bases of the polynucleotide of claim 1, wherein the at least 15 contiguous bases are identical to at least 15 contiguous bases of SEQ ID NO: 9, and (b) a polynucleotide containing at least 15 contiguous bases of the polynucleotide of claim 1, wherein the at least 15 contiguous bases are not identical to at least 15 contiguous bases of SEQ ID NO: 9.

3. The composition of claim 2, wherein the polynucleotides are a pair of primers.

* * * * *

SEQUENCE LISTING

```
<160> NUMBER OF SEQ ID NOS: 55

<210> SEQ ID NO 1
<211> LENGTH: 891
<212> TYPE: DNA
<213> ORGANISM: Mus musculus
<220> FEATURE:
<221> NAME/KEY: CDS
<222> LOCATION: (1)..(888)
```

```
<400> SEQUENCE: 1

atg gag act gct gga gac aag aag tgg agc gca gaa gag ccg aag gaa       48
Met Glu Thr Ala Gly Asp Lys Lys Trp Ser Ala Glu Glu Pro Lys Glu
1               5                   10                  15

gaa gtg gaa ttg cag atg tct agt caa cca agc acg gct cct gca aag       96
Glu Val Glu Leu Gln Met Ser Ser Gln Pro Ser Thr Ala Pro Ala Lys
            20                  25                  30

gct aaa gca acg ggg aaa aaa caa aag aag tcg gag aca gat aat ggt      144
Ala Lys Ala Thr Gly Lys Lys Gln Lys Lys Ser Glu Thr Asp Asn Gly
        35                  40                  45

tgt aaa cca aag gag gga aaa cca caa gac act gag acg cca gga cag      192
Cys Lys Pro Lys Glu Gly Lys Pro Gln Asp Thr Glu Thr Pro Gly Gln
    50                  55                  60

act cgt agg aag gta cca att cct cct att cca gag tat ctg ccc cca      240
Thr Arg Arg Lys Val Pro Ile Pro Pro Ile Pro Glu Tyr Leu Pro Pro
65                  70                  75                  80

gtg aac ctg att cac cga gat gtt ttg cgg gca tgg tgc cag aag aaa      288
Val Asn Leu Ile His Arg Asp Val Leu Arg Ala Trp Cys Gln Lys Lys
                85                  90                  95

cga gtg agc agc aaa ggc cag aaa tta gat gct tat aaa cga ctc ctt      336
Arg Val Ser Ser Lys Gly Gln Lys Leu Asp Ala Tyr Lys Arg Leu Leu
            100                 105                 110

gca agg gct ttc cca gaa caa atg ctg gag ttg agg aac gtc cct gac      384
Ala Arg Ala Phe Pro Glu Gln Met Leu Glu Leu Arg Asn Val Pro Asp
        115                 120                 125

tcg gcc aaa gac gcc agg ttg aag aca gct cac aaa aaa atg aag act      432
Ser Ala Lys Asp Ala Arg Leu Lys Thr Ala His Lys Lys Met Lys Thr
    130                 135                 140

gaa ccg ggg gag gag tct gag gtg aca gtt cct ctg gaa atg gtc cct      480
Glu Pro Gly Glu Glu Ser Glu Val Thr Val Pro Leu Glu Met Val Pro
145                 150                 155                 160

gtg cca gag gag cag ata cct gcc ctc att gac cct cct atg ctc tat      528
Val Pro Glu Glu Gln Ile Pro Ala Leu Ile Asp Pro Pro Met Leu Tyr
                165                 170                 175

gag gaa gtc agc acc acc gta gtg act aca cct gcc act gag gcc gtg      576
Glu Glu Val Ser Thr Thr Val Val Thr Thr Pro Ala Thr Glu Ala Val
            180                 185                 190

tta gca tct tgg gcc aga att gca tcc aat gct aag aag tac gag gca      624
Leu Ala Ser Trp Ala Arg Ile Ala Ser Asn Ala Lys Lys Tyr Glu Ala
        195                 200                 205

gtg cca gcc gat gct tcg tcc tca tca gaa gtc aaa ggg gaa atg tgg      672
Val Pro Ala Asp Ala Ser Ser Ser Ser Glu Val Lys Gly Glu Met Trp
    210                 215                 220

tgt gtg gtt cat ggg acc agc ctt cct ggg aac tcg cgt ggt tgg gtt      720
Cys Val Val His Gly Thr Ser Leu Pro Gly Asn Ser Arg Gly Trp Val
225                 230                 235                 240

cgg ctg cag ttc cac gct gga caa gcc tgg gta ccc gat aag aaa gga      768
Arg Leu Gln Phe His Ala Gly Gln Ala Trp Val Pro Asp Lys Lys Gly
                245                 250                 255

aaa gcc att gcc ctc ttc ctg ctt ccg gcc tgc aca ttt cca ccc cca      816
Lys Ala Ile Ala Leu Phe Leu Leu Pro Ala Cys Thr Phe Pro Pro Pro
            260                 265                 270

cac ctg gag gac aac atg ctg tgc ccc aag tgt gtt cat aag aac aag      864
His Leu Glu Asp Asn Met Leu Cys Pro Lys Cys Val His Lys Asn Lys
        275                 280                 285

atc ttg act aag agc ctc gaa gga taa                                  891
Ile Leu Thr Lys Ser Leu Glu Gly
    290                 295
```

<210> SEQ ID NO 2
<211> LENGTH: 296
<212> TYPE: PRT
<213> ORGANISM: Mus musculus

<400> SEQUENCE: 2

```
Met Glu Thr Ala Gly Asp Lys Lys Trp Ser Ala Glu Glu Pro Lys Glu
1               5                   10                  15

Glu Val Glu Leu Gln Met Ser Ser Gln Pro Ser Thr Ala Pro Ala Lys
            20                  25                  30

Ala Lys Ala Thr Gly Lys Lys Gln Lys Lys Ser Glu Thr Asp Asn Gly
        35                  40                  45

Cys Lys Pro Lys Glu Gly Lys Pro Gln Asp Thr Glu Thr Pro Gly Gln
    50                  55                  60

Thr Arg Arg Lys Val Pro Ile Pro Pro Ile Pro Glu Tyr Leu Pro Pro
65                  70                  75                  80

Val Asn Leu Ile His Arg Asp Val Leu Arg Ala Trp Cys Gln Lys Lys
                85                  90                  95

Arg Val Ser Ser Lys Gly Gln Lys Leu Asp Ala Tyr Lys Arg Leu Leu
            100                 105                 110

Ala Arg Ala Phe Pro Glu Gln Met Leu Glu Leu Arg Asn Val Pro Asp
        115                 120                 125

Ser Ala Lys Asp Ala Arg Leu Lys Thr Ala His Lys Lys Met Lys Thr
    130                 135                 140

Glu Pro Gly Glu Glu Ser Glu Val Thr Val Pro Leu Glu Met Val Pro
145                 150                 155                 160

Val Pro Glu Glu Gln Ile Pro Ala Leu Ile Asp Pro Pro Met Leu Tyr
                165                 170                 175

Glu Glu Val Ser Thr Thr Val Val Thr Thr Pro Ala Thr Glu Ala Val
            180                 185                 190

Leu Ala Ser Trp Ala Arg Ile Ala Ser Asn Ala Lys Lys Tyr Glu Ala
        195                 200                 205

Val Pro Ala Asp Ala Ser Ser Ser Ser Glu Val Lys Gly Glu Met Trp
    210                 215                 220

Cys Val Val His Gly Thr Ser Leu Pro Gly Asn Ser Arg Gly Trp Val
225                 230                 235                 240

Arg Leu Gln Phe His Ala Gly Gln Ala Trp Val Pro Asp Lys Lys Gly
                245                 250                 255

Lys Ala Ile Ala Leu Phe Leu Leu Pro Ala Cys Thr Phe Pro Pro Pro
            260                 265                 270

His Leu Glu Asp Asn Met Leu Cys Pro Lys Cys Val His Lys Asn Lys
        275                 280                 285

Ile Leu Thr Lys Ser Leu Glu Gly
    290                 295
```

<210> SEQ ID NO 3
<211> LENGTH: 885
<212> TYPE: DNA
<213> ORGANISM: Homo sapiens
<220> FEATURE:
<221> NAME/KEY: CDS
<222> LOCATION: (1)..(882)

<400> SEQUENCE: 3

```
atg gag aag gca aaa ggc aag gag tgg acc tcc aca gag aag tcg agg       48
Met Glu Lys Ala Lys Gly Lys Glu Trp Thr Ser Thr Glu Lys Ser Arg
1               5                   10                  15
```

```
gaa gag gat cag cag gct tct aat caa cca aat tca att gct ttg cca       96
Glu Glu Asp Gln Gln Ala Ser Asn Gln Pro Asn Ser Ile Ala Leu Pro
            20                  25                  30

gga aca tca gca aag aga acc aaa gaa aaa atg tct gtc aaa ggc agt      144
Gly Thr Ser Ala Lys Arg Thr Lys Glu Lys Met Ser Val Lys Gly Ser
        35                  40                  45

aaa gtg ctc tgc cct aag aaa aag gca gag cac act gac aac ccc aga      192
Lys Val Leu Cys Pro Lys Lys Lys Ala Glu His Thr Asp Asn Pro Arg
    50                  55                  60

cct cag aag aag ata cca atc cct cca tta cct tct aaa ctg cca cct      240
Pro Gln Lys Lys Ile Pro Ile Pro Pro Leu Pro Ser Lys Leu Pro Pro
65                  70                  75                  80

gtt aat ctg att cac cgg gac att ctg cgg gcc tgg tgc caa caa ttg      288
Val Asn Leu Ile His Arg Asp Ile Leu Arg Ala Trp Cys Gln Gln Leu
                85                  90                  95

aag ctg agc tcc aaa ggc cag aaa ttg gat gca tat aag cgc ctg tgt      336
Lys Leu Ser Ser Lys Gly Gln Lys Leu Asp Ala Tyr Lys Arg Leu Cys
            100                 105                 110

gcc ttt gcc tac cca aat caa aag gat ttt cct agc aca gca aaa gag      384
Ala Phe Ala Tyr Pro Asn Gln Lys Asp Phe Pro Ser Thr Ala Lys Glu
        115                 120                 125

gcc aaa atc cgg aaa tca ttg caa aaa aaa tta aag gtg gaa aag ggg      432
Ala Lys Ile Arg Lys Ser Leu Gln Lys Lys Leu Lys Val Glu Lys Gly
    130                 135                 140

gaa acg tcc ctg caa agt tct gag aca cat cct cct gaa gtg gct ctt      480
Glu Thr Ser Leu Gln Ser Ser Glu Thr His Pro Pro Glu Val Ala Leu
145                 150                 155                 160

cct cct gtg ggg gag ccg cct gcc ctg gaa aat tcc act gct ctc ctt      528
Pro Pro Val Gly Glu Pro Pro Ala Leu Glu Asn Ser Thr Ala Leu Leu
                165                 170                 175

gag gga gtt aat aca gtt gtg gtg aca act tct gcc cca gag gct ttg      576
Glu Gly Val Asn Thr Val Val Val Thr Thr Ser Ala Pro Glu Ala Leu
            180                 185                 190

ctg gcc tcc tgg gcg aga att tca gcc agg gcg agg aca cca gag gca      624
Leu Ala Ser Trp Ala Arg Ile Ser Ala Arg Ala Arg Thr Pro Glu Ala
        195                 200                 205

gtg gaa tct cca caa gag gcc tct ggt gtc agg tgg tgt gtg gtc cat      672
Val Glu Ser Pro Gln Glu Ala Ser Gly Val Arg Trp Cys Val Val His
    210                 215                 220

ggg aaa agt ctc cct gca gac aca gat ggt tgg gtt cac ctg cag ttt      720
Gly Lys Ser Leu Pro Ala Asp Thr Asp Gly Trp Val His Leu Gln Phe
225                 230                 235                 240

cat gct ggt caa gcc tgg gtt cca gaa aag caa gaa ggg aga gtg agt      768
His Ala Gly Gln Ala Trp Val Pro Glu Lys Gln Glu Gly Arg Val Ser
                245                 250                 255

gca ctc ttc ttg ctt cct gcc tcc aat ttt cca ccc ccg cac ctt gaa      816
Ala Leu Phe Leu Leu Pro Ala Ser Asn Phe Pro Pro Pro His Leu Glu
            260                 265                 270

gac aat atg ttg tgc ccc aaa tgt gtt cac agg aac aag gtc tta ata      864
Asp Asn Met Leu Cys Pro Lys Cys Val His Arg Asn Lys Val Leu Ile
        275                 280                 285

aaa agc ctc caa tgg gaa tag                                          885
Lys Ser Leu Gln Trp Glu
    290

<210> SEQ ID NO 4
<211> LENGTH: 294
<212> TYPE: PRT
<213> ORGANISM: Homo sapiens
```

```
<400> SEQUENCE: 4

Met Glu Lys Ala Lys Gly Lys Glu Trp Thr Ser Thr Glu Lys Ser Arg
1               5                   10                  15

Glu Glu Asp Gln Gln Ala Ser Asn Gln Pro Asn Ser Ile Ala Leu Pro
            20                  25                  30

Gly Thr Ser Ala Lys Arg Thr Lys Glu Lys Met Ser Val Lys Gly Ser
        35                  40                  45

Lys Val Leu Cys Pro Lys Lys Lys Ala Glu His Thr Asp Asn Pro Arg
    50                  55                  60

Pro Gln Lys Lys Ile Pro Ile Pro Pro Leu Pro Ser Lys Leu Pro Pro
65                  70                  75                  80

Val Asn Leu Ile His Arg Asp Ile Leu Arg Ala Trp Cys Gln Gln Leu
                85                  90                  95

Lys Leu Ser Ser Lys Gly Gln Lys Leu Asp Ala Tyr Lys Arg Leu Cys
            100                 105                 110

Ala Phe Ala Tyr Pro Asn Gln Lys Asp Phe Pro Ser Thr Ala Lys Glu
        115                 120                 125

Ala Lys Ile Arg Lys Ser Leu Gln Lys Lys Leu Lys Val Glu Lys Gly
    130                 135                 140

Glu Thr Ser Leu Gln Ser Ser Glu Thr His Pro Pro Glu Val Ala Leu
145                 150                 155                 160

Pro Pro Val Gly Glu Pro Pro Ala Leu Glu Asn Ser Thr Ala Leu Leu
                165                 170                 175

Glu Gly Val Asn Thr Val Val Val Thr Thr Ser Ala Pro Glu Ala Leu
            180                 185                 190

Leu Ala Ser Trp Ala Arg Ile Ser Ala Arg Ala Arg Thr Pro Glu Ala
        195                 200                 205

Val Glu Ser Pro Gln Glu Ala Ser Gly Val Arg Trp Cys Val Val His
    210                 215                 220

Gly Lys Ser Leu Pro Ala Asp Thr Asp Gly Trp Val His Leu Gln Phe
225                 230                 235                 240

His Ala Gly Gln Ala Trp Val Pro Glu Lys Gln Glu Gly Arg Val Ser
                245                 250                 255

Ala Leu Phe Leu Leu Pro Ala Ser Asn Phe Pro Pro Pro His Leu Glu
            260                 265                 270

Asp Asn Met Leu Cys Pro Lys Cys Val His Arg Asn Lys Val Leu Ile
        275                 280                 285

Lys Ser Leu Gln Trp Glu
    290


<210> SEQ ID NO 5
<211> LENGTH: 912
<212> TYPE: DNA
<213> ORGANISM: Mus musculus
<220> FEATURE:
<221> NAME/KEY: CDS
<222> LOCATION: (1)..(909)

<400> SEQUENCE: 5

atg tca tac ttc ggc ctg gag act ttc aac gag aac caa tct gag gag       48
Met Ser Tyr Phe Gly Leu Glu Thr Phe Asn Glu Asn Gln Ser Glu Glu
1               5                   10                  15

aac ttg gat gaa gaa agt gtg att tta acg ctg gtc ccc ttt aag gag       96
Asn Leu Asp Glu Glu Ser Val Ile Leu Thr Leu Val Pro Phe Lys Glu
            20                  25                  30

gag gag gag gag gag cca att aca gac tac cct acg caa tca aat gtt      144
```

-continued

```
Glu Glu Glu Glu Glu Pro Ile Thr Asp Tyr Pro Thr Gln Ser Asn Val
        35                  40                  45

tct tct tca acc tta gac cac aca cca cca gcc cgt tct ctg gtg agg      192
Ser Ser Ser Thr Leu Asp His Thr Pro Pro Ala Arg Ser Leu Val Arg
    50                  55                  60

cat gct gga atc aaa cac cca acc aga acc ata cca agc acc tgt cct      240
His Ala Gly Ile Lys His Pro Thr Arg Thr Ile Pro Ser Thr Cys Pro
65                  70                  75                  80

ccg ccc agc ctg cct cct att agg gac gtg tcc cgg aac act ctt cgg      288
Pro Pro Ser Leu Pro Pro Ile Arg Asp Val Ser Arg Asn Thr Leu Arg
                85                  90                  95

gag tgg tgt cgg tat cat aac ttg agt acg gat ggc aag aaa gtt gag      336
Glu Trp Cys Arg Tyr His Asn Leu Ser Thr Asp Gly Lys Lys Val Glu
            100                 105                 110

gtc tat ttg aga ctt cgg aga cac tcc tat tct aaa caa gaa tgt tat      384
Val Tyr Leu Arg Leu Arg Arg His Ser Tyr Ser Lys Gln Glu Cys Tyr
        115                 120                 125

att ccc aat aca tct cgg gag gcc aga atg aag cag ggt ccc aag aaa      432
Ile Pro Asn Thr Ser Arg Glu Ala Arg Met Lys Gln Gly Pro Lys Lys
    130                 135                 140

tcc aag ata gtc ttc aga gga atc ggg cct cca agc ggg tgc caa agg      480
Ser Lys Ile Val Phe Arg Gly Ile Gly Pro Pro Ser Gly Cys Gln Arg
145                 150                 155                 160

aga aaa gag gag agt ggt gtc ctg gaa att cta act tca cct aag gag      528
Arg Lys Glu Glu Ser Gly Val Leu Glu Ile Leu Thr Ser Pro Lys Glu
                165                 170                 175

tcc aca ttt gca gcc tgg gca agg att gcc atg aga gca gct cag tca      576
Ser Thr Phe Ala Ala Trp Ala Arg Ile Ala Met Arg Ala Ala Gln Ser
            180                 185                 190

atg tct aag aat cga tat cct ctt ccg tct aat gtg gag gcc ttt ctg      624
Met Ser Lys Asn Arg Tyr Pro Leu Pro Ser Asn Val Glu Ala Phe Leu
        195                 200                 205

cca caa gcc act gga tcc aga tgg tgt gtt gtc cat ggc agg cag ctc      672
Pro Gln Ala Thr Gly Ser Arg Trp Cys Val Val His Gly Arg Gln Leu
    210                 215                 220

cct gca gat aag aaa ggt tgg gtt cgc ctg caa ttt ctt gct gga cag      720
Pro Ala Asp Lys Lys Gly Trp Val Arg Leu Gln Phe Leu Ala Gly Gln
225                 230                 235                 240

acc tgg gtt cca gac act ccc caa agg atg aat ttt ctc ttc ctg tta      768
Thr Trp Val Pro Asp Thr Pro Gln Arg Met Asn Phe Leu Phe Leu Leu
                245                 250                 255

ccg gcc tgt att atc cca gaa cca gga gtg gaa gat aat ttg cta tgt      816
Pro Ala Cys Ile Ile Pro Glu Pro Gly Val Glu Asp Asn Leu Leu Cys
            260                 265                 270

cct gaa tgt gtt cac agc aac aag aag atc cta aga aac ttt aaa ata      864
Pro Glu Cys Val His Ser Asn Lys Lys Ile Leu Arg Asn Phe Lys Ile
        275                 280                 285

aga agc cgt gca aag aaa aat gcc cta ccc cca aat atg ccg ccg tag      912
Arg Ser Arg Ala Lys Lys Asn Ala Leu Pro Pro Asn Met Pro Pro
    290                 295                 300
```

```
<210> SEQ ID NO 6
<211> LENGTH: 303
<212> TYPE: PRT
<213> ORGANISM: Mus musculus

<400> SEQUENCE: 6

Met Ser Tyr Phe Gly Leu Glu Thr Phe Asn Glu Asn Gln Ser Glu Glu
1               5                   10                  15

Asn Leu Asp Glu Glu Ser Val Ile Leu Thr Leu Val Pro Phe Lys Glu
```

-continued

```
            20                  25                  30

Glu Glu Glu Glu Glu Pro Ile Thr Asp Tyr Pro Thr Gln Ser Asn Val
        35                  40                  45

Ser Ser Ser Thr Leu Asp His Thr Pro Pro Ala Arg Ser Leu Val Arg
    50                  55                  60

His Ala Gly Ile Lys His Pro Thr Arg Thr Ile Pro Ser Thr Cys Pro
65                  70                  75                  80

Pro Pro Ser Leu Pro Pro Ile Arg Asp Val Ser Arg Asn Thr Leu Arg
                85                  90                  95

Glu Trp Cys Arg Tyr His Asn Leu Ser Thr Asp Gly Lys Lys Val Glu
            100                 105                 110

Val Tyr Leu Arg Leu Arg Arg His Ser Tyr Ser Lys Gln Glu Cys Tyr
        115                 120                 125

Ile Pro Asn Thr Ser Arg Glu Ala Arg Met Lys Gln Gly Pro Lys Lys
    130                 135                 140

Ser Lys Ile Val Phe Arg Gly Ile Gly Pro Pro Ser Gly Cys Gln Arg
145                 150                 155                 160

Arg Lys Glu Glu Ser Gly Val Leu Glu Ile Leu Thr Ser Pro Lys Glu
                165                 170                 175

Ser Thr Phe Ala Ala Trp Ala Arg Ile Ala Met Arg Ala Ala Gln Ser
            180                 185                 190

Met Ser Lys Asn Arg Tyr Pro Leu Pro Ser Asn Val Glu Ala Phe Leu
        195                 200                 205

Pro Gln Ala Thr Gly Ser Arg Trp Cys Val Val His Gly Arg Gln Leu
    210                 215                 220

Pro Ala Asp Lys Lys Gly Trp Val Arg Leu Gln Phe Leu Ala Gly Gln
225                 230                 235                 240

Thr Trp Val Pro Asp Thr Pro Gln Arg Met Asn Phe Leu Phe Leu Leu
                245                 250                 255

Pro Ala Cys Ile Ile Pro Glu Pro Gly Val Glu Asp Asn Leu Leu Cys
            260                 265                 270

Pro Glu Cys Val His Ser Asn Lys Lys Ile Leu Arg Asn Phe Lys Ile
        275                 280                 285

Arg Ser Arg Ala Lys Lys Asn Ala Leu Pro Pro Asn Met Pro Pro
    290                 295                 300


<210> SEQ ID NO 7
<211> LENGTH: 897
<212> TYPE: DNA
<213> ORGANISM: Homo sapiens
<220> FEATURE:
<221> NAME/KEY: CDS
<222> LOCATION: (1)..(894)

<400> SEQUENCE: 7

atg tca gat gca aat ttg gat agc agc aag aag aat ttc ttg gag ggg       48
Met Ser Asp Ala Asn Leu Asp Ser Ser Lys Lys Asn Phe Leu Glu Gly
1               5                   10                  15

gaa gta gat gat gag gaa agt gtg att ttg aca ctg gtg cca gtt aaa       96
Glu Val Asp Asp Glu Glu Ser Val Ile Leu Thr Leu Val Pro Val Lys
            20                  25                  30

gat gac gca aat atg gaa caa atg gaa cca agc gtt tct tca act tct      144
Asp Asp Ala Asn Met Glu Gln Met Glu Pro Ser Val Ser Ser Thr Ser
        35                  40                  45

gat gtc aaa ctg gag aag cct aag aaa tac aat cca ggt cat cta ctt      192
Asp Val Lys Leu Glu Lys Pro Lys Lys Tyr Asn Pro Gly His Leu Leu
    50                  55                  60
```

```
caa aca aat gag caa ttt aca gct cca caa aaa gct aga tgc aaa ata      240
Gln Thr Asn Glu Gln Phe Thr Ala Pro Gln Lys Ala Arg Cys Lys Ile
65                  70                  75                  80

cca gcc ctt ccc ttg ccg acc att tcg cct ccc att aat aag gtg tgt      288
Pro Ala Leu Pro Leu Pro Thr Ile Ser Pro Pro Ile Asn Lys Val Cys
                85                  90                  95

cgg gac act ttg cgg gac tgg tgt caa caa ctc ggt ttg agt act aat      336
Arg Asp Thr Leu Arg Asp Trp Cys Gln Gln Leu Gly Leu Ser Thr Asn
            100                 105                 110

ggc aag aaa atc gaa gtt tat ctg agg ctt cat agg cat gct tac cct      384
Gly Lys Lys Ile Glu Val Tyr Leu Arg Leu His Arg His Ala Tyr Pro
        115                 120                 125

gaa caa cgg caa gat atg cct gaa atg tca caa gag acc aga tta cag      432
Glu Gln Arg Gln Asp Met Pro Glu Met Ser Gln Glu Thr Arg Leu Gln
    130                 135                 140

cga tgt tcg agg aaa cgc aag gca gtg acc aag aga gca agg ctt cag      480
Arg Cys Ser Arg Lys Arg Lys Ala Val Thr Lys Arg Ala Arg Leu Gln
145                 150                 155                 160

aga agt tat gag atg aat gag aga gca gaa gag acc aat aca gtc gaa      528
Arg Ser Tyr Glu Met Asn Glu Arg Ala Glu Glu Thr Asn Thr Val Glu
                165                 170                 175

gtg ata act tca gca ccg gga gcc atg ttg gca tca tgg gca aga att      576
Val Ile Thr Ser Ala Pro Gly Ala Met Leu Ala Ser Trp Ala Arg Ile
            180                 185                 190

gct gca aga gct gtt cag cct aag gct ttg aat tca tgt tcc att ccc      624
Ala Ala Arg Ala Val Gln Pro Lys Ala Leu Asn Ser Cys Ser Ile Pro
        195                 200                 205

gtt tct gtt gag gcc ttt ttg atg caa gcc tct ggc gtc agg tgg tgt      672
Val Ser Val Glu Ala Phe Leu Met Gln Ala Ser Gly Val Arg Trp Cys
    210                 215                 220

gtg gtc cat ggc aga ctt ctc tcg gca gac aca aag ggt tgg gta cgc      720
Val Val His Gly Arg Leu Leu Ser Ala Asp Thr Lys Gly Trp Val Arg
225                 230                 235                 240

ctg cag ttt cat gca ggt cag gcc tgg gtg cct acc act cac agg agg      768
Leu Gln Phe His Ala Gly Gln Ala Trp Val Pro Thr Thr His Arg Arg
                245                 250                 255

atg att tct ctc ttc ttg tta cct gcc tgc att ttc cca tcc cca ggc      816
Met Ile Ser Leu Phe Leu Leu Pro Ala Cys Ile Phe Pro Ser Pro Gly
            260                 265                 270

ata gaa gat aat atg tta tgc ccc gac tgt gct aag agg aat aag aag      864
Ile Glu Asp Asn Met Leu Cys Pro Asp Cys Ala Lys Arg Asn Lys Lys
        275                 280                 285

atg atg aaa aga tta atg aca gta gag aag tag                          897
Met Met Lys Arg Leu Met Thr Val Glu Lys
    290                 295
```

```
<210> SEQ ID NO 8
<211> LENGTH: 298
<212> TYPE: PRT
<213> ORGANISM: Homo sapiens

<400> SEQUENCE: 8

Met Ser Asp Ala Asn Leu Asp Ser Ser Lys Lys Asn Phe Leu Glu Gly
1               5                   10                  15

Glu Val Asp Asp Glu Glu Ser Val Ile Leu Thr Leu Val Pro Val Lys
            20                  25                  30

Asp Asp Ala Asn Met Glu Gln Met Glu Pro Ser Val Ser Ser Thr Ser
        35                  40                  45

Asp Val Lys Leu Glu Lys Pro Lys Lys Tyr Asn Pro Gly His Leu Leu
```

```
    50                  55                  60

Gln Thr Asn Glu Gln Phe Thr Ala Pro Gln Lys Ala Arg Cys Lys Ile
65                  70                  75                  80

Pro Ala Leu Pro Leu Pro Thr Ile Ser Pro Pro Ile Asn Lys Val Cys
                85                  90                  95

Arg Asp Thr Leu Arg Asp Trp Cys Gln Gln Leu Gly Leu Ser Thr Asn
            100                 105                 110

Gly Lys Lys Ile Glu Val Tyr Leu Arg Leu His Arg His Ala Tyr Pro
        115                 120                 125

Glu Gln Arg Gln Asp Met Pro Glu Met Ser Gln Glu Thr Arg Leu Gln
    130                 135                 140

Arg Cys Ser Arg Lys Arg Lys Ala Val Thr Lys Arg Ala Arg Leu Gln
145                 150                 155                 160

Arg Ser Tyr Glu Met Asn Glu Arg Ala Glu Glu Thr Asn Thr Val Glu
                165                 170                 175

Val Ile Thr Ser Ala Pro Gly Ala Met Leu Ala Ser Trp Ala Arg Ile
            180                 185                 190

Ala Ala Arg Ala Val Gln Pro Lys Ala Leu Asn Ser Cys Ser Ile Pro
        195                 200                 205

Val Ser Val Glu Ala Phe Leu Met Gln Ala Ser Gly Val Arg Trp Cys
    210                 215                 220

Val Val His Gly Arg Leu Leu Ser Ala Asp Thr Lys Gly Trp Val Arg
225                 230                 235                 240

Leu Gln Phe His Ala Gly Gln Ala Trp Val Pro Thr Thr His Arg Arg
                245                 250                 255

Met Ile Ser Leu Phe Leu Leu Pro Ala Cys Ile Phe Pro Ser Pro Gly
            260                 265                 270

Ile Glu Asp Asn Met Leu Cys Pro Asp Cys Ala Lys Arg Asn Lys Lys
        275                 280                 285

Met Met Lys Arg Leu Met Thr Val Glu Lys
    290                 295


<210> SEQ ID NO 9
<211> LENGTH: 2094
<212> TYPE: DNA
<213> ORGANISM: Mus musculus
<220> FEATURE:
<221> NAME/KEY: CDS
<222> LOCATION: (5)..(1885)

<400> SEQUENCE: 9

agca atg gcg gca gag gct tcg tcg acc ggg ctg gct tcc tgt cac cta      49
     Met Ala Ala Glu Ala Ser Ser Thr Gly Leu Ala Ser Cys His Leu
     1               5                   10                  15

gtg gag agt aag agt gga gcg cag ggt gcc tcg ggg tgt cag tgc act       97
Val Glu Ser Lys Ser Gly Ala Gln Gly Ala Ser Gly Cys Gln Cys Thr
                20                  25                  30

cgg tgt gga agg aag gtg tcc gtt gcc tcc ggt gac cac cac aag ttt      145
Arg Cys Gly Arg Lys Val Ser Val Ala Ser Gly Asp His His Lys Phe
            35                  40                  45

cca tgt gga cat gcc ttt tgt gaa ctg tgc ctg tca gca cct caa gaa      193
Pro Cys Gly His Ala Phe Cys Glu Leu Cys Leu Ser Ala Pro Gln Glu
        50                  55                  60

tat acc aca agt aaa tgc act gac tgt gag gtt cat aca act gtc agc      241
Tyr Thr Thr Ser Lys Cys Thr Asp Cys Glu Val His Thr Thr Val Ser
    65                  70                  75

atg aat caa ggt cac tac cca gta gat ggc ttc atc gag gaa gat tct      289
```

-continued

```
Met Asn Gln Gly His Tyr Pro Val Asp Gly Phe Ile Glu Glu Asp Ser
80                  85                  90                  95

tct ctg gaa gcc ttg cca ccg aaa atg gta aat aac tgc tct tca gat     337
Ser Leu Glu Ala Leu Pro Pro Lys Met Val Asn Asn Cys Ser Ser Asp
                100                 105                 110

ctt gaa aag aca gtg gac cag cta att aat gat tta gaa cat tca tcc     385
Leu Glu Lys Thr Val Asp Gln Leu Ile Asn Asp Leu Glu His Ser Ser
            115                 120                 125

tcc ata cat agg aat gtt tca aac cca tca gct gta atg tcg gag aca     433
Ser Ile His Arg Asn Val Ser Asn Pro Ser Ala Val Met Ser Glu Thr
        130                 135                 140

gaa gaa att gat gaa gca ctg aag ata gca ggc tgt aat ttt gaa caa     481
Glu Glu Ile Asp Glu Ala Leu Lys Ile Ala Gly Cys Asn Phe Glu Gln
    145                 150                 155

tta agt aat gct ata aaa atg ctt gat agc aca caa gat caa aca aga     529
Leu Ser Asn Ala Ile Lys Met Leu Asp Ser Thr Gln Asp Gln Thr Arg
160                 165                 170                 175

caa gag aca cac agt cta aca gag gct gtg gag aaa cag ttt gat aca     577
Gln Glu Thr His Ser Leu Thr Glu Ala Val Glu Lys Gln Phe Asp Thr
                180                 185                 190

ctt ctt gct tct ctt gat tcc agg aaa aag agc ttg tgt gaa gaa ctt     625
Leu Leu Ala Ser Leu Asp Ser Arg Lys Lys Ser Leu Cys Glu Glu Leu
            195                 200                 205

ata agg cgt aca gat gat tat tta tca aaa tta gta aca gtt aaa agc     673
Ile Arg Arg Thr Asp Asp Tyr Leu Ser Lys Leu Val Thr Val Lys Ser
        210                 215                 220

tac att gaa gag aaa aaa agt gat ttg gat gca gct atg aag ata gca     721
Tyr Ile Glu Glu Lys Lys Ser Asp Leu Asp Ala Ala Met Lys Ile Ala
    225                 230                 235

aaa gaa ctc aga tct gct cct tct ctg agg acc tac tgt gac ctg act     769
Lys Glu Leu Arg Ser Ala Pro Ser Leu Arg Thr Tyr Cys Asp Leu Thr
240                 245                 250                 255

cag att atc cgg act ttg aag tta aca ttt gaa agt gaa ttg tca caa     817
Gln Ile Ile Arg Thr Leu Lys Leu Thr Phe Glu Ser Glu Leu Ser Gln
                260                 265                 270

gtt agt tcc ata att cca agg aac acc cct agg ttg gat ata aat tgc     865
Val Ser Ser Ile Ile Pro Arg Asn Thr Pro Arg Leu Asp Ile Asn Cys
            275                 280                 285

agt gag gcc atc tgc atg ttc agc agt atg gga aag att gaa ttt gag     913
Ser Glu Ala Ile Cys Met Phe Ser Ser Met Gly Lys Ile Glu Phe Glu
        290                 295                 300

gac tca aca aaa tgt tac cct caa gaa aat gaa gat gga cag aat gtt     961
Asp Ser Thr Lys Cys Tyr Pro Gln Glu Asn Glu Asp Gly Gln Asn Val
    305                 310                 315

caa aag aaa ttt aat aat aga aag gaa ctc tgt tgt gat gta tac tca    1009
Gln Lys Lys Phe Asn Asn Arg Lys Glu Leu Cys Cys Asp Val Tyr Ser
320                 325                 330                 335

tca cta gaa aag aaa aag gta gat gct gct gtc ctg act gat gaa aca    1057
Ser Leu Glu Lys Lys Lys Val Asp Ala Ala Val Leu Thr Asp Glu Thr
                340                 345                 350

cct gaa cct cct ttg caa gca gag gcc cct gac agg cat tta gaa ggg    1105
Pro Glu Pro Pro Leu Gln Ala Glu Ala Pro Asp Arg His Leu Glu Gly
            355                 360                 365

aaa aag aag cag cca aca aaa gag atg gtt gtg gtg aca tct cct aag    1153
Lys Lys Lys Gln Pro Thr Lys Glu Met Val Val Val Thr Ser Pro Lys
        370                 375                 380

act att gct gta ctg cct caa ctg gga tcc agc cct gat gtg ata att    1201
Thr Ile Ala Val Leu Pro Gln Leu Gly Ser Ser Pro Asp Val Ile Ile
    385                 390                 395
```

-continued

```
gag gaa att att gag gaa aac cta gaa tca tgc ttt aca gat gat cct      1249
Glu Glu Ile Ile Glu Glu Asn Leu Glu Ser Cys Phe Thr Asp Asp Pro
400                 405                 410                 415

ata gag act tct gga tac cca aaa aag ccc cct cag aaa gag cag tct      1297
Ile Glu Thr Ser Gly Tyr Pro Lys Lys Pro Pro Gln Lys Glu Gln Ser
                420                 425                 430

gct cct gtt gga tca aaa gca ggt tgt cca gag cta gtt ttt gta agt      1345
Ala Pro Val Gly Ser Lys Ala Gly Cys Pro Glu Leu Val Phe Val Ser
            435                 440                 445

cat gta ata cat cct tgc cac ttc tat gtg cgg aaa tat tca caa ata      1393
His Val Ile His Pro Cys His Phe Tyr Val Arg Lys Tyr Ser Gln Ile
        450                 455                 460

aaa gat gca aca ata ttg gag aag aag atg aag caa gtt tgc aat agg      1441
Lys Asp Ala Thr Ile Leu Glu Lys Lys Met Lys Gln Val Cys Asn Arg
    465                 470                 475

agc tta cac ctt gat cct tca gac att ttg gaa cta ggt gca aga ata      1489
Ser Leu His Leu Asp Pro Ser Asp Ile Leu Glu Leu Gly Ala Arg Ile
480                 485                 490                 495

ttt gtc aac agt att aag aat aga atg tgg tgt cga gga att atc act      1537
Phe Val Asn Ser Ile Lys Asn Arg Met Trp Cys Arg Gly Ile Ile Thr
                500                 505                 510

gaa ata att cca tca aaa act aaa aat att aga aaa cca tgt agt cca      1585
Glu Ile Ile Pro Ser Lys Thr Lys Asn Ile Arg Lys Pro Cys Ser Pro
            515                 520                 525

acc aaa ttc tca gtc tgt gaa att tca cta ata cag ata ttc atg gta      1633
Thr Lys Phe Ser Val Cys Glu Ile Ser Leu Ile Gln Ile Phe Met Val
        530                 535                 540

gat ttt gga aat tct gaa gtc ctg atc atc aca gga gtt ggt gac aca      1681
Asp Phe Gly Asn Ser Glu Val Leu Ile Ile Thr Gly Val Gly Asp Thr
    545                 550                 555

cat gag gga cca gag cat gat ggt gaa cag cat att aca cta agt gac      1729
His Glu Gly Pro Glu His Asp Gly Glu Gln His Ile Thr Leu Ser Asp
560                 565                 570                 575

ttc tgt ctg ctt cta atg aag tct gaa cca tac agt gag gaa ctg ttg      1777
Phe Cys Leu Leu Leu Met Lys Ser Glu Pro Tyr Ser Glu Glu Leu Leu
                580                 585                 590

aaa gac atc cca cat tta gca cac ctg tgc tcc ttg aaa gac atc gtc      1825
Lys Asp Ile Pro His Leu Ala His Leu Cys Ser Leu Lys Asp Ile Val
            595                 600                 605

cca tac aat tca gta agt gag aga gaa agt gat tct ccc tca aag gct      1873
Pro Tyr Asn Ser Val Ser Glu Arg Glu Ser Asp Ser Pro Ser Lys Ala
        610                 615                 620

gtg gag ttt tag ttgtgttgcc agtgaagttg ctgagttggt ctgaaagaac         1925
Val Glu Phe
    625

cagttagcct tgacaaacac attctgatta tgaactatta gtgccaataa aagttgccat   1985

aagcctcagc ttccataact gaaaatattt gtaatgaaaa tttgagctca ataaagttca   2045

tatgaacata ataaaatatt caagtaaata ccacaaaaaa aaaaaaaaa               2094


<210> SEQ ID NO 10
<211> LENGTH: 626
<212> TYPE: PRT
<213> ORGANISM: Mus musculus

<400> SEQUENCE: 10

Met Ala Ala Glu Ala Ser Ser Thr Gly Leu Ala Ser Cys His Leu Val
1               5                   10                  15

Glu Ser Lys Ser Gly Ala Gln Gly Ala Ser Gly Cys Gln Cys Thr Arg
            20                  25                  30
```

-continued

```
Cys Gly Arg Lys Val Ser Val Ala Ser Gly Asp His His Lys Phe Pro
        35                  40                  45

Cys Gly His Ala Phe Cys Glu Leu Cys Leu Ser Ala Pro Gln Glu Tyr
    50                  55                  60

Thr Thr Ser Lys Cys Thr Asp Cys Glu Val His Thr Thr Val Ser Met
65                  70                  75                  80

Asn Gln Gly His Tyr Pro Val Asp Gly Phe Ile Glu Glu Asp Ser Ser
                85                  90                  95

Leu Glu Ala Leu Pro Pro Lys Met Val Asn Asn Cys Ser Ser Asp Leu
            100                 105                 110

Glu Lys Thr Val Asp Gln Leu Ile Asn Asp Leu Glu His Ser Ser Ser
        115                 120                 125

Ile His Arg Asn Val Ser Asn Pro Ser Ala Val Met Ser Glu Thr Glu
    130                 135                 140

Glu Ile Asp Glu Ala Leu Lys Ile Ala Gly Cys Asn Phe Glu Gln Leu
145                 150                 155                 160

Ser Asn Ala Ile Lys Met Leu Asp Ser Thr Gln Asp Gln Thr Arg Gln
                165                 170                 175

Glu Thr His Ser Leu Thr Glu Ala Val Glu Lys Gln Phe Asp Thr Leu
            180                 185                 190

Leu Ala Ser Leu Asp Ser Arg Lys Lys Ser Leu Cys Glu Glu Leu Ile
        195                 200                 205

Arg Arg Thr Asp Asp Tyr Leu Ser Lys Leu Val Thr Val Lys Ser Tyr
    210                 215                 220

Ile Glu Glu Lys Lys Ser Asp Leu Asp Ala Ala Met Lys Ile Ala Lys
225                 230                 235                 240

Glu Leu Arg Ser Ala Pro Ser Leu Arg Thr Tyr Cys Asp Leu Thr Gln
                245                 250                 255

Ile Ile Arg Thr Leu Lys Leu Thr Phe Glu Ser Glu Leu Ser Gln Val
            260                 265                 270

Ser Ser Ile Ile Pro Arg Asn Thr Pro Arg Leu Asp Ile Asn Cys Ser
        275                 280                 285

Glu Ala Ile Cys Met Phe Ser Ser Met Gly Lys Ile Glu Phe Glu Asp
    290                 295                 300

Ser Thr Lys Cys Tyr Pro Gln Glu Asn Glu Asp Gly Gln Asn Val Gln
305                 310                 315                 320

Lys Lys Phe Asn Asn Arg Lys Glu Leu Cys Cys Asp Val Tyr Ser Ser
                325                 330                 335

Leu Glu Lys Lys Lys Val Asp Ala Ala Val Leu Thr Asp Glu Thr Pro
            340                 345                 350

Glu Pro Pro Leu Gln Ala Glu Ala Pro Asp Arg His Leu Glu Gly Lys
        355                 360                 365

Lys Lys Gln Pro Thr Lys Glu Met Val Val Val Thr Ser Pro Lys Thr
    370                 375                 380

Ile Ala Val Leu Pro Gln Leu Gly Ser Ser Pro Asp Val Ile Ile Glu
385                 390                 395                 400

Glu Ile Ile Glu Glu Asn Leu Glu Ser Cys Phe Thr Asp Asp Pro Ile
                405                 410                 415

Glu Thr Ser Gly Tyr Pro Lys Lys Pro Pro Gln Lys Glu Gln Ser Ala
            420                 425                 430

Pro Val Gly Ser Lys Ala Gly Cys Pro Glu Leu Val Phe Val Ser His
        435                 440                 445
```

-continued

```
Val Ile His Pro Cys His Phe Tyr Val Arg Lys Tyr Ser Gln Ile Lys
    450                 455                 460

Asp Ala Thr Ile Leu Glu Lys Lys Met Lys Gln Val Cys Asn Arg Ser
465                 470                 475                 480

Leu His Leu Asp Pro Ser Asp Ile Leu Glu Leu Gly Ala Arg Ile Phe
                485                 490                 495

Val Asn Ser Ile Lys Asn Arg Met Trp Cys Arg Gly Ile Ile Thr Glu
            500                 505                 510

Ile Ile Pro Ser Lys Thr Lys Asn Ile Arg Lys Pro Cys Ser Pro Thr
        515                 520                 525

Lys Phe Ser Val Cys Glu Ile Ser Leu Ile Gln Ile Phe Met Val Asp
    530                 535                 540

Phe Gly Asn Ser Glu Val Leu Ile Ile Thr Gly Val Gly Asp Thr His
545                 550                 555                 560

Glu Gly Pro Glu His Asp Gly Glu Gln His Ile Thr Leu Ser Asp Phe
                565                 570                 575

Cys Leu Leu Leu Met Lys Ser Glu Pro Tyr Ser Glu Glu Leu Leu Lys
            580                 585                 590

Asp Ile Pro His Leu Ala His Leu Cys Ser Leu Lys Asp Ile Val Pro
        595                 600                 605

Tyr Asn Ser Val Ser Glu Arg Glu Ser Asp Ser Pro Ser Lys Ala Val
    610                 615                 620

Glu Phe
625


<210> SEQ ID NO 11
<211> LENGTH: 2149
<212> TYPE: DNA
<213> ORGANISM: Homo sapiens
<220> FEATURE:
<221> NAME/KEY: CDS
<222> LOCATION: (6)..(1967)

<400> SEQUENCE: 11

gggcg atg gcg gca gag gct tcg aag act ggg cct tct agg tct tcc tac      50
      Met Ala Ala Glu Ala Ser Lys Thr Gly Pro Ser Arg Ser Ser Tyr
      1               5                   10                  15

cag cga atg ggg agg aag agt cag ccc tgg ggt gcc gct gaa atc cag        98
Gln Arg Met Gly Arg Lys Ser Gln Pro Trp Gly Ala Ala Glu Ile Gln
                20                  25                  30

tgc acc agg tgt gga agg agg gta tcc aga tca tcc ggt cac cat tgt       146
Cys Thr Arg Cys Gly Arg Arg Val Ser Arg Ser Ser Gly His His Cys
            35                  40                  45

gaa ctt caa tgt gga cat gct ttt tgt gaa cta tgc ttg tta atg act       194
Glu Leu Gln Cys Gly His Ala Phe Cys Glu Leu Cys Leu Leu Met Thr
        50                  55                  60

gaa gaa tgc acc aca att ata tgc cct gat tgt gag gtt gct aca gct       242
Glu Glu Cys Thr Thr Ile Ile Cys Pro Asp Cys Glu Val Ala Thr Ala
    65                  70                  75

gta aat act aga caa cgc tac tac cca atg gct gga tat att aag gaa       290
Val Asn Thr Arg Gln Arg Tyr Tyr Pro Met Ala Gly Tyr Ile Lys Glu
80                  85                  90                  95

gac tcc ata atg gaa aaa ctg cag cct aag acg ata aag aat tgt tct       338
Asp Ser Ile Met Glu Lys Leu Gln Pro Lys Thr Ile Lys Asn Cys Ser
                100                 105                 110

cag gac ttt aag aag act gct gat cag cta act act ggt tta gaa cgt       386
Gln Asp Phe Lys Lys Thr Ala Asp Gln Leu Thr Thr Gly Leu Glu Arg
            115                 120                 125
```

-continued

```
tca gcc tcc aca gac aag act ctt ttg aac tca tca gct gta atg ttg      434
Ser Ala Ser Thr Asp Lys Thr Leu Leu Asn Ser Ser Ala Val Met Leu
        130                 135                 140

gac act aat act gca gaa gaa att gat gaa gca ttg aat aca gca cac      482
Asp Thr Asn Thr Ala Glu Glu Ile Asp Glu Ala Leu Asn Thr Ala His
    145                 150                 155

cat agt ttc gaa cag tta agc att gct gga aaa gca ctt gaa cac atg      530
His Ser Phe Glu Gln Leu Ser Ile Ala Gly Lys Ala Leu Glu His Met
160                 165                 170                 175

cag aag caa acg ata gag gaa aga gaa aga gtt ata gaa gtt gtg gag      578
Gln Lys Gln Thr Ile Glu Glu Arg Glu Arg Val Ile Glu Val Val Glu
                180                 185                 190

aaa cag ttt gac caa ctt ttg gct ttt ttt gat tcc agg aaa aag aac      626
Lys Gln Phe Asp Gln Leu Leu Ala Phe Phe Asp Ser Arg Lys Lys Asn
            195                 200                 205

ctg tgt gaa gaa ttt gca aga act act gat gat tat cta tca aat tta      674
Leu Cys Glu Glu Phe Ala Arg Thr Thr Asp Asp Tyr Leu Ser Asn Leu
        210                 215                 220

ata aag gct aaa agc tac att gaa gag aaa aaa aat aat ttg aat gca      722
Ile Lys Ala Lys Ser Tyr Ile Glu Glu Lys Lys Asn Asn Leu Asn Ala
    225                 230                 235

gct atg aac ata gca aga gca tta caa tta tcg cct tct cta aga aca      770
Ala Met Asn Ile Ala Arg Ala Leu Gln Leu Ser Pro Ser Leu Arg Thr
240                 245                 250                 255

tac tgt gac ctg aat cag att atc cgg act ttg cag tta act tca gat      818
Tyr Cys Asp Leu Asn Gln Ile Ile Arg Thr Leu Gln Leu Thr Ser Asp
                260                 265                 270

agt gaa tta gca caa gtt agt tct cca caa cta agg aac cct ccc agg      866
Ser Glu Leu Ala Gln Val Ser Ser Pro Gln Leu Arg Asn Pro Pro Arg
            275                 280                 285

ttg agt gtg aat tgc agt gag atc atc tgt atg ttc aac aat atg gga      914
Leu Ser Val Asn Cys Ser Glu Ile Ile Cys Met Phe Asn Asn Met Gly
        290                 295                 300

aag att gaa ttt agg gac tca aca aaa tgt tat ccc caa gaa aat gaa      962
Lys Ile Glu Phe Arg Asp Ser Thr Lys Cys Tyr Pro Gln Glu Asn Glu
    305                 310                 315

att aga cag aat gtt caa aag aaa tat aat aac aaa aag gaa ctt tct     1010
Ile Arg Gln Asn Val Gln Lys Lys Tyr Asn Asn Lys Lys Glu Leu Ser
320                 325                 330                 335

tgt tac gat aca tac cca ccg cta gaa aag aaa aag gtt gac atg tct     1058
Cys Tyr Asp Thr Tyr Pro Pro Leu Glu Lys Lys Lys Val Asp Met Ser
                340                 345                 350

gtc cta acc agt gaa gca cca cca cca tct ttg caa cct gag aca aat     1106
Val Leu Thr Ser Glu Ala Pro Pro Pro Ser Leu Gln Pro Glu Thr Asn
            355                 360                 365

gat gta cat tta gaa gca aaa aac ttc cag cca cag aaa gac gtt gca     1154
Asp Val His Leu Glu Ala Lys Asn Phe Gln Pro Gln Lys Asp Val Ala
        370                 375                 380

aca gca tcc cct aaa acc att gct gtg tta cct cag atg gga tct agc     1202
Thr Ala Ser Pro Lys Thr Ile Ala Val Leu Pro Gln Met Gly Ser Ser
    385                 390                 395

cct gat gtg ata att gaa gaa att att gaa gac aac gtg gaa agt tct     1250
Pro Asp Val Ile Ile Glu Glu Ile Ile Glu Asp Asn Val Glu Ser Ser
400                 405                 410                 415

gca gag cta gtt ttt gta agc cat gta ata gat cct tgc cat ttc tac     1298
Ala Glu Leu Val Phe Val Ser His Val Ile Asp Pro Cys His Phe Tyr
                420                 425                 430

att cgg aag tat tca caa ata aaa gac gcc aaa gta ctg gag aag aag     1346
Ile Arg Lys Tyr Ser Gln Ile Lys Asp Ala Lys Val Leu Glu Lys Lys
            435                 440                 445
```

```
gtg aat gaa ttt tgc aat agg agt tca cac ctt gat cct tca gac att     1394
Val Asn Glu Phe Cys Asn Arg Ser Ser His Leu Asp Pro Ser Asp Ile
        450                 455                 460

ttg gaa cta ggt gca aga ata ttt gtc agc agt att aaa aat gga atg     1442
Leu Glu Leu Gly Ala Arg Ile Phe Val Ser Ser Ile Lys Asn Gly Met
    465                 470                 475

tgg tgt cga gga act atc aca gaa tta att cca ata gag ggt aga aat     1490
Trp Cys Arg Gly Thr Ile Thr Glu Leu Ile Pro Ile Glu Gly Arg Asn
480                 485                 490                 495

acc aga aaa cct tgt agt cca acc aga tta ttt gtc cat gaa gtt gca     1538
Thr Arg Lys Pro Cys Ser Pro Thr Arg Leu Phe Val His Glu Val Ala
                500                 505                 510

cta ata caa ata ttc atg gta gat ttt gga aat tct gaa gtc ctg att     1586
Leu Ile Gln Ile Phe Met Val Asp Phe Gly Asn Ser Glu Val Leu Ile
            515                 520                 525

gtc act gga gtt gtt gat acc cat gtg aga cca gaa cac tct gct aag     1634
Val Thr Gly Val Val Asp Thr His Val Arg Pro Glu His Ser Ala Lys
        530                 535                 540

caa cat att gca cta aat gat tta tgt ctg gtt cta agg aaa tct gaa     1682
Gln His Ile Ala Leu Asn Asp Leu Cys Leu Val Leu Arg Lys Ser Glu
    545                 550                 555

cca tat act gaa ggg ctg cta aaa gac atc cag cca tta gca caa cca     1730
Pro Tyr Thr Glu Gly Leu Leu Lys Asp Ile Gln Pro Leu Ala Gln Pro
560                 565                 570                 575

tgc tca ttg aaa gac att gtt cca cag aat tca aat gaa ggc tgg gaa     1778
Cys Ser Leu Lys Asp Ile Val Pro Gln Asn Ser Asn Glu Gly Trp Glu
                580                 585                 590

gag gaa gct aaa gtg gaa ttt ttg aaa atg gta aat aac aag gct gtt     1826
Glu Glu Ala Lys Val Glu Phe Leu Lys Met Val Asn Asn Lys Ala Val
            595                 600                 605

tca atg aaa gtt ttt aga gaa gaa gat ggt gtg ctt att gta gat ctg     1874
Ser Met Lys Val Phe Arg Glu Glu Asp Gly Val Leu Ile Val Asp Leu
        610                 615                 620

caa aaa cca cca ccg aat aaa ata agc agt gat atg cct gtg tct ctt     1922
Gln Lys Pro Pro Pro Asn Lys Ile Ser Ser Asp Met Pro Val Ser Leu
    625                 630                 635

aga gat gcg cta gtt ttt atg gaa cta gca aaa gat ctg atc taa         1967
Arg Asp Ala Leu Val Phe Met Glu Leu Ala Lys Asp Leu Ile
640                 645                 650

taaagttggt tgagacactt tctcattttt tcaatgtttc tgtattggaa gaagaactta   2027

aagcttccta atctattttg ttggcgtcat tcctctgctg aatttttaaa tgttcactct   2087

ggcttacctg ttaatggaag aatttgcata atatctactt agaaagatag tgggccccgg   2147

ag                                                                  2149


<210> SEQ ID NO 12
<211> LENGTH: 653
<212> TYPE: PRT
<213> ORGANISM: Homo sapiens

<400> SEQUENCE: 12

Met Ala Ala Glu Ala Ser Lys Thr Gly Pro Ser Arg Ser Ser Tyr Gln
1               5                   10                  15

Arg Met Gly Arg Lys Ser Gln Pro Trp Gly Ala Ala Glu Ile Gln Cys
            20                  25                  30

Thr Arg Cys Gly Arg Arg Val Ser Arg Ser Ser Gly His His Cys Glu
        35                  40                  45

Leu Gln Cys Gly His Ala Phe Cys Glu Leu Cys Leu Leu Met Thr Glu
```

```
    50                  55                  60

Glu Cys Thr Thr Ile Ile Cys Pro Asp Cys Glu Val Ala Thr Ala Val
65                  70                  75                  80

Asn Thr Arg Gln Arg Tyr Tyr Pro Met Ala Gly Tyr Ile Lys Glu Asp
                85                  90                  95

Ser Ile Met Glu Lys Leu Gln Pro Lys Thr Ile Lys Asn Cys Ser Gln
            100                 105                 110

Asp Phe Lys Lys Thr Ala Asp Gln Leu Thr Thr Gly Leu Glu Arg Ser
        115                 120                 125

Ala Ser Thr Asp Lys Thr Leu Leu Asn Ser Ser Ala Val Met Leu Asp
    130                 135                 140

Thr Asn Thr Ala Glu Glu Ile Asp Glu Ala Leu Asn Thr Ala His His
145                 150                 155                 160

Ser Phe Glu Gln Leu Ser Ile Ala Gly Lys Ala Leu Glu His Met Gln
                165                 170                 175

Lys Gln Thr Ile Glu Glu Arg Glu Arg Val Ile Glu Val Val Glu Lys
            180                 185                 190

Gln Phe Asp Gln Leu Leu Ala Phe Phe Asp Ser Arg Lys Lys Asn Leu
        195                 200                 205

Cys Glu Glu Phe Ala Arg Thr Thr Asp Asp Tyr Leu Ser Asn Leu Ile
    210                 215                 220

Lys Ala Lys Ser Tyr Ile Glu Glu Lys Lys Asn Asn Leu Asn Ala Ala
225                 230                 235                 240

Met Asn Ile Ala Arg Ala Leu Gln Leu Ser Pro Ser Leu Arg Thr Tyr
                245                 250                 255

Cys Asp Leu Asn Gln Ile Ile Arg Thr Leu Gln Leu Thr Ser Asp Ser
            260                 265                 270

Glu Leu Ala Gln Val Ser Ser Pro Gln Leu Arg Asn Pro Pro Arg Leu
        275                 280                 285

Ser Val Asn Cys Ser Glu Ile Ile Cys Met Phe Asn Asn Met Gly Lys
    290                 295                 300

Ile Glu Phe Arg Asp Ser Thr Lys Cys Tyr Pro Gln Glu Asn Glu Ile
305                 310                 315                 320

Arg Gln Asn Val Gln Lys Lys Tyr Asn Asn Lys Lys Glu Leu Ser Cys
                325                 330                 335

Tyr Asp Thr Tyr Pro Pro Leu Glu Lys Lys Lys Val Asp Met Ser Val
            340                 345                 350

Leu Thr Ser Glu Ala Pro Pro Pro Ser Leu Gln Pro Glu Thr Asn Asp
        355                 360                 365

Val His Leu Glu Ala Lys Asn Phe Gln Pro Gln Lys Asp Val Ala Thr
    370                 375                 380

Ala Ser Pro Lys Thr Ile Ala Val Leu Pro Gln Met Gly Ser Ser Pro
385                 390                 395                 400

Asp Val Ile Ile Glu Glu Ile Ile Glu Asp Asn Val Glu Ser Ser Ala
                405                 410                 415

Glu Leu Val Phe Val Ser His Val Ile Asp Pro Cys His Phe Tyr Ile
            420                 425                 430

Arg Lys Tyr Ser Gln Ile Lys Asp Ala Lys Val Leu Glu Lys Lys Val
        435                 440                 445

Asn Glu Phe Cys Asn Arg Ser Ser His Leu Asp Pro Ser Asp Ile Leu
    450                 455                 460

Glu Leu Gly Ala Arg Ile Phe Val Ser Ser Ile Lys Asn Gly Met Trp
465                 470                 475                 480
```

```
Cys Arg Gly Thr Ile Thr Glu Leu Ile Pro Ile Glu Gly Arg Asn Thr
            485                 490                 495

Arg Lys Pro Cys Ser Pro Thr Arg Leu Phe Val His Glu Val Ala Leu
            500                 505                 510

Ile Gln Ile Phe Met Val Asp Phe Gly Asn Ser Glu Val Leu Ile Val
        515                 520                 525

Thr Gly Val Val Asp Thr His Val Arg Pro Glu His Ser Ala Lys Gln
    530                 535                 540

His Ile Ala Leu Asn Asp Leu Cys Leu Val Leu Arg Lys Ser Glu Pro
545                 550                 555                 560

Tyr Thr Glu Gly Leu Leu Lys Asp Ile Gln Pro Leu Ala Gln Pro Cys
            565                 570                 575

Ser Leu Lys Asp Ile Val Pro Gln Asn Ser Asn Glu Gly Trp Glu Glu
            580                 585                 590

Glu Ala Lys Val Glu Phe Leu Lys Met Val Asn Asn Lys Ala Val Ser
        595                 600                 605

Met Lys Val Phe Arg Glu Glu Asp Gly Val Leu Ile Val Asp Leu Gln
    610                 615                 620

Lys Pro Pro Pro Asn Lys Ile Ser Ser Asp Met Pro Val Ser Leu Arg
625                 630                 635                 640

Asp Ala Leu Val Phe Met Glu Leu Ala Lys Asp Leu Ile
            645                 650


<210> SEQ ID NO 13
<211> LENGTH: 3072
<212> TYPE: DNA
<213> ORGANISM: Mus musculus
<220> FEATURE:
<221> NAME/KEY: CDS
<222> LOCATION: (1)..(3072)

<400> SEQUENCE: 13

atg gta aat aag aag gct gtc tta atg aaa gtt ttt gga gaa gaa gat       48
Met Val Asn Lys Lys Ala Val Leu Met Lys Val Phe Gly Glu Glu Asp
1               5                   10                  15

gat gtc ctt att gta gat ctg cag aaa cca cca aca aat aaa atc agc       96
Asp Val Leu Ile Val Asp Leu Gln Lys Pro Pro Thr Asn Lys Ile Ser
            20                  25                  30

agt gat atg cct gtg tct ctc aga gat gca ttg gtt ttt atg gaa cta      144
Ser Asp Met Pro Val Ser Leu Arg Asp Ala Leu Val Phe Met Glu Leu
        35                  40                  45

gca agc tgc agt gtc ata tcc ctt tct cct cag atg gag aac ctg gac      192
Ala Ser Cys Ser Val Ile Ser Leu Ser Pro Gln Met Glu Asn Leu Asp
    50                  55                  60

ttt tta tct ctt tta aaa aca att gag gaa ttc tat aaa ggt gaa gat      240
Phe Leu Ser Leu Leu Lys Thr Ile Glu Glu Phe Tyr Lys Gly Glu Asp
65                  70                  75                  80

gga gaa aat ctg gaa atc ctt tgt cct ctt cag aat caa gcc tgt gta      288
Gly Glu Asn Leu Glu Ile Leu Cys Pro Leu Gln Asn Gln Ala Cys Val
                85                  90                  95

gct aaa ttt gaa gat gga atc tgg tat cgt gca aaa gtg atc gga ttg      336
Ala Lys Phe Glu Asp Gly Ile Trp Tyr Arg Ala Lys Val Ile Gly Leu
            100                 105                 110

cct gga cat cgg gaa gta gaa gtt aaa tat gtg gac ttt ggt aat act      384
Pro Gly His Arg Glu Val Glu Val Lys Tyr Val Asp Phe Gly Asn Thr
        115                 120                 125

gca aaa ata aca ctt aaa gat atg cgg aaa ata aag gat gag ttt ttg      432
Ala Lys Ile Thr Leu Lys Asp Met Arg Lys Ile Lys Asp Glu Phe Leu
```

-continued

```
    130                 135                 140

gaa ccc cca gag aag gca att aaa tgt aag ctg gca tat gtt gaa cca      480
Glu Pro Pro Glu Lys Ala Ile Lys Cys Lys Leu Ala Tyr Val Glu Pro
145                 150                 155                 160

agt aaa aaa tca cag tgg tcc aaa aag gct aaa gag aaa ttt gaa gaa      528
Ser Lys Lys Ser Gln Trp Ser Lys Lys Ala Lys Glu Lys Phe Glu Glu
                165                 170                 175

aag act caa gat aaa ttt gtg aca tgt tct gtt att aag att ctg gaa      576
Lys Thr Gln Asp Lys Phe Val Thr Cys Ser Val Ile Lys Ile Leu Glu
            180                 185                 190

aat aat gtg ctc ttg gtt gag ctt ttt gat tct cga gct cct gga aaa      624
Asn Asn Val Leu Leu Val Glu Leu Phe Asp Ser Arg Ala Pro Gly Lys
        195                 200                 205

agt gct gtt agt att aat gac cag ctc gtg aaa gag ggc cta gca tct      672
Ser Ala Val Ser Ile Asn Asp Gln Leu Val Lys Glu Gly Leu Ala Ser
    210                 215                 220

tat gaa gca gga tat acc ctc aaa gat aac tct aaa aag cat ctt gaa      720
Tyr Glu Ala Gly Tyr Thr Leu Lys Asp Asn Ser Lys Lys His Leu Glu
225                 230                 235                 240

gta tgg gat cct tct cct gaa gaa att att aca agt gaa ata aac aac      768
Val Trp Asp Pro Ser Pro Glu Glu Ile Ile Thr Ser Glu Ile Asn Asn
                245                 250                 255

tta agt cct tta tct gta aaa tct cta cct aat gag aat ttc cag tca      816
Leu Ser Pro Leu Ser Val Lys Ser Leu Pro Asn Glu Asn Phe Gln Ser
            260                 265                 270

ttg tat aac aag gag ctg cct gtg aac ata tgc aag aaa gca tca gtg      864
Leu Tyr Asn Lys Glu Leu Pro Val Asn Ile Cys Lys Lys Ala Ser Val
        275                 280                 285

ttg tac cta agg aac ctt tat cac aag caa aag gaa gaa cta gtt caa      912
Leu Tyr Leu Arg Asn Leu Tyr His Lys Gln Lys Glu Glu Leu Val Gln
    290                 295                 300

agt tta gaa gag aag atg gta gca gcg tat gag cac tca gaa tgg aag      960
Ser Leu Glu Glu Lys Met Val Ala Ala Tyr Glu His Ser Glu Trp Lys
305                 310                 315                 320

cct gtt aag tgg gag tgt gat atg cac tgc gct gtt aag gtc cca gct     1008
Pro Val Lys Trp Glu Cys Asp Met His Cys Ala Val Lys Val Pro Ala
                325                 330                 335

aaa aat cag tgg cga aga ggc cag att ctc aga atg gtt aca gac aaa     1056
Lys Asn Gln Trp Arg Arg Gly Gln Ile Leu Arg Met Val Thr Asp Lys
            340                 345                 350

ctg gta gag gtc ttg ctt tat gat gtt ggt gtt gaa cta gta gtg aat     1104
Leu Val Glu Val Leu Leu Tyr Asp Val Gly Val Glu Leu Val Val Asn
        355                 360                 365

att cac tgc tta aga gaa ctt caa gaa aat cta aag aca atg gga aga     1152
Ile His Cys Leu Arg Glu Leu Gln Glu Asn Leu Lys Thr Met Gly Arg
    370                 375                 380

tta tct ttg gaa tgt tca ctt gtt gat ata agg cca act ggc gga agt     1200
Leu Ser Leu Glu Cys Ser Leu Val Asp Ile Arg Pro Thr Gly Gly Ser
385                 390                 395                 400

gac aag tgg aca gca aca gct tgt gac tgt ctg tca ctg cac ctc act     1248
Asp Lys Trp Thr Ala Thr Ala Cys Asp Cys Leu Ser Leu His Leu Thr
                405                 410                 415

gga gcc ata gca acc ata atc tta cag gaa agc aac aca acg tgg cca     1296
Gly Ala Ile Ala Thr Ile Ile Leu Gln Glu Ser Asn Thr Thr Trp Pro
            420                 425                 430

tta cct gtg aaa att ttc tgc cga gat gaa aaa gga gaa cgt gtt gat     1344
Leu Pro Val Lys Ile Phe Cys Arg Asp Glu Lys Gly Glu Arg Val Asp
        435                 440                 445

gtt tct aaa tat ttg att aaa aaa ggt ttg gca ttg aga gag aga aga     1392
```

-continued

```
Val Ser Lys Tyr Leu Ile Lys Lys Gly Leu Ala Leu Arg Glu Arg Arg
    450                 455                 460

gtt agt aaa tca agt aac agc cat tca cct gag aag tct ctg gaa ata      1440
Val Ser Lys Ser Ser Asn Ser His Ser Pro Glu Lys Ser Leu Glu Ile
465                 470                 475                 480

ccc ctg gag caa gga gat tca gta gtt act aag tgc ttt aaa att aac      1488
Pro Leu Glu Gln Gly Asp Ser Val Val Thr Lys Cys Phe Lys Ile Asn
                485                 490                 495

ttt gat act aac aag aaa att gct gat aaa gtc aat gaa cac aaa gta      1536
Phe Asp Thr Asn Lys Lys Ile Ala Asp Lys Val Asn Glu His Lys Val
            500                 505                 510

cct gat tct aag gga aag aaa tca gaa agc aga agc acc gga tgc tat      1584
Pro Asp Ser Lys Gly Lys Lys Ser Glu Ser Arg Ser Thr Gly Cys Tyr
        515                 520                 525

aga cca cca gct gtt cct aac acg agt tca ttt gag gca ata gtg acc      1632
Arg Pro Pro Ala Val Pro Asn Thr Ser Ser Phe Glu Ala Ile Val Thr
    530                 535                 540

tgc att ggt gac gat gga act ata ttt gta gtg cct aaa tta tca gaa      1680
Cys Ile Gly Asp Asp Gly Thr Ile Phe Val Val Pro Lys Leu Ser Glu
545                 550                 555                 560

ttt gag ctc ata aaa atg atg gat gaa att caa agt aat tta aag tgc      1728
Phe Glu Leu Ile Lys Met Met Asp Glu Ile Gln Ser Asn Leu Lys Cys
                565                 570                 575

ctt ggt ctt ttg gag cca tat tcc tgg aaa aag gga gag cct tgt gca      1776
Leu Gly Leu Leu Glu Pro Tyr Ser Trp Lys Lys Gly Glu Pro Cys Ala
            580                 585                 590

gtg aga gga tct gat act ttg tgg tac cgt ggc aaa gtt atg gag gtt      1824
Val Arg Gly Ser Asp Thr Leu Trp Tyr Arg Gly Lys Val Met Glu Val
        595                 600                 605

gtg gga ggc acc atc agg gtc cag tat tta gat cat ggg ttc act gag      1872
Val Gly Gly Thr Ile Arg Val Gln Tyr Leu Asp His Gly Phe Thr Glu
    610                 615                 620

aag att cca caa tgt cat ctg tat cct att ttg ctc tat cct gat act      1920
Lys Ile Pro Gln Cys His Leu Tyr Pro Ile Leu Leu Tyr Pro Asp Thr
625                 630                 635                 640

ccc cag ttc tgt att ccc tgt cag ctc tat cag act tta ccg gtt ggg      1968
Pro Gln Phe Cys Ile Pro Cys Gln Leu Tyr Gln Thr Leu Pro Val Gly
                645                 650                 655

aat acc tgg cag cca gat gcc ata gag ctg ctt cag gag ctg ctt tca      2016
Asn Thr Trp Gln Pro Asp Ala Ile Glu Leu Leu Gln Glu Leu Leu Ser
            660                 665                 670

aag aga gag gtg gac att cac att atg gaa ttg ccc aac aat tca tgg      2064
Lys Arg Glu Val Asp Ile His Ile Met Glu Leu Pro Asn Asn Ser Trp
        675                 680                 685

ggg aag ttg tct gtc cat ctc tat ttt gat ggg atg tca ctt tct cat      2112
Gly Lys Leu Ser Val His Leu Tyr Phe Asp Gly Met Ser Leu Ser His
    690                 695                 700

ttt atg gcc cat cat aaa tac tgt att ttt gaa cat acc gag gag ata      2160
Phe Met Ala His His Lys Tyr Cys Ile Phe Glu His Thr Glu Glu Ile
705                 710                 715                 720

ttt aaa gaa aaa cca aga ggt cag aat aaa aag tat gaa gat gaa aac      2208
Phe Lys Glu Lys Pro Arg Gly Gln Asn Lys Lys Tyr Glu Asp Glu Asn
                725                 730                 735

tgg aaa ata aga ttt gag gac ttg ctt ttg cct gaa atg gag gct ccc      2256
Trp Lys Ile Arg Phe Glu Asp Leu Leu Leu Pro Glu Met Glu Ala Pro
            740                 745                 750

gtt tta cca ccg tat ctg tct tcc ctt ctg cct cca cca gag gag ctg      2304
Val Leu Pro Pro Tyr Leu Ser Ser Leu Leu Pro Pro Pro Glu Glu Leu
        755                 760                 765
```

-continued

```
ttt gcc gtg caa gtg aag cac att gtc tca ccg gat gaa atg tat att     2352
Phe Ala Val Gln Val Lys His Ile Val Ser Pro Asp Glu Met Tyr Ile
    770                 775                 780

tgc ctt gac tct gaa gat agc tat act cag ttt aac cat cat ggt gac     2400
Cys Leu Asp Ser Glu Asp Ser Tyr Thr Gln Phe Asn His His Gly Asp
785                 790                 795                 800

acg gat gac agt gga gtc agc tgg gag tca gag tca gag aac ctg gag     2448
Thr Asp Asp Ser Gly Val Ser Trp Glu Ser Glu Ser Glu Asn Leu Glu
                805                 810                 815

gaa gcg ctg cag aga ttt aac aag aac gtg gag acg ttt cct ccc ctg     2496
Glu Ala Leu Gln Arg Phe Asn Lys Asn Val Glu Thr Phe Pro Pro Leu
            820                 825                 830

acg gat ttt agc tca ggt agc acg gat ttt atg ctg tgt tct gag tgt     2544
Thr Asp Phe Ser Ser Gly Ser Thr Asp Phe Met Leu Cys Ser Glu Cys
        835                 840                 845

cta gga tct ggc gtg gag cag cag ccc ctc ctc ctc gac act tta cag     2592
Leu Gly Ser Gly Val Glu Gln Gln Pro Leu Leu Leu Asp Thr Leu Gln
    850                 855                 860

aag ctc tgt gag cag gtg ccg ctc gag ggc atc agc acc act gtg gtg     2640
Lys Leu Cys Glu Gln Val Pro Leu Glu Gly Ile Ser Thr Thr Val Val
865                 870                 875                 880

cac ata gag atg cct tgc ctt gca gaa tat gct gat ggt ttg tgg tat     2688
His Ile Glu Met Pro Cys Leu Ala Glu Tyr Ala Asp Gly Leu Trp Tyr
                885                 890                 895

aga gca aag atc att tcc att aaa gaa ttt aac cct tta tct gtc ctg     2736
Arg Ala Lys Ile Ile Ser Ile Lys Glu Phe Asn Pro Leu Ser Val Leu
            900                 905                 910

gta ctg ttt gtt gat tat ggt tgc aca gag aag ttg aca ata aac aga     2784
Val Leu Phe Val Asp Tyr Gly Cys Thr Glu Lys Leu Thr Ile Asn Arg
        915                 920                 925

cta cgt cag att cct gtt cag ctt atg cag tac cca gcc caa gcc ata     2832
Leu Arg Gln Ile Pro Val Gln Leu Met Gln Tyr Pro Ala Gln Ala Ile
    930                 935                 940

aag gtg ctc ttg gca ggg ttt aaa cct ccc tta agt gac tcg gga aaa     2880
Lys Val Leu Leu Ala Gly Phe Lys Pro Pro Leu Ser Asp Ser Gly Lys
945                 950                 955                 960

aca aga ata cca tac tgt ccc aaa tgg agc atg gaa gcc ttg tgg act     2928
Thr Arg Ile Pro Tyr Cys Pro Lys Trp Ser Met Glu Ala Leu Trp Thr
                965                 970                 975

atg ata gac tgt ctc caa gga aaa caa ctt tat gct tct tct gtg gct     2976
Met Ile Asp Cys Leu Gln Gly Lys Gln Leu Tyr Ala Ser Ser Val Ala
            980                 985                 990

cag gca cca gaa caa ata gtg aca  tta tat gaa gat gaa  caa tac cca   3024
Gln Ala Pro Glu Gln Ile Val Thr  Leu Tyr Glu Asp Glu  Gln Tyr Pro
        995                 1000                1005

gtt cac  atg tcc ttg gta gaa  atg ggg ctt gca gat  aaa gat gaa      3069
Val His  Met Ser Leu Val Glu  Met Gly Leu Ala Asp  Lys Asp Glu
    1010                1015                1020

tga                                                                 3072


<210> SEQ ID NO 14
<211> LENGTH: 1023
<212> TYPE: PRT
<213> ORGANISM: Mus musculus

<400> SEQUENCE: 14

Met Val Asn Lys Lys Ala Val Leu Met Lys Val Phe Gly Glu Glu Asp
1               5                   10                  15

Asp Val Leu Ile Val Asp Leu Gln Lys Pro Pro Thr Asn Lys Ile Ser
            20                  25                  30
```

```
Ser Asp Met Pro Val Ser Leu Arg Asp Ala Leu Val Phe Met Glu Leu
        35                  40                  45

Ala Ser Cys Ser Val Ile Ser Leu Ser Pro Gln Met Glu Asn Leu Asp
    50                  55                  60

Phe Leu Ser Leu Leu Lys Thr Ile Glu Glu Phe Tyr Lys Gly Glu Asp
65                  70                  75                  80

Gly Glu Asn Leu Glu Ile Leu Cys Pro Leu Gln Asn Gln Ala Cys Val
                85                  90                  95

Ala Lys Phe Glu Asp Gly Ile Trp Tyr Arg Ala Lys Val Ile Gly Leu
            100                 105                 110

Pro Gly His Arg Glu Val Glu Val Lys Tyr Val Asp Phe Gly Asn Thr
        115                 120                 125

Ala Lys Ile Thr Leu Lys Asp Met Arg Lys Ile Lys Asp Glu Phe Leu
    130                 135                 140

Glu Pro Pro Glu Lys Ala Ile Lys Cys Lys Leu Ala Tyr Val Glu Pro
145                 150                 155                 160

Ser Lys Lys Ser Gln Trp Ser Lys Lys Ala Lys Glu Lys Phe Glu Glu
                165                 170                 175

Lys Thr Gln Asp Lys Phe Val Thr Cys Ser Val Ile Lys Ile Leu Glu
            180                 185                 190

Asn Asn Val Leu Leu Val Glu Leu Phe Asp Ser Arg Ala Pro Gly Lys
        195                 200                 205

Ser Ala Val Ser Ile Asn Asp Gln Leu Val Lys Glu Gly Leu Ala Ser
    210                 215                 220

Tyr Glu Ala Gly Tyr Thr Leu Lys Asp Asn Ser Lys Lys His Leu Glu
225                 230                 235                 240

Val Trp Asp Pro Ser Pro Glu Glu Ile Ile Thr Ser Glu Ile Asn Asn
                245                 250                 255

Leu Ser Pro Leu Ser Val Lys Ser Leu Pro Asn Glu Asn Phe Gln Ser
            260                 265                 270

Leu Tyr Asn Lys Glu Leu Pro Val Asn Ile Cys Lys Lys Ala Ser Val
        275                 280                 285

Leu Tyr Leu Arg Asn Leu Tyr His Lys Gln Lys Glu Glu Leu Val Gln
    290                 295                 300

Ser Leu Glu Glu Lys Met Val Ala Ala Tyr Glu His Ser Glu Trp Lys
305                 310                 315                 320

Pro Val Lys Trp Glu Cys Asp Met His Cys Ala Val Lys Val Pro Ala
                325                 330                 335

Lys Asn Gln Trp Arg Arg Gly Gln Ile Leu Arg Met Val Thr Asp Lys
            340                 345                 350

Leu Val Glu Val Leu Leu Tyr Asp Val Gly Val Glu Leu Val Val Asn
        355                 360                 365

Ile His Cys Leu Arg Glu Leu Gln Glu Asn Leu Lys Thr Met Gly Arg
    370                 375                 380

Leu Ser Leu Glu Cys Ser Leu Val Asp Ile Arg Pro Thr Gly Gly Ser
385                 390                 395                 400

Asp Lys Trp Thr Ala Thr Ala Cys Asp Cys Leu Ser Leu His Leu Thr
                405                 410                 415

Gly Ala Ile Ala Thr Ile Ile Leu Gln Glu Ser Asn Thr Thr Trp Pro
            420                 425                 430

Leu Pro Val Lys Ile Phe Cys Arg Asp Glu Lys Gly Glu Arg Val Asp
        435                 440                 445
```

```
Val Ser Lys Tyr Leu Ile Lys Lys Gly Leu Ala Leu Arg Glu Arg Arg
    450                 455                 460

Val Ser Lys Ser Ser Asn Ser His Ser Pro Glu Lys Ser Leu Glu Ile
465                 470                 475                 480

Pro Leu Glu Gln Gly Asp Ser Val Val Thr Lys Cys Phe Lys Ile Asn
                485                 490                 495

Phe Asp Thr Asn Lys Lys Ile Ala Asp Lys Val Asn Glu His Lys Val
            500                 505                 510

Pro Asp Ser Lys Gly Lys Lys Ser Glu Ser Arg Ser Thr Gly Cys Tyr
        515                 520                 525

Arg Pro Pro Ala Val Pro Asn Thr Ser Ser Phe Glu Ala Ile Val Thr
    530                 535                 540

Cys Ile Gly Asp Asp Gly Thr Ile Phe Val Val Pro Lys Leu Ser Glu
545                 550                 555                 560

Phe Glu Leu Ile Lys Met Met Asp Glu Ile Gln Ser Asn Leu Lys Cys
                565                 570                 575

Leu Gly Leu Leu Glu Pro Tyr Ser Trp Lys Lys Gly Glu Pro Cys Ala
            580                 585                 590

Val Arg Gly Ser Asp Thr Leu Trp Tyr Arg Gly Lys Val Met Glu Val
        595                 600                 605

Val Gly Gly Thr Ile Arg Val Gln Tyr Leu Asp His Gly Phe Thr Glu
    610                 615                 620

Lys Ile Pro Gln Cys His Leu Tyr Pro Ile Leu Leu Tyr Pro Asp Thr
625                 630                 635                 640

Pro Gln Phe Cys Ile Pro Cys Gln Leu Tyr Gln Thr Leu Pro Val Gly
                645                 650                 655

Asn Thr Trp Gln Pro Asp Ala Ile Glu Leu Leu Gln Glu Leu Leu Ser
            660                 665                 670

Lys Arg Glu Val Asp Ile His Ile Met Glu Leu Pro Asn Asn Ser Trp
        675                 680                 685

Gly Lys Leu Ser Val His Leu Tyr Phe Asp Gly Met Ser Leu Ser His
    690                 695                 700

Phe Met Ala His His Lys Tyr Cys Ile Phe Glu His Thr Glu Glu Ile
705                 710                 715                 720

Phe Lys Glu Lys Pro Arg Gly Gln Asn Lys Lys Tyr Glu Asp Glu Asn
                725                 730                 735

Trp Lys Ile Arg Phe Glu Asp Leu Leu Leu Pro Glu Met Glu Ala Pro
            740                 745                 750

Val Leu Pro Pro Tyr Leu Ser Ser Leu Leu Pro Pro Pro Glu Glu Leu
        755                 760                 765

Phe Ala Val Gln Val Lys His Ile Val Ser Pro Asp Glu Met Tyr Ile
    770                 775                 780

Cys Leu Asp Ser Glu Asp Ser Tyr Thr Gln Phe Asn His His Gly Asp
785                 790                 795                 800

Thr Asp Asp Ser Gly Val Ser Trp Glu Ser Glu Ser Glu Asn Leu Glu
                805                 810                 815

Glu Ala Leu Gln Arg Phe Asn Lys Asn Val Glu Thr Phe Pro Pro Leu
            820                 825                 830

Thr Asp Phe Ser Ser Gly Ser Thr Asp Phe Met Leu Cys Ser Glu Cys
        835                 840                 845

Leu Gly Ser Gly Val Glu Gln Gln Pro Leu Leu Leu Asp Thr Leu Gln
    850                 855                 860

Lys Leu Cys Glu Gln Val Pro Leu Glu Gly Ile Ser Thr Thr Val Val
```

-continued

```
865                 870                 875                 880

His Ile Glu Met Pro Cys Leu Ala Glu Tyr Ala Asp Gly Leu Trp Tyr
                885                 890                 895

Arg Ala Lys Ile Ile Ser Ile Lys Glu Phe Asn Pro Leu Ser Val Leu
            900                 905                 910

Val Leu Phe Val Asp Tyr Gly Cys Thr Glu Lys Leu Thr Ile Asn Arg
        915                 920                 925

Leu Arg Gln Ile Pro Val Gln Leu Met Gln Tyr Pro Ala Gln Ala Ile
    930                 935                 940

Lys Val Leu Leu Ala Gly Phe Lys Pro Pro Leu Ser Asp Ser Gly Lys
945                 950                 955                 960

Thr Arg Ile Pro Tyr Cys Pro Lys Trp Ser Met Glu Ala Leu Trp Thr
                965                 970                 975

Met Ile Asp Cys Leu Gln Gly Lys Gln Leu Tyr Ala Ser Ser Val Ala
            980                 985                 990

Gln Ala Pro Glu Gln Ile Val Thr  Leu Tyr Glu Asp Glu  Gln Tyr Pro
        995                 1000                1005

Val His  Met Ser Leu Val Glu  Met Gly Leu Ala Asp  Lys Asp Glu
    1010                1015                1020


<210> SEQ ID NO 15
<211> LENGTH: 2792
<212> TYPE: DNA
<213> ORGANISM: Homo sapiens
<220> FEATURE:
<221> NAME/KEY: CDS
<222> LOCATION: (252)..(2564)

<400> SEQUENCE: 15

gtaatactgc aaaaataaca atcaaagacg tgcgtaaaat aaaggatgag tttctgaatg      60

ccccagagaa ggcaattaaa tgtaagttgg cctatattga accatataaa aggacaatgc     120

agtggtccaa agaagctaaa gaaaaatttg aagaaaaggc tcaagataaa tttatgacat     180

gttcagttat caaaattctg gaagataatg tgctcttagt tgagcttttc gattctcttg     240

gtgctcctga a atg act act act agt att aat gac cag cta gtt aaa gag      290
             Met Thr Thr Thr Ser Ile Asn Asp Gln Leu Val Lys Glu
             1               5                   10

ggc cta gca tct tat gaa ata gga tac atc ctc aaa gat aat tct caa      338
Gly Leu Ala Ser Tyr Glu Ile Gly Tyr Ile Leu Lys Asp Asn Ser Gln
    15                  20                  25

aag cat att gaa gtt tgg gat cct tct cca gaa gaa att att tca aat      386
Lys His Ile Glu Val Trp Asp Pro Ser Pro Glu Glu Ile Ile Ser Asn
30                  35                  40                  45

gaa gta cac aac tta aat cct gtg tct gca aaa tct cta cct aat gag      434
Glu Val His Asn Leu Asn Pro Val Ser Ala Lys Ser Leu Pro Asn Glu
                50                  55                  60

aat ttt cag tca ctt tat aat aag gaa ttg cct gtg cat atc tgt aat      482
Asn Phe Gln Ser Leu Tyr Asn Lys Glu Leu Pro Val His Ile Cys Asn
            65                  70                  75

gta ata tct cct gag aag att tat gtt cag tgg ttg tta act gaa aac      530
Val Ile Ser Pro Glu Lys Ile Tyr Val Gln Trp Leu Leu Thr Glu Asn
        80                  85                  90

tta ctt aat agt tta gaa gaa aag atg ata gct gct tat gaa aac tca      578
Leu Leu Asn Ser Leu Glu Glu Lys Met Ile Ala Ala Tyr Glu Asn Ser
    95                  100                 105

aaa tgg gaa cct gtt aaa tgg gaa aat gat atg cac tgt gct gtt aag      626
Lys Trp Glu Pro Val Lys Trp Glu Asn Asp Met His Cys Ala Val Lys
110                 115                 120                 125
```

-continued

```
atc caa gat aaa aat cag tgg cga aga ggc cag atc atc aga atg gtt      674
Ile Gln Asp Lys Asn Gln Trp Arg Arg Gly Gln Ile Ile Arg Met Val
                130                 135                 140

aca gac aca ttg gta gag gtc ttg ctg tat gat gtg ggt gtt gaa cta      722
Thr Asp Thr Leu Val Glu Val Leu Leu Tyr Asp Val Gly Val Glu Leu
            145                 150                 155

gta gtg aat gtt gac tgt tta aga aaa ctt gaa gaa aat cta aag acg      770
Val Val Asn Val Asp Cys Leu Arg Lys Leu Glu Glu Asn Leu Lys Thr
        160                 165                 170

atg gga aga ctc tct ttg gaa tgt tct ctg gtt gac ata aga cca gct      818
Met Gly Arg Leu Ser Leu Glu Cys Ser Leu Val Asp Ile Arg Pro Ala
    175                 180                 185

ggt ggg agt gac aag tgg aca gca aca gct tgt gac tgt ctt tca ttg      866
Gly Gly Ser Asp Lys Trp Thr Ala Thr Ala Cys Asp Cys Leu Ser Leu
190                 195                 200                 205

tac ctg act gga gct gta gca act ata atc tta cag gtg gat agt gag      914
Tyr Leu Thr Gly Ala Val Ala Thr Ile Ile Leu Gln Val Asp Ser Glu
                210                 215                 220

gaa aac aac aca aca tgg cca tta cct gtg aaa att ttc tgc aga gat      962
Glu Asn Asn Thr Thr Trp Pro Leu Pro Val Lys Ile Phe Cys Arg Asp
            225                 230                 235

gaa aaa gga gag cgt gtt gat gtt tct aaa tat ttg att aaa aag ggt     1010
Glu Lys Gly Glu Arg Val Asp Val Ser Lys Tyr Leu Ile Lys Lys Gly
        240                 245                 250

ttg gct ttg aga gaa agg aga att aat aac tta gat aac agc cat tca     1058
Leu Ala Leu Arg Glu Arg Arg Ile Asn Asn Leu Asp Asn Ser His Ser
    255                 260                 265

tta tct gag aag tct ctg gaa gtc ccc ctg gaa cag gaa gat tca gta     1106
Leu Ser Glu Lys Ser Leu Glu Val Pro Leu Glu Gln Glu Asp Ser Val
270                 275                 280                 285

gtt act aac tgt att aaa act aac ttt gac cct gac aag aaa act gct     1154
Val Thr Asn Cys Ile Lys Thr Asn Phe Asp Pro Asp Lys Lys Thr Ala
                290                 295                 300

gac ata atc agt gaa cag aaa gtg tct gaa ttt cag gag aaa att cta     1202
Asp Ile Ile Ser Glu Gln Lys Val Ser Glu Phe Gln Glu Lys Ile Leu
            305                 310                 315

gaa cca aga acc act aga ggg tat aag cca cca gct att cct aac atg     1250
Glu Pro Arg Thr Thr Arg Gly Tyr Lys Pro Pro Ala Ile Pro Asn Met
        320                 325                 330

aac gta ttt gag gca aca gtc agc tgt gtt ggt gat gat gga act ata     1298
Asn Val Phe Glu Ala Thr Val Ser Cys Val Gly Asp Asp Gly Thr Ile
    335                 340                 345

ttt gta gta cct aaa cta tca gaa ttt gag cta ata aaa atg aca aat     1346
Phe Val Val Pro Lys Leu Ser Glu Phe Glu Leu Ile Lys Met Thr Asn
350                 355                 360                 365

gaa att caa agt aat tta aaa tgc ctt ggt ctt ttg gag cct tat ttc     1394
Glu Ile Gln Ser Asn Leu Lys Cys Leu Gly Leu Leu Glu Pro Tyr Phe
                370                 375                 380

tgg aaa aaa gga gaa gca tgt gca gta aga gga tcc gat act ctg tgg     1442
Trp Lys Lys Gly Glu Ala Cys Ala Val Arg Gly Ser Asp Thr Leu Trp
            385                 390                 395

tat cgt ggc aag gtg atg gag gtt gta ggt ggc gct gtc aga gta caa     1490
Tyr Arg Gly Lys Val Met Glu Val Val Gly Gly Ala Val Arg Val Gln
        400                 405                 410

tat tta gat cat gga ttc act gaa aag att ccg cag tgc cat ctt tac     1538
Tyr Leu Asp His Gly Phe Thr Glu Lys Ile Pro Gln Cys His Leu Tyr
    415                 420                 425

cct att ttg ctg tat cct gat ata ccc cag ttt tgt att cct tgt cag     1586
Pro Ile Leu Leu Tyr Pro Asp Ile Pro Gln Phe Cys Ile Pro Cys Gln
```

-continued

```
430                 435                 440                 445

ctc cat aat acc aca cct gtt ggg aat gtc tgg caa cca gat gca ata      1634
Leu His Asn Thr Thr Pro Val Gly Asn Val Trp Gln Pro Asp Ala Ile
                450                 455                 460

gaa gtt ctt caa caa ctg ctt tca aag aga cag gag tta cct aaa aat      1682
Glu Val Leu Gln Gln Leu Leu Ser Lys Arg Gln Glu Leu Pro Lys Asn
            465                 470                 475

cca tgg gag aaa ttg tct att cac ctc tat ttt gat gga atg tca ctt      1730
Pro Trp Glu Lys Leu Ser Ile His Leu Tyr Phe Asp Gly Met Ser Leu
        480                 485                 490

tct tat ttt atg gca tac tat aaa tac tgt act tct gaa cat act gag      1778
Ser Tyr Phe Met Ala Tyr Tyr Lys Tyr Cys Thr Ser Glu His Thr Glu
    495                 500                 505

gag atg ttg aaa gaa aaa cca aga tca gat cat gat aaa aag tat gaa      1826
Glu Met Leu Lys Glu Lys Pro Arg Ser Asp His Asp Lys Lys Tyr Glu
510                 515                 520                 525

gag aaa caa tgg gaa ata agg ttt gag gaa ttg ctt tcg gct gaa aca      1874
Glu Lys Gln Trp Glu Ile Arg Phe Glu Glu Leu Leu Ser Ala Glu Thr
                530                 535                 540

gac act cct ctt tta cca cca tat ttg tct tca tct ctg cct tcc cca      1922
Asp Thr Pro Leu Leu Pro Pro Tyr Leu Ser Ser Ser Leu Pro Ser Pro
            545                 550                 555

gga gaa ctc tat gct gtt caa gtt aag cac gtt gtc tca cct aat gaa      1970
Gly Glu Leu Tyr Ala Val Gln Val Lys His Val Val Ser Pro Asn Glu
        560                 565                 570

gtg tat att tgc ctt gat tct ata gaa act tct aac cag tct aac cag      2018
Val Tyr Ile Cys Leu Asp Ser Ile Glu Thr Ser Asn Gln Ser Asn Gln
    575                 580                 585

cat agt gac aca gat gat agt gga gtc agc ggg gaa tca gaa tcc gag      2066
His Ser Asp Thr Asp Asp Ser Gly Val Ser Gly Glu Ser Glu Ser Glu
590                 595                 600                 605

agc ctt gat gaa gca ctg cag agg gtt aat aag aag gta gag gcg ctt      2114
Ser Leu Asp Glu Ala Leu Gln Arg Val Asn Lys Lys Val Glu Ala Leu
                610                 615                 620

cct cct ctg acg gat ttt aga aca gaa atg cct tgc ctt gca gaa tat      2162
Pro Pro Leu Thr Asp Phe Arg Thr Glu Met Pro Cys Leu Ala Glu Tyr
            625                 630                 635

gat gat ggc tta tgg tat aga gcg aag att gtt gcc att aaa gaa ttt      2210
Asp Asp Gly Leu Trp Tyr Arg Ala Lys Ile Val Ala Ile Lys Glu Phe
        640                 645                 650

aat cct tta tct atc tta gta caa ttt gtt gat tat gga tca act gca      2258
Asn Pro Leu Ser Ile Leu Val Gln Phe Val Asp Tyr Gly Ser Thr Ala
    655                 660                 665

aag ctg aca tta aac aga ctg tgc caa att cct tct cat ctt atg cgg      2306
Lys Leu Thr Leu Asn Arg Leu Cys Gln Ile Pro Ser His Leu Met Arg
670                 675                 680                 685

tat cca gct cga gcc ata aag gtt ctc ttg gca ggg ttt aaa cct ccc      2354
Tyr Pro Ala Arg Ala Ile Lys Val Leu Leu Ala Gly Phe Lys Pro Pro
                690                 695                 700

tta agg gat cta ggg gag aca aga ata cca tat tgt ccc aaa tgg agc      2402
Leu Arg Asp Leu Gly Glu Thr Arg Ile Pro Tyr Cys Pro Lys Trp Ser
            705                 710                 715

atg gag gca ctg tgg gct atg ata gac tgt ctt caa gga aaa caa ctc      2450
Met Glu Ala Leu Trp Ala Met Ile Asp Cys Leu Gln Gly Lys Gln Leu
        720                 725                 730

tat gct gtg tcc atg gct cca gca cca gaa cag ata gtg aca tta tat      2498
Tyr Ala Val Ser Met Ala Pro Ala Pro Glu Gln Ile Val Thr Leu Tyr
    735                 740                 745

gac gat gaa cag cat cca gtt cat atg ccg ttg gta gaa atg ggg ctt      2546
```

-continued

```
Asp Asp Glu Gln His Pro Val His Met Pro Leu Val Glu Met Gly Leu
750                 755                 760                 765

gca gat aaa gat gaa taa gtgcctaagt gtatacagtg agagcatcta            2594
Ala Asp Lys Asp Glu
                770

tagaagccta gaagaattct gttatgttta gactatgtct tatctttaga ctatttcagg   2654

cttaattttc ctaacttgtt cagcactagt gctttacctc tcatttttaa ttgaactgtt   2714

aggaattgtg tggggaaaaa aagtaaataa atgttcgctt ccaaaaaaaa aaaaaaaaaa   2774

aaaaaaaaaa aaaaaaaa                                                 2792


<210> SEQ ID NO 16
<211> LENGTH: 770
<212> TYPE: PRT
<213> ORGANISM: Homo sapiens

<400> SEQUENCE: 16

Met Thr Thr Thr Ser Ile Asn Asp Gln Leu Val Lys Glu Gly Leu Ala
1               5                   10                  15

Ser Tyr Glu Ile Gly Tyr Ile Leu Lys Asp Asn Ser Gln Lys His Ile
            20                  25                  30

Glu Val Trp Asp Pro Ser Pro Glu Glu Ile Ile Ser Asn Glu Val His
        35                  40                  45

Asn Leu Asn Pro Val Ser Ala Lys Ser Leu Pro Asn Glu Asn Phe Gln
    50                  55                  60

Ser Leu Tyr Asn Lys Glu Leu Pro Val His Ile Cys Asn Val Ile Ser
65                  70                  75                  80

Pro Glu Lys Ile Tyr Val Gln Trp Leu Leu Thr Glu Asn Leu Leu Asn
                85                  90                  95

Ser Leu Glu Glu Lys Met Ile Ala Ala Tyr Glu Asn Ser Lys Trp Glu
            100                 105                 110

Pro Val Lys Trp Glu Asn Asp Met His Cys Ala Val Lys Ile Gln Asp
        115                 120                 125

Lys Asn Gln Trp Arg Arg Gly Gln Ile Ile Arg Met Val Thr Asp Thr
    130                 135                 140

Leu Val Glu Val Leu Leu Tyr Asp Val Gly Val Glu Leu Val Val Asn
145                 150                 155                 160

Val Asp Cys Leu Arg Lys Leu Glu Glu Asn Leu Lys Thr Met Gly Arg
                165                 170                 175

Leu Ser Leu Glu Cys Ser Leu Val Asp Ile Arg Pro Ala Gly Gly Ser
            180                 185                 190

Asp Lys Trp Thr Ala Thr Ala Cys Asp Cys Leu Ser Leu Tyr Leu Thr
        195                 200                 205

Gly Ala Val Ala Thr Ile Ile Leu Gln Val Asp Ser Glu Glu Asn Asn
    210                 215                 220

Thr Thr Trp Pro Leu Pro Val Lys Ile Phe Cys Arg Asp Glu Lys Gly
225                 230                 235                 240

Glu Arg Val Asp Val Ser Lys Tyr Leu Ile Lys Lys Gly Leu Ala Leu
                245                 250                 255

Arg Glu Arg Arg Ile Asn Asn Leu Asp Asn Ser His Ser Leu Ser Glu
            260                 265                 270

Lys Ser Leu Glu Val Pro Leu Glu Gln Glu Asp Ser Val Val Thr Asn
        275                 280                 285

Cys Ile Lys Thr Asn Phe Asp Pro Asp Lys Lys Thr Ala Asp Ile Ile
    290                 295                 300
```

-continued

```
Ser Glu Gln Lys Val Ser Glu Phe Gln Glu Lys Ile Leu Glu Pro Arg
305                 310                 315                 320

Thr Thr Arg Gly Tyr Lys Pro Pro Ala Ile Pro Asn Met Asn Val Phe
                325                 330                 335

Glu Ala Thr Val Ser Cys Val Gly Asp Asp Gly Thr Ile Phe Val Val
            340                 345                 350

Pro Lys Leu Ser Glu Phe Glu Leu Ile Lys Met Thr Asn Glu Ile Gln
        355                 360                 365

Ser Asn Leu Lys Cys Leu Gly Leu Leu Glu Pro Tyr Phe Trp Lys Lys
    370                 375                 380

Gly Glu Ala Cys Ala Val Arg Gly Ser Asp Thr Leu Trp Tyr Arg Gly
385                 390                 395                 400

Lys Val Met Glu Val Val Gly Gly Ala Val Arg Val Gln Tyr Leu Asp
                405                 410                 415

His Gly Phe Thr Glu Lys Ile Pro Gln Cys His Leu Tyr Pro Ile Leu
            420                 425                 430

Leu Tyr Pro Asp Ile Pro Gln Phe Cys Ile Pro Cys Gln Leu His Asn
        435                 440                 445

Thr Thr Pro Val Gly Asn Val Trp Gln Pro Asp Ala Ile Glu Val Leu
    450                 455                 460

Gln Gln Leu Leu Ser Lys Arg Gln Glu Leu Pro Lys Asn Pro Trp Glu
465                 470                 475                 480

Lys Leu Ser Ile His Leu Tyr Phe Asp Gly Met Ser Leu Ser Tyr Phe
                485                 490                 495

Met Ala Tyr Tyr Lys Tyr Cys Thr Ser Glu His Thr Glu Glu Met Leu
            500                 505                 510

Lys Glu Lys Pro Arg Ser Asp His Asp Lys Lys Tyr Glu Glu Lys Gln
        515                 520                 525

Trp Glu Ile Arg Phe Glu Glu Leu Leu Ser Ala Glu Thr Asp Thr Pro
    530                 535                 540

Leu Leu Pro Pro Tyr Leu Ser Ser Ser Leu Pro Ser Pro Gly Glu Leu
545                 550                 555                 560

Tyr Ala Val Gln Val Lys His Val Val Ser Pro Asn Glu Val Tyr Ile
                565                 570                 575

Cys Leu Asp Ser Ile Glu Thr Ser Asn Gln Ser Asn Gln His Ser Asp
            580                 585                 590

Thr Asp Asp Ser Gly Val Ser Gly Glu Ser Glu Ser Glu Ser Leu Asp
        595                 600                 605

Glu Ala Leu Gln Arg Val Asn Lys Lys Val Glu Ala Leu Pro Pro Leu
    610                 615                 620

Thr Asp Phe Arg Thr Glu Met Pro Cys Leu Ala Glu Tyr Asp Asp Gly
625                 630                 635                 640

Leu Trp Tyr Arg Ala Lys Ile Val Ala Ile Lys Glu Phe Asn Pro Leu
                645                 650                 655

Ser Ile Leu Val Gln Phe Val Asp Tyr Gly Ser Thr Ala Lys Leu Thr
            660                 665                 670

Leu Asn Arg Leu Cys Gln Ile Pro Ser His Leu Met Arg Tyr Pro Ala
        675                 680                 685

Arg Ala Ile Lys Val Leu Leu Ala Gly Phe Lys Pro Pro Leu Arg Asp
    690                 695                 700

Leu Gly Glu Thr Arg Ile Pro Tyr Cys Pro Lys Trp Ser Met Glu Ala
705                 710                 715                 720
```

-continued

Leu Trp Ala Met Ile Asp Cys Leu Gln Gly Lys Gln Leu Tyr Ala Val
                725                 730                 735

Ser Met Ala Pro Ala Pro Glu Gln Ile Val Thr Leu Tyr Asp Asp Glu
            740                 745                 750

Gln His Pro Val His Met Pro Leu Val Glu Met Gly Leu Ala Asp Lys
        755                 760                 765

Asp Glu
    770

<210> SEQ ID NO 17
<211> LENGTH: 3393
<212> TYPE: DNA
<213> ORGANISM: Mus musculus
<220> FEATURE:
<221> NAME/KEY: CDS
<222> LOCATION: (1)..(3390)

<400> SEQUENCE: 17 atg gcg gca gag gct tcg tcg acc ggg ctg gct tcc tgt cac cta gtg       48
Met Ala Ala Glu Ala Ser Ser Thr Gly Leu Ala Ser Cys His Leu Val
1               5                   10                  15 gag agt aag agt gga gcg cag ggt gct tcg ggg tgt cag tgc act cgg       96
Glu Ser Lys Ser Gly Ala Gln Gly Ala Ser Gly Cys Gln Cys Thr Arg
            20                  25                  30 tgt gga agg aag gtg tcc gtt gcc tcc ggt gac cac cac aag ttt cca      144
Cys Gly Arg Lys Val Ser Val Ala Ser Gly Asp His His Lys Phe Pro
        35                  40                  45 tgt gga cat gcc ttt tgt gaa ctg tgc ctg tta gca cct caa gaa tat      192
Cys Gly His Ala Phe Cys Glu Leu Cys Leu Leu Ala Pro Gln Glu Tyr
    50                  55                  60 acc aca agt aaa tgc act gac tgt gag gtt cat aca act gtc agc atg      240
Thr Thr Ser Lys Cys Thr Asp Cys Glu Val His Thr Thr Val Ser Met
65                  70                  75                  80 aat caa ggt cac tac cca gta gat ggc ttc atc gag gaa gat tct tct      288
Asn Gln Gly His Tyr Pro Val Asp Gly Phe Ile Glu Glu Asp Ser Ser
                85                  90                  95 ctg gaa gcc ttg cca ccg aaa atg gta aat aac tgc tct tca gat ctt      336
Leu Glu Ala Leu Pro Pro Lys Met Val Asn Asn Cys Ser Ser Asp Leu
            100                 105                 110 gaa aag aca gtg gac cag cta att aat gat tta gaa cat tca tcc tcc      384
Glu Lys Thr Val Asp Gln Leu Ile Asn Asp Leu Glu His Ser Ser Ser
        115                 120                 125 ata cat agg aat gtt tca aac cca tca gct gta atg tcg gag aca gaa      432
Ile His Arg Asn Val Ser Asn Pro Ser Ala Val Met Ser Glu Thr Glu
    130                 135                 140 gaa att gat gaa gca ctg aag ata gca ggc tgt aat ttt gaa caa tta      480
Glu Ile Asp Glu Ala Leu Lys Ile Ala Gly Cys Asn Phe Glu Gln Leu
145                 150                 155                 160 agt aat gct ata aaa atg ctt gat agc aca caa gat caa aca aga caa      528
Ser Asn Ala Ile Lys Met Leu Asp Ser Thr Gln Asp Gln Thr Arg Gln
                165                 170                 175 gag aca cac agt cta aca gag gct gtg gag aaa cag ttt gat aca ctt      576
Glu Thr His Ser Leu Thr Glu Ala Val Glu Lys Gln Phe Asp Thr Leu
            180                 185                 190 ctt gct tct ctt gat tcc agg aaa aag agc ttg tgt gaa gaa ctt ata      624
Leu Ala Ser Leu Asp Ser Arg Lys Lys Ser Leu Cys Glu Glu Leu Ile
        195                 200                 205 agg cgt aca gat gat tat tta tca aaa tta gta aca gtt aaa agc tac      672
Arg Arg Thr Asp Asp Tyr Leu Ser Lys Leu Val Thr Val Lys Ser Tyr
    210                 215                 220

-continued

```
att gaa gag aaa aaa agt gat ttg gat gca gct atg aag ata gca aaa      720
Ile Glu Glu Lys Lys Ser Asp Leu Asp Ala Ala Met Lys Ile Ala Lys
225                 230                 235                 240

gaa ctc aga tct gct cct tct ctg agg acc tac tgt gac ctg act cag      768
Glu Leu Arg Ser Ala Pro Ser Leu Arg Thr Tyr Cys Asp Leu Thr Gln
                245                 250                 255

att atc cgg act ttg aag tta aca ttt gaa agt gaa ttg tca caa gtt      816
Ile Ile Arg Thr Leu Lys Leu Thr Phe Glu Ser Glu Leu Ser Gln Val
            260                 265                 270

agt tcc ata att cca agg aac acc cct agg ttg gat ata aat tgc agt      864
Ser Ser Ile Ile Pro Arg Asn Thr Pro Arg Leu Asp Ile Asn Cys Ser
        275                 280                 285

gag gcc atc tgc atg ttc agc agt atg gga aag att gaa ttt gag gac      912
Glu Ala Ile Cys Met Phe Ser Ser Met Gly Lys Ile Glu Phe Glu Asp
    290                 295                 300

tca aca aaa tgt tac cct caa gaa aat gaa gat gga cag aat gtt caa      960
Ser Thr Lys Cys Tyr Pro Gln Glu Asn Glu Asp Gly Gln Asn Val Gln
305                 310                 315                 320

aag aaa ttt aat aat aga aag gaa ctc tgt tgt gat gta tac tca tca     1008
Lys Lys Phe Asn Asn Arg Lys Glu Leu Cys Cys Asp Val Tyr Ser Ser
                325                 330                 335

cta gaa aag aaa aag gta gat gct gct gtc ctg act gat gaa aca cct     1056
Leu Glu Lys Lys Lys Val Asp Ala Ala Val Leu Thr Asp Glu Thr Pro
            340                 345                 350

gaa cct cct ttg caa gca gag gcc cct gac agg cat tta gaa ggg aaa     1104
Glu Pro Pro Leu Gln Ala Glu Ala Pro Asp Arg His Leu Glu Gly Lys
        355                 360                 365

aag aag cag cca aca aaa gag atg gtt gtg gtg aca tct cct aag act     1152
Lys Lys Gln Pro Thr Lys Glu Met Val Val Val Thr Ser Pro Lys Thr
    370                 375                 380

att gct gta ctg cct caa ctg gga tcc agc cct gat gtg ata att gag     1200
Ile Ala Val Leu Pro Gln Leu Gly Ser Ser Pro Asp Val Ile Ile Glu
385                 390                 395                 400

gaa att att gag gaa aac cta gaa tca tgc ttt aca gat gat cct ata     1248
Glu Ile Ile Glu Glu Asn Leu Glu Ser Cys Phe Thr Asp Asp Pro Ile
                405                 410                 415

gag act tct gga tac cca aaa aag ccc cct cag aaa gag cag tct gct     1296
Glu Thr Ser Gly Tyr Pro Lys Lys Pro Pro Gln Lys Glu Gln Ser Ala
            420                 425                 430

cct gtt gga tca aaa gca ggt tgt cca gag cta gtt ttt gta agt cat     1344
Pro Val Gly Ser Lys Ala Gly Cys Pro Glu Leu Val Phe Val Ser His
        435                 440                 445

gta ata cat cct tgc cac ttc tat gtg cgg aaa tat tca caa ata aaa     1392
Val Ile His Pro Cys His Phe Tyr Val Arg Lys Tyr Ser Gln Ile Lys
    450                 455                 460

gat gca aca ata ttg gag aag aag atg aag caa gtt tgc aat agg agc     1440
Asp Ala Thr Ile Leu Glu Lys Lys Met Lys Gln Val Cys Asn Arg Ser
465                 470                 475                 480

tta cac ctt gat cct tca gac att ttg gaa cta ggt gca aga ata ttt     1488
Leu His Leu Asp Pro Ser Asp Ile Leu Glu Leu Gly Ala Arg Ile Phe
                485                 490                 495

gtc aac agt att aag aat aga atg tgg tgt cga gga att atc act gaa     1536
Val Asn Ser Ile Lys Asn Arg Met Trp Cys Arg Gly Ile Ile Thr Glu
            500                 505                 510

ata att cca tca aaa act aaa aat att aga aaa cca tgt agt cca acc     1584
Ile Ile Pro Ser Lys Thr Lys Asn Ile Arg Lys Pro Cys Ser Pro Thr
        515                 520                 525

aaa ttc tca gtc tgt gaa att tca cta ata cag ata ttc atg gta gat     1632
Lys Phe Ser Val Cys Glu Ile Ser Leu Ile Gln Ile Phe Met Val Asp
    530                 535                 540
```

```
ttt gga aat tct gaa gtc ctg atc atc aca gga gtt ggt gac aca cat     1680
Phe Gly Asn Ser Glu Val Leu Ile Ile Thr Gly Val Gly Asp Thr His
545                 550                 555                 560

gag gga cca gag cat gat ggt gaa cag cat att aca cta agt gac ttc     1728
Glu Gly Pro Glu His Asp Gly Glu Gln His Ile Thr Leu Ser Asp Phe
                565                 570                 575

tgt ctg ctt cta atg aag tct gaa cca tac agt gag gaa ctg ttg aaa     1776
Cys Leu Leu Leu Met Lys Ser Glu Pro Tyr Ser Glu Glu Leu Leu Lys
            580                 585                 590

gac atc cca cat tta gca cac ctg tgc tcc ttg aaa gac atc gtc cca     1824
Asp Ile Pro His Leu Ala His Leu Cys Ser Leu Lys Asp Ile Val Pro
        595                 600                 605

tac aat tca act gag ggc tgg gaa aag gag gca aaa gtg gaa ttt ttg     1872
Tyr Asn Ser Thr Glu Gly Trp Glu Lys Glu Ala Lys Val Glu Phe Leu
    610                 615                 620

aaa atg gta aat aag aag gct gtc tta atg aaa gtt ttt gga gaa gaa     1920
Lys Met Val Asn Lys Lys Ala Val Leu Met Lys Val Phe Gly Glu Glu
625                 630                 635                 640

gat gat gtc ctt att gta gat ctg cag aaa cca cca aca aat aaa atc     1968
Asp Asp Val Leu Ile Val Asp Leu Gln Lys Pro Pro Thr Asn Lys Ile
                645                 650                 655

agc agt gat atg cct gtg tct ctc aga gat gca ttg gtt ttt atg gaa     2016
Ser Ser Asp Met Pro Val Ser Leu Arg Asp Ala Leu Val Phe Met Glu
            660                 665                 670

cta gca agg ttt agg tca caa tca cca aga agt cac agt gaa aaa aat     2064
Leu Ala Arg Phe Arg Ser Gln Ser Pro Arg Ser His Ser Glu Lys Asn
        675                 680                 685

aca act tta tgc tat cat cca ccc att ttg cct gaa gag atg act gaa     2112
Thr Thr Leu Cys Tyr His Pro Pro Ile Leu Pro Glu Glu Met Thr Glu
    690                 695                 700

gtt tca gtc atg gtt tgc cat ata aat agt cct act gat ttt tat ctt     2160
Val Ser Val Met Val Cys His Ile Asn Ser Pro Thr Asp Phe Tyr Leu
705                 710                 715                 720

cag ctg atg gag aac ctg gac ttt tta tct ctt tta aaa aca att gag     2208
Gln Leu Met Glu Asn Leu Asp Phe Leu Ser Leu Leu Lys Thr Ile Glu
                725                 730                 735

gaa ttc tat aaa ggt gaa gat gga gaa aat ctg gaa atc ctt tgt cct     2256
Glu Phe Tyr Lys Gly Glu Asp Gly Glu Asn Leu Glu Ile Leu Cys Pro
            740                 745                 750

ctt cag aat caa gcc tgt gta gct aaa ttt gaa gat gga atc tgg tat     2304
Leu Gln Asn Gln Ala Cys Val Ala Lys Phe Glu Asp Gly Ile Trp Tyr
        755                 760                 765

cgt gca aaa gtg atc gga ttg cct gga cat cgg gaa gta gaa gtt aaa     2352
Arg Ala Lys Val Ile Gly Leu Pro Gly His Arg Glu Val Glu Val Lys
    770                 775                 780

tat gtg gac ttt ggt aat act gca aaa ata aca ctt aaa gat atg cgg     2400
Tyr Val Asp Phe Gly Asn Thr Ala Lys Ile Thr Leu Lys Asp Met Arg
785                 790                 795                 800

aaa ata aag gat gag ttt ttg gaa ccc cca gag aag gca att aaa tgt     2448
Lys Ile Lys Asp Glu Phe Leu Glu Pro Pro Glu Lys Ala Ile Lys Cys
                805                 810                 815

aag ctg gca tat gtt gaa cca agt aaa aaa tca cag tgg tcc aaa aag     2496
Lys Leu Ala Tyr Val Glu Pro Ser Lys Lys Ser Gln Trp Ser Lys Lys
            820                 825                 830

gct aaa gag aaa ttt gaa gaa aag act caa gat aaa ttt gtg aca tgt     2544
Ala Lys Glu Lys Phe Glu Glu Lys Thr Gln Asp Lys Phe Val Thr Cys
        835                 840                 845

tct gtt att aag att ctg gaa aat aat gtg ctc ttg gtt gag ctt ttt     2592
Ser Val Ile Lys Ile Leu Glu Asn Asn Val Leu Leu Val Glu Leu Phe
```

```
    850                 855                 860

gat tct cga gct cct gga aaa agt gct gtt agt att aat gac cag ctc      2640
Asp Ser Arg Ala Pro Gly Lys Ser Ala Val Ser Ile Asn Asp Gln Leu
865                 870                 875                 880

gtg aaa gag ggc cta gca tct tat gaa gca gga tat acc ctc aaa gat      2688
Val Lys Glu Gly Leu Ala Ser Tyr Glu Ala Gly Tyr Thr Leu Lys Asp
                885                 890                 895

aac tct aaa aag cat ctt gaa gta tgg gat cct tct cct gaa gaa att      2736
Asn Ser Lys Lys His Leu Glu Val Trp Asp Pro Ser Pro Glu Glu Ile
            900                 905                 910

att aca agt gaa ata aac aac tta agt cct tta tct gta aaa tct cta      2784
Ile Thr Ser Glu Ile Asn Asn Leu Ser Pro Leu Ser Val Lys Ser Leu
        915                 920                 925

cct aat gag aat ttc cag tca ttg tat aac aag gag ctg cct gtg aac      2832
Pro Asn Glu Asn Phe Gln Ser Leu Tyr Asn Lys Glu Leu Pro Val Asn
    930                 935                 940

ata tgt aat gta ata tct cct gag aag att tat gtt cag tgg tta tta      2880
Ile Cys Asn Val Ile Ser Pro Glu Lys Ile Tyr Val Gln Trp Leu Leu
945                 950                 955                 960

aca gaa aac tta ctt aat agt tta gaa gag aag atg gta gca gcg tat      2928
Thr Glu Asn Leu Leu Asn Ser Leu Glu Glu Lys Met Val Ala Ala Tyr
                965                 970                 975

gag cac tca gaa tgg aag cct gtt aag tgg gag tgt gat atg cac tgc      2976
Glu His Ser Glu Trp Lys Pro Val Lys Trp Glu Cys Asp Met His Cys
            980                 985                 990

gct gtt aag gtc cca gct aaa aat  cag tgg cga aga ggc  cag att ctc    3024
Ala Val Lys Val Pro Ala Lys Asn  Gln Trp Arg Arg Gly  Gln Ile Leu
        995                 1000                1005

aga atg  gtt aca gac aaa ctg  gta gag gtc ttg ctt  tat gat gtt      3069
Arg Met  Val Thr Asp Lys Leu  Val Glu Val Leu Leu  Tyr Asp Val
    1010                1015                1020

ggt gtt  gaa cta gta gtg aat  att cac tgc tta aga  gaa ctt caa      3114
Gly Val  Glu Leu Val Val Asn  Ile His Cys Leu Arg  Glu Leu Gln
    1025                1030                1035

gaa aat  cta aag aca atg gga  aga tta tct ttg gaa  tgt tca ctt      3159
Glu Asn  Leu Lys Thr Met Gly  Arg Leu Ser Leu Glu  Cys Ser Leu
    1040                1045                1050

gtt gat  ata agg cca act ggc  gga agt gac aag tgg  aca gca aca      3204
Val Asp  Ile Arg Pro Thr Gly  Gly Ser Asp Lys Trp  Thr Ala Thr
    1055                1060                1065

gct tgt  gac tgt ctc tca ttg  tac ctc act gga gcc  ata gca acc      3249
Ala Cys  Asp Cys Leu Ser Leu  Tyr Leu Thr Gly Ala  Ile Ala Thr
    1070                1075                1080

ata atc  tta cag gaa agc aac  aca acg tgg cca tta  cct gtg aaa      3294
Ile Ile  Leu Gln Glu Ser Asn  Thr Thr Trp Pro Leu  Pro Val Lys
    1085                1090                1095

att ttc  tgc cga gat gaa aaa  gga gaa cgt gtt gat  gtt tct aaa      3339
Ile Phe  Cys Arg Asp Glu Lys  Gly Glu Arg Val Asp  Val Ser Lys
    1100                1105                1110

tat ttg  att aaa aaa ggt ttg  gca ttg aga gag aga  agg gcc tcc      3384
Tyr Leu  Ile Lys Lys Gly Leu  Ala Leu Arg Glu Arg  Arg Ala Ser
    1115                1120                1125

tcc tcc  taa                                                       3393
Ser Ser
    1130
```

<210> SEQ ID NO 18
<211> LENGTH: 1130
<212> TYPE: PRT
<213> ORGANISM: Mus musculus

<400> SEQUENCE: 18

```
Met Ala Ala Glu Ala Ser Ser Thr Gly Leu Ala Ser Cys His Leu Val
1               5                   10                  15

Glu Ser Lys Ser Gly Ala Gln Gly Ala Ser Gly Cys Gln Cys Thr Arg
            20                  25                  30

Cys Gly Arg Lys Val Ser Val Ala Ser Gly Asp His His Lys Phe Pro
        35                  40                  45

Cys Gly His Ala Phe Cys Glu Leu Cys Leu Leu Ala Pro Gln Glu Tyr
    50                  55                  60

Thr Thr Ser Lys Cys Thr Asp Cys Glu Val His Thr Thr Val Ser Met
65                  70                  75                  80

Asn Gln Gly His Tyr Pro Val Asp Gly Phe Ile Glu Glu Asp Ser Ser
                85                  90                  95

Leu Glu Ala Leu Pro Pro Lys Met Val Asn Asn Cys Ser Ser Asp Leu
            100                 105                 110

Glu Lys Thr Val Asp Gln Leu Ile Asn Asp Leu Glu His Ser Ser Ser
        115                 120                 125

Ile His Arg Asn Val Ser Asn Pro Ser Ala Val Met Ser Glu Thr Glu
    130                 135                 140

Glu Ile Asp Glu Ala Leu Lys Ile Ala Gly Cys Asn Phe Glu Gln Leu
145                 150                 155                 160

Ser Asn Ala Ile Lys Met Leu Asp Ser Thr Gln Asp Gln Thr Arg Gln
                165                 170                 175

Glu Thr His Ser Leu Thr Glu Ala Val Glu Lys Gln Phe Asp Thr Leu
            180                 185                 190

Leu Ala Ser Leu Asp Ser Arg Lys Lys Ser Leu Cys Glu Glu Leu Ile
        195                 200                 205

Arg Arg Thr Asp Asp Tyr Leu Ser Lys Leu Val Thr Val Lys Ser Tyr
    210                 215                 220

Ile Glu Glu Lys Lys Ser Asp Leu Asp Ala Ala Met Lys Ile Ala Lys
225                 230                 235                 240

Glu Leu Arg Ser Ala Pro Ser Leu Arg Thr Tyr Cys Asp Leu Thr Gln
                245                 250                 255

Ile Ile Arg Thr Leu Lys Leu Thr Phe Glu Ser Glu Leu Ser Gln Val
            260                 265                 270

Ser Ser Ile Ile Pro Arg Asn Thr Pro Arg Leu Asp Ile Asn Cys Ser
        275                 280                 285

Glu Ala Ile Cys Met Phe Ser Ser Met Gly Lys Ile Glu Phe Glu Asp
    290                 295                 300

Ser Thr Lys Cys Tyr Pro Gln Glu Asn Glu Asp Gly Gln Asn Val Gln
305                 310                 315                 320

Lys Lys Phe Asn Asn Arg Lys Glu Leu Cys Cys Asp Val Tyr Ser Ser
                325                 330                 335

Leu Glu Lys Lys Lys Val Asp Ala Ala Val Leu Thr Asp Glu Thr Pro
            340                 345                 350

Glu Pro Pro Leu Gln Ala Glu Ala Pro Asp Arg His Leu Glu Gly Lys
        355                 360                 365

Lys Lys Gln Pro Thr Lys Glu Met Val Val Val Thr Ser Pro Lys Thr
    370                 375                 380

Ile Ala Val Leu Pro Gln Leu Gly Ser Ser Pro Asp Val Ile Ile Glu
385                 390                 395                 400

Glu Ile Ile Glu Glu Asn Leu Glu Ser Cys Phe Thr Asp Asp Pro Ile
```

-continued

```
                405                 410                 415

Glu Thr Ser Gly Tyr Pro Lys Lys Pro Pro Gln Lys Glu Gln Ser Ala
            420                 425                 430

Pro Val Gly Ser Lys Ala Gly Cys Pro Glu Leu Val Phe Val Ser His
        435                 440                 445

Val Ile His Pro Cys His Phe Tyr Val Arg Lys Tyr Ser Gln Ile Lys
    450                 455                 460

Asp Ala Thr Ile Leu Glu Lys Lys Met Lys Gln Val Cys Asn Arg Ser
465                 470                 475                 480

Leu His Leu Asp Pro Ser Asp Ile Leu Glu Leu Gly Ala Arg Ile Phe
                485                 490                 495

Val Asn Ser Ile Lys Asn Arg Met Trp Cys Arg Gly Ile Ile Thr Glu
            500                 505                 510

Ile Ile Pro Ser Lys Thr Lys Asn Ile Arg Lys Pro Cys Ser Pro Thr
        515                 520                 525

Lys Phe Ser Val Cys Glu Ile Ser Leu Ile Gln Ile Phe Met Val Asp
    530                 535                 540

Phe Gly Asn Ser Glu Val Leu Ile Ile Thr Gly Val Gly Asp Thr His
545                 550                 555                 560

Glu Gly Pro Glu His Asp Gly Glu Gln His Ile Thr Leu Ser Asp Phe
                565                 570                 575

Cys Leu Leu Leu Met Lys Ser Glu Pro Tyr Ser Glu Glu Leu Leu Lys
            580                 585                 590

Asp Ile Pro His Leu Ala His Leu Cys Ser Leu Lys Asp Ile Val Pro
        595                 600                 605

Tyr Asn Ser Thr Glu Gly Trp Glu Lys Glu Ala Lys Val Glu Phe Leu
    610                 615                 620

Lys Met Val Asn Lys Lys Ala Val Leu Met Lys Val Phe Gly Glu Glu
625                 630                 635                 640

Asp Asp Val Leu Ile Val Asp Leu Gln Lys Pro Pro Thr Asn Lys Ile
                645                 650                 655

Ser Ser Asp Met Pro Val Ser Leu Arg Asp Ala Leu Val Phe Met Glu
            660                 665                 670

Leu Ala Arg Phe Arg Ser Gln Ser Pro Arg Ser His Ser Glu Lys Asn
        675                 680                 685

Thr Thr Leu Cys Tyr His Pro Pro Ile Leu Pro Glu Glu Met Thr Glu
    690                 695                 700

Val Ser Val Met Val Cys His Ile Asn Ser Pro Thr Asp Phe Tyr Leu
705                 710                 715                 720

Gln Leu Met Glu Asn Leu Asp Phe Leu Ser Leu Leu Lys Thr Ile Glu
                725                 730                 735

Glu Phe Tyr Lys Gly Glu Asp Gly Glu Asn Leu Glu Ile Leu Cys Pro
            740                 745                 750

Leu Gln Asn Gln Ala Cys Val Ala Lys Phe Glu Asp Gly Ile Trp Tyr
        755                 760                 765

Arg Ala Lys Val Ile Gly Leu Pro Gly His Arg Glu Val Glu Val Lys
    770                 775                 780

Tyr Val Asp Phe Gly Asn Thr Ala Lys Ile Thr Leu Lys Asp Met Arg
785                 790                 795                 800

Lys Ile Lys Asp Glu Phe Leu Glu Pro Pro Glu Lys Ala Ile Lys Cys
                805                 810                 815

Lys Leu Ala Tyr Val Glu Pro Ser Lys Lys Ser Gln Trp Ser Lys Lys
            820                 825                 830
```

-continued

```
Ala Lys Glu Lys Phe Glu Glu Lys Thr Gln Asp Lys Phe Val Thr Cys
        835                 840                 845

Ser Val Ile Lys Ile Leu Glu Asn Asn Val Leu Leu Val Glu Leu Phe
    850                 855                 860

Asp Ser Arg Ala Pro Gly Lys Ser Ala Val Ser Ile Asn Asp Gln Leu
865                 870                 875                 880

Val Lys Glu Gly Leu Ala Ser Tyr Glu Ala Gly Tyr Thr Leu Lys Asp
                885                 890                 895

Asn Ser Lys Lys His Leu Glu Val Trp Asp Pro Ser Pro Glu Glu Ile
            900                 905                 910

Ile Thr Ser Glu Ile Asn Asn Leu Ser Pro Leu Ser Val Lys Ser Leu
        915                 920                 925

Pro Asn Glu Asn Phe Gln Ser Leu Tyr Asn Lys Glu Leu Pro Val Asn
    930                 935                 940

Ile Cys Asn Val Ile Ser Pro Glu Lys Ile Tyr Val Gln Trp Leu Leu
945                 950                 955                 960

Thr Glu Asn Leu Leu Asn Ser Leu Glu Glu Lys Met Val Ala Ala Tyr
                965                 970                 975

Glu His Ser Glu Trp Lys Pro Val Lys Trp Glu Cys Asp Met His Cys
            980                 985                 990

Ala Val Lys Val Pro Ala Lys Asn  Gln Trp Arg Arg Gly  Gln Ile Leu
        995                 1000                1005

Arg Met  Val Thr Asp Lys Leu  Val Glu Val Leu Leu  Tyr Asp Val
    1010                1015                1020

Gly Val  Glu Leu Val Val Asn  Ile His Cys Leu Arg  Glu Leu Gln
    1025                1030                1035

Glu Asn  Leu Lys Thr Met Gly  Arg Leu Ser Leu Glu  Cys Ser Leu
    1040                1045                1050

Val Asp  Ile Arg Pro Thr Gly  Gly Ser Asp Lys Trp  Thr Ala Thr
    1055                1060                1065

Ala Cys  Asp Cys Leu Ser Leu  Tyr Leu Thr Gly Ala  Ile Ala Thr
    1070                1075                1080

Ile Ile  Leu Gln Glu Ser Asn  Thr Thr Trp Pro Leu  Pro Val Lys
    1085                1090                1095

Ile Phe  Cys Arg Asp Glu Lys  Gly Glu Arg Val Asp  Val Ser Lys
    1100                1105                1110

Tyr Leu  Ile Lys Lys Gly Leu  Ala Leu Arg Glu Arg  Arg Ala Ser
    1115                1120                1125

Ser Ser
    1130


<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19

caccatggag actgctggag acaagaag                                          28


<210> SEQ ID NO 20
<211> LENGTH: 25
<212> TYPE: DNA
<213> ORGANISM: Artificial
<220> FEATURE:
```

<223> OTHER INFORMATION: primer

<400> SEQUENCE: 20
ggacctattc cagaggaact gtcac 25

<210> SEQ ID NO 21
<211> LENGTH: 28
<212> TYPE: DNA
<213> ORGANISM: Artificial
<220> FEATURE:
<223> OTHER INFORMATION: primer

<400> SEQUENCE: 21
caccatgtca tacttcggcc tggagact 28

<210> SEQ ID NO 22
<211> LENGTH: 27
<212> TYPE: DNA
<213> ORGANISM: Artificial
<220> FEATURE:
<223> OTHER INFORMATION: primer

<400> SEQUENCE: 22
actctactct tttctccttt ggcaccc 27

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
caccatggcg gcagaggctt cgtcgaccgg 30

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
ctaaaactcc acagcctttg agggagaatc 30

<210> SEQ ID NO 25
<211> LENGTH: 27
<212> TYPE: DNA
<213> ORGANISM: Artificial
<220> FEATURE:
<223> OTHER INFORMATION: primer

<400> SEQUENCE: 25
caccatgaag tctgaaccat acagtga 27

<210> SEQ ID NO 26
<211> LENGTH: 27
<212> TYPE: DNA
<213> ORGANISM: Artificial
<220> FEATURE:
<223> OTHER INFORMATION: primer

<400> SEQUENCE: 26
ttaggaggag gaggcccttc tctctct 27

<210> SEQ ID NO 27
<211> LENGTH: 27
<212> TYPE: DNA
<213> ORGANISM: Artificial
<220> FEATURE:
<223> OTHER INFORMATION: primer

<400> SEQUENCE: 27
gaccgggctg gcttcctgtc acctagt 27

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28
tttaccattt tcggtggcaa ggcttcc 27

<210> SEQ ID NO 29
<211> LENGTH: 27
<212> TYPE: DNA
<213> ORGANISM: Artificial
<220> FEATURE:
<223> OTHER INFORMATION: primer

<400> SEQUENCE: 29
aagctggcat atgttgaacc aagtaaa 27

<210> SEQ ID NO 30
<211> LENGTH: 27
<212> TYPE: DNA
<213> ORGANISM: Artificial
<220> FEATURE:
<223> OTHER INFORMATION: primer

<400> SEQUENCE: 30
ttcataagat gctaggccct ctttcac 27

<210> SEQ ID NO 31
<211> LENGTH: 27
<212> TYPE: DNA
<213> ORGANISM: Artificial
<220> FEATURE:
<223> OTHER INFORMATION: primer

<400> SEQUENCE: 31
caccatggcg gcagaggctt cgaagac 27

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
ttattcatct ttatctgcaa gccccattt 29

<210> SEQ ID NO 33
<211> LENGTH: 4797
<212> TYPE: DNA
<213> ORGANISM: Homo sapiens
<220> FEATURE:
<221> NAME/KEY: CDS
<222> LOCATION: (1)..(4794)

```
<400> SEQUENCE: 33

atg gcg gca gag gct tcg aag act ggg cct tct agg tct tcc tac cag       48
Met Ala Ala Glu Ala Ser Lys Thr Gly Pro Ser Arg Ser Ser Tyr Gln
1               5                   10                  15

cga atg ggg agg aag agt cag ccc tgg ggt gcc gct gaa atc cag tgc       96
Arg Met Gly Arg Lys Ser Gln Pro Trp Gly Ala Ala Glu Ile Gln Cys
            20                  25                  30

acc agg tgt gga agg agg gta tcc aga tca tcc ggt cac cat tgt gaa      144
Thr Arg Cys Gly Arg Arg Val Ser Arg Ser Ser Gly His His Cys Glu
        35                  40                  45

ctt caa tgt gga cat gct ttt tgt gaa cta tgc ttg tta atg act gaa      192
Leu Gln Cys Gly His Ala Phe Cys Glu Leu Cys Leu Leu Met Thr Glu
    50                  55                  60

gaa tgc acc aca att ata tgc cct gat tgt gag gtt gct aca gct gta      240
Glu Cys Thr Thr Ile Ile Cys Pro Asp Cys Glu Val Ala Thr Ala Val
65                  70                  75                  80

aat act aga caa cgc tac tac cca atg gct gga tat att aag gaa gac      288
Asn Thr Arg Gln Arg Tyr Tyr Pro Met Ala Gly Tyr Ile Lys Glu Asp
                85                  90                  95

tcc ata atg gaa aaa ctg cag cct aag acg ata aag aat tgt tct cag      336
Ser Ile Met Glu Lys Leu Gln Pro Lys Thr Ile Lys Asn Cys Ser Gln
            100                 105                 110

gac ttt aag aag act gct gat cag cta act act ggt tta gaa cgt tca      384
Asp Phe Lys Lys Thr Ala Asp Gln Leu Thr Thr Gly Leu Glu Arg Ser
        115                 120                 125

gcc tcc aca gac aag act ctt ttg aac tca tca gct gta atg ttg gac      432
Ala Ser Thr Asp Lys Thr Leu Leu Asn Ser Ser Ala Val Met Leu Asp
    130                 135                 140

act aat act gca gaa gaa att gat gaa gca ttg aat aca gca cac cat      480
Thr Asn Thr Ala Glu Glu Ile Asp Glu Ala Leu Asn Thr Ala His His
145                 150                 155                 160

agt ttc gaa cag tta agc att gct gga aaa gca ctt gaa cac atg cag      528
Ser Phe Glu Gln Leu Ser Ile Ala Gly Lys Ala Leu Glu His Met Gln
                165                 170                 175

aag caa acg ata gag gaa aga gaa aga gtt ata gaa gtt gtg gag aaa      576
Lys Gln Thr Ile Glu Glu Arg Glu Arg Val Ile Glu Val Val Glu Lys
            180                 185                 190

cag ttt gac caa ctt ttg gct ttt ttt gat tcc agg aaa aag aac ctg      624
Gln Phe Asp Gln Leu Leu Ala Phe Phe Asp Ser Arg Lys Lys Asn Leu
        195                 200                 205

tgt gaa gaa ttt gca aga act act gat gat tat cta tca aat tta ata      672
Cys Glu Glu Phe Ala Arg Thr Thr Asp Asp Tyr Leu Ser Asn Leu Ile
    210                 215                 220

aag gct aaa agc tac att gaa gag aaa aaa aat aat ttg aat gca gct      720
Lys Ala Lys Ser Tyr Ile Glu Glu Lys Lys Asn Asn Leu Asn Ala Ala
225                 230                 235                 240

atg aac ata gca aga gca tta caa tta tcg cct tct cta aga aca tac      768
Met Asn Ile Ala Arg Ala Leu Gln Leu Ser Pro Ser Leu Arg Thr Tyr
                245                 250                 255

tgt gac ctg aat cag att atc cgg act ttg cag tta act tca gat agt      816
Cys Asp Leu Asn Gln Ile Ile Arg Thr Leu Gln Leu Thr Ser Asp Ser
            260                 265                 270

gaa tta gca caa gtt agt tct cca caa cta agg aac cct ccc agg ttg      864
Glu Leu Ala Gln Val Ser Ser Pro Gln Leu Arg Asn Pro Pro Arg Leu
        275                 280                 285

agt gtg aat tgc agt gag atc atc tgt atg ttc aac aat atg gga aag      912
Ser Val Asn Cys Ser Glu Ile Ile Cys Met Phe Asn Asn Met Gly Lys
    290                 295                 300
```

-continued

```
att gaa ttt agg gac tca aca aaa tgt tat ccc caa gaa aat gaa att      960
Ile Glu Phe Arg Asp Ser Thr Lys Cys Tyr Pro Gln Glu Asn Glu Ile
305                 310                 315                 320

aga cag aat gtt caa aag aaa tat aat aac aaa aag gaa ctt tct tgt     1008
Arg Gln Asn Val Gln Lys Lys Tyr Asn Asn Lys Lys Glu Leu Ser Cys
                325                 330                 335

tac gat aca tac cca ccg cta gaa aag aaa aag gtt gac atg tct gtc     1056
Tyr Asp Thr Tyr Pro Pro Leu Glu Lys Lys Lys Val Asp Met Ser Val
            340                 345                 350

cta acc agt gaa gca cca cca cct cct ttg caa cct gag aca aat gat     1104
Leu Thr Ser Glu Ala Pro Pro Pro Pro Leu Gln Pro Glu Thr Asn Asp
        355                 360                 365

gta cat tta gaa gca aaa aac ttc cag cca cag aaa gac gtt gca aca     1152
Val His Leu Glu Ala Lys Asn Phe Gln Pro Gln Lys Asp Val Ala Thr
    370                 375                 380

gca tcc cct aaa acc att gct gtg tta cct cag atg gga tct agc cct     1200
Ala Ser Pro Lys Thr Ile Ala Val Leu Pro Gln Met Gly Ser Ser Pro
385                 390                 395                 400

gat gtg ata att gaa gaa att att gaa gac aac gtg gaa agt tct gca     1248
Asp Val Ile Ile Glu Glu Ile Ile Glu Asp Asn Val Glu Ser Ser Ala
                405                 410                 415

gag cta gtt ttt gta agc cat gta ata gat cct tgc cat ttc tac att     1296
Glu Leu Val Phe Val Ser His Val Ile Asp Pro Cys His Phe Tyr Ile
            420                 425                 430

cgg aag tat tca caa ata aaa gac gcc aaa gta ctg gag aag aag gtg     1344
Arg Lys Tyr Ser Gln Ile Lys Asp Ala Lys Val Leu Glu Lys Lys Val
        435                 440                 445

aat gaa ttt tgc aat agg agt tca cac ctt gat cct tca gac att ttg     1392
Asn Glu Phe Cys Asn Arg Ser Ser His Leu Asp Pro Ser Asp Ile Leu
    450                 455                 460

gaa cta ggt gca aga ata ttt gtc agc agt att aaa aat gga atg tgg     1440
Glu Leu Gly Ala Arg Ile Phe Val Ser Ser Ile Lys Asn Gly Met Trp
465                 470                 475                 480

tgt cga gga act atc aca gaa tta att cca ata gag ggt aga aat acc     1488
Cys Arg Gly Thr Ile Thr Glu Leu Ile Pro Ile Glu Gly Arg Asn Thr
                485                 490                 495

aga aaa cct tgt agt cca acc aga tta ttt gtc cat gaa gtt gca cta     1536
Arg Lys Pro Cys Ser Pro Thr Arg Leu Phe Val His Glu Val Ala Leu
            500                 505                 510

ata caa ata ttc atg gta gat ttt gga aat tct gaa gtc ctg att gtc     1584
Ile Gln Ile Phe Met Val Asp Phe Gly Asn Ser Glu Val Leu Ile Val
        515                 520                 525

act gga gtt gtt gat acc cat gtg aga cca gaa cac tct gct aag caa     1632
Thr Gly Val Val Asp Thr His Val Arg Pro Glu His Ser Ala Lys Gln
    530                 535                 540

cat att gca cta aat gat tta tgt ctg gtt cta agg aaa tct gaa cca     1680
His Ile Ala Leu Asn Asp Leu Cys Leu Val Leu Arg Lys Ser Glu Pro
545                 550                 555                 560

tat act gaa ggg ctg cta aaa gac atc cag cca tta gca caa cca tgc     1728
Tyr Thr Glu Gly Leu Leu Lys Asp Ile Gln Pro Leu Ala Gln Pro Cys
                565                 570                 575

tca ttg aaa gac att gtt cca cag aat tca aat gaa ggc tgg gaa gag     1776
Ser Leu Lys Asp Ile Val Pro Gln Asn Ser Asn Glu Gly Trp Glu Glu
            580                 585                 590

gaa gct aaa gtg gaa ttt ttg aaa atg gta aat aac aag gct gtt tca     1824
Glu Ala Lys Val Glu Phe Leu Lys Met Val Asn Asn Lys Ala Val Ser
        595                 600                 605

atg aaa gtt ttt aga gaa gaa gat ggt gtg ctt att gta gat ctg caa     1872
Met Lys Val Phe Arg Glu Glu Asp Gly Val Leu Ile Val Asp Leu Gln
    610                 615                 620
```

-continued

```
aaa cca cca ccg aat aaa ata agc agt gat atg cct gtg tct ctt aga      1920
Lys Pro Pro Pro Asn Lys Ile Ser Ser Asp Met Pro Val Ser Leu Arg
625                 630                 635                 640

gat gcg cta gtt ttt atg gaa cta gca aag ttt aag tca caa tca cta      1968
Asp Ala Leu Val Phe Met Glu Leu Ala Lys Phe Lys Ser Gln Ser Leu
                645                 650                 655

aga agt cac ttt gaa aaa aat act act tta cac tat cat cca cct att      2016
Arg Ser His Phe Glu Lys Asn Thr Thr Leu His Tyr His Pro Pro Ile
            660                 665                 670

ttg cct aaa gaa atg aca gat gtt tca gta acg gtt tgt cat ata aat      2064
Leu Pro Lys Glu Met Thr Asp Val Ser Val Thr Val Cys His Ile Asn
        675                 680                 685

agt cct gga gat ttc tat ctt cag ttg ata gag ggc ctg gat att tta      2112
Ser Pro Gly Asp Phe Tyr Leu Gln Leu Ile Glu Gly Leu Asp Ile Leu
    690                 695                 700

ttt cta tta aag aca atc gag gaa ttc tat aaa agt gaa gat gga gaa      2160
Phe Leu Leu Lys Thr Ile Glu Glu Phe Tyr Lys Ser Glu Asp Gly Glu
705                 710                 715                 720

aat ctg gaa atc ctc tgt cca gtt caa gat caa gcc tgt gta gct aaa      2208
Asn Leu Glu Ile Leu Cys Pro Val Gln Asp Gln Ala Cys Val Ala Lys
                725                 730                 735

ttt gaa gat gga att tgg tac cga gca aaa gtt atc gga ttg cct gga      2256
Phe Glu Asp Gly Ile Trp Tyr Arg Ala Lys Val Ile Gly Leu Pro Gly
            740                 745                 750

cat cag gaa gtt gaa gtt aaa tat gtg gac ttt ggt aat act gca aaa      2304
His Gln Glu Val Glu Val Lys Tyr Val Asp Phe Gly Asn Thr Ala Lys
        755                 760                 765

ata aca atc aaa gac gtg cgt aaa ata aag gat gag ttt ctg aat gcc      2352
Ile Thr Ile Lys Asp Val Arg Lys Ile Lys Asp Glu Phe Leu Asn Ala
    770                 775                 780

cca gag aag gca att aaa tgt aag ttg gcc tat att gaa cca tat aaa      2400
Pro Glu Lys Ala Ile Lys Cys Lys Leu Ala Tyr Ile Glu Pro Tyr Lys
785                 790                 795                 800

agg aca atg cag tgg tcc aaa gaa gct aaa gaa aaa ttt gaa gaa aag      2448
Arg Thr Met Gln Trp Ser Lys Glu Ala Lys Glu Lys Phe Glu Glu Lys
                805                 810                 815

gct caa gat aaa ttt atg aca tgt tca gtt atc aaa att ctg gaa gat      2496
Ala Gln Asp Lys Phe Met Thr Cys Ser Val Ile Lys Ile Leu Glu Asp
            820                 825                 830

aat gtg ctc tta gtt gag ctt ttc gat tct ctt ggt gct cct gaa atg      2544
Asn Val Leu Leu Val Glu Leu Phe Asp Ser Leu Gly Ala Pro Glu Met
        835                 840                 845

act act act agt att aat gac cag cta gtt aaa gag ggc cta gca tct      2592
Thr Thr Thr Ser Ile Asn Asp Gln Leu Val Lys Glu Gly Leu Ala Ser
    850                 855                 860

tat gaa ata gga tac atc ctc aaa gat aat tct caa aag cat att gaa      2640
Tyr Glu Ile Gly Tyr Ile Leu Lys Asp Asn Ser Gln Lys His Ile Glu
865                 870                 875                 880

gtt tgg gat cct tct cca gaa gaa att att tca aat gaa gta cac aac      2688
Val Trp Asp Pro Ser Pro Glu Glu Ile Ile Ser Asn Glu Val His Asn
                885                 890                 895

tta aat cct gtg tct gca aaa tct cta cct aat gag aat ttt cag tca      2736
Leu Asn Pro Val Ser Ala Lys Ser Leu Pro Asn Glu Asn Phe Gln Ser
            900                 905                 910

ctt tat aat aag gaa ttg cct gtg cat atc tgt aat gta ata tct cct      2784
Leu Tyr Asn Lys Glu Leu Pro Val His Ile Cys Asn Val Ile Ser Pro
        915                 920                 925

gag aag att tat gtt cag tgg ttg tta act gaa aac tta ctt aat agt      2832
Glu Lys Ile Tyr Val Gln Trp Leu Leu Thr Glu Asn Leu Leu Asn Ser
```

-continued

```
930                 935                 940

tta gaa gaa aag atg ata gct gct tat gaa aac tca aaa tgg gaa cct     2880
Leu Glu Glu Lys Met Ile Ala Ala Tyr Glu Asn Ser Lys Trp Glu Pro
945                 950                 955                 960

gtt aaa tgg gaa aat gat atg cac tgt gct att aag atc caa gat aaa     2928
Val Lys Trp Glu Asn Asp Met His Cys Ala Ile Lys Ile Gln Asp Lys
            965                 970                 975

aat cag tgg cga aga ggc cag atc atc aga atg gtt aca gac aca ttg     2976
Asn Gln Trp Arg Arg Gly Gln Ile Ile Arg Met Val Thr Asp Thr Leu
        980                 985                 990

gta gag gtc ttg ctg tat gat gtg  ggt gtt gaa cta gta  gtg aat gtt    3024
Val Glu Val Leu Leu Tyr Asp Val  Gly Val Glu Leu Val  Val Asn Val
    995                 1000                1005

gac tgt  tta aga aaa ctt gaa  gaa aat cta aag aca  atg gga aga      3069
Asp Cys  Leu Arg Lys Leu Glu  Glu Asn Leu Lys Thr  Met Gly Arg
    1010                1015                1020

ctc tct  ttg gaa tgt tct ctg  gtt gac ata aga cca  gct ggt ggg      3114
Leu Ser  Leu Glu Cys Ser Leu  Val Asp Ile Arg Pro  Ala Gly Gly
    1025                1030                1035

agt gac  aag tgg aca gca aca  gct tgt gac tgt ctt  tca ttg tac      3159
Ser Asp  Lys Trp Thr Ala Thr  Ala Cys Asp Cys Leu  Ser Leu Tyr
    1040                1045                1050

ctg act  gga gct gta gca act  ata atc tta cag gtg  gat agt gag      3204
Leu Thr  Gly Ala Val Ala Thr  Ile Ile Leu Gln Val  Asp Ser Glu
    1055                1060                1065

gaa aac  aac aca aca tgg cca  tta cct gtg aaa att  ttc tgc aga      3249
Glu Asn  Asn Thr Thr Trp Pro  Leu Pro Val Lys Ile  Phe Cys Arg
    1070                1075                1080

gat gaa  aaa gga gag cgt gtt  gat gtt tct aaa tat  ttg att aaa      3294
Asp Glu  Lys Gly Glu Arg Val  Asp Val Ser Lys Tyr  Leu Ile Lys
    1085                1090                1095

aag ggt  ttg gct ttg aga gaa  agg aga att aat aac  tta gat aac      3339
Lys Gly  Leu Ala Leu Arg Glu  Arg Arg Ile Asn Asn  Leu Asp Asn
    1100                1105                1110

agc cat  tca tta tct gag aag  tct ctg gaa gtc ccc  ctg gaa cag      3384
Ser His  Ser Leu Ser Glu Lys  Ser Leu Glu Val Pro  Leu Glu Gln
    1115                1120                1125

gaa gat  tca gta gtt act aac  tgt att aaa act aac  ttt gac cct      3429
Glu Asp  Ser Val Val Thr Asn  Cys Ile Lys Thr Asn  Phe Asp Pro
    1130                1135                1140

gac aag  aaa act gct gac ata  atc agt gaa cag aaa  gtg tct gaa      3474
Asp Lys  Lys Thr Ala Asp Ile  Ile Ser Glu Gln Lys  Val Ser Glu
    1145                1150                1155

ttt cag  gag aaa att cta gaa  cca aga acc act aga  ggg tat aag      3519
Phe Gln  Glu Lys Ile Leu Glu  Pro Arg Thr Thr Arg  Gly Tyr Lys
    1160                1165                1170

cca cca  gct att cct aac atg  aac gta ttt gag gca  aca gtc agc      3564
Pro Pro  Ala Ile Pro Asn Met  Asn Val Phe Glu Ala  Thr Val Ser
    1175                1180                1185

tgt gtt  ggt gat gat gga act  ata ttt gta gta cct  aaa cta tca      3609
Cys Val  Gly Asp Asp Gly Thr  Ile Phe Val Val Pro  Lys Leu Ser
    1190                1195                1200

gaa ttt  gag cta ata aaa atg  aca aat gaa att caa  agt aat tta      3654
Glu Phe  Glu Leu Ile Lys Met  Thr Asn Glu Ile Gln  Ser Asn Leu
    1205                1210                1215

aaa tgc  ctt ggt ctt ttg gag  cct tat ttc tgg aaa  aaa gga gaa      3699
Lys Cys  Leu Gly Leu Leu Glu  Pro Tyr Phe Trp Lys  Lys Gly Glu
    1220                1225                1230

gca tgt  gca gta aga gga tcc  gat act ctg tgg tat  cgt ggc aag      3744
```

-continued

```
Ala Cys  Ala Val Arg Gly Ser  Asp Thr Leu Trp Tyr  Arg Gly Lys
    1235                 1240                 1245

gtg atg  gag gtt gta ggt ggc  gct gtc aga gta caa  tat tta gat      3789
Val Met  Glu Val Val Gly Gly  Ala Val Arg Val Gln  Tyr Leu Asp
    1250                 1255                 1260

cat gga  ttc act gaa aag att  ccg cag tgc cat ctt  tac cct att      3834
His Gly  Phe Thr Glu Lys Ile  Pro Gln Cys His Leu  Tyr Pro Ile
    1265                 1270                 1275

ttg ctg  tat cct gat ata ccc  cag ttt tgt att cct  tgt cag ctc      3879
Leu Leu  Tyr Pro Asp Ile Pro  Gln Phe Cys Ile Pro  Cys Gln Leu
    1280                 1285                 1290

cat aat  acc aca cct gtt ggg  aat gtc tgg caa cca  gat gca ata      3924
His Asn  Thr Thr Pro Val Gly  Asn Val Trp Gln Pro  Asp Ala Ile
    1295                 1300                 1305

gaa gtt  ctt caa caa ctg ctt  tca aag aga cag gtg  gac att cac      3969
Glu Val  Leu Gln Gln Leu Leu  Ser Lys Arg Gln Val  Asp Ile His
    1310                 1315                 1320

att atg  gca tac tat aaa tac  tgt act tct gaa cat  acc gag gag      4014
Ile Met  Ala Tyr Tyr Lys Tyr  Cys Thr Ser Glu His  Thr Glu Glu
    1325                 1330                 1335

atg ttg  aaa gaa aaa cca aga  tca gat cat gat aaa  aag tat gaa      4059
Met Leu  Lys Glu Lys Pro Arg  Ser Asp His Asp Lys  Lys Tyr Glu
    1340                 1345                 1350

gag gaa  caa tgg gaa ata agg  ttt gag gaa ttg ctt  tcg gct gaa      4104
Glu Glu  Gln Trp Glu Ile Arg  Phe Glu Glu Leu Leu  Ser Ala Glu
    1355                 1360                 1365

aca gac  act cct ctt tta cca  cca tat ttg tct tca  tct ctg cct      4149
Thr Asp  Thr Pro Leu Leu Pro  Pro Tyr Leu Ser Ser  Ser Leu Pro
    1370                 1375                 1380

tcc cca  gga gaa ctc tat gct  gtt caa gtt aag cac  gtt gtc tca      4194
Ser Pro  Gly Glu Leu Tyr Ala  Val Gln Val Lys His  Val Val Ser
    1385                 1390                 1395

cct aat  gaa gtg tat att tgc  ctt gat tct ata gaa  act tct aac      4239
Pro Asn  Glu Val Tyr Ile Cys  Leu Asp Ser Ile Glu  Thr Ser Asn
    1400                 1405                 1410

cag tct  aac cag cat agt gac  aca gat gat agt gga  gtc agc ggg      4284
Gln Ser  Asn Gln His Ser Asp  Thr Asp Asp Ser Gly  Val Ser Gly
    1415                 1420                 1425

gaa tca  gaa tcc gag agc ctt  gat gaa gca ctg cag  agg gtt aat      4329
Glu Ser  Glu Ser Glu Ser Leu  Asp Glu Ala Leu Gln  Arg Val Asn
    1430                 1435                 1440

aag aag  gta gag gcg ctt cct  cct ctg acg gat ttt  aga aca gaa      4374
Lys Lys  Val Glu Ala Leu Pro  Pro Leu Thr Asp Phe  Arg Thr Glu
    1445                 1450                 1455

atg cct  tgc ctt gca gaa tat  gat gat ggc tta tgg  tat aga gcg      4419
Met Pro  Cys Leu Ala Glu Tyr  Asp Asp Gly Leu Trp  Tyr Arg Ala
    1460                 1465                 1470

aag att  gtt gcc att aaa gaa  ttt aat cct tta tct  atc tta gta      4464
Lys Ile  Val Ala Ile Lys Glu  Phe Asn Pro Leu Ser  Ile Leu Val
    1475                 1480                 1485

caa ttt  gtt gat tat gga tca  act gca aag ctg aca  tta aac aga      4509
Gln Phe  Val Asp Tyr Gly Ser  Thr Ala Lys Leu Thr  Leu Asn Arg
    1490                 1495                 1500

ctg tgc  caa att cct tct cat  ctt atg cgg tat cca  gct cga gcc      4554
Leu Cys  Gln Ile Pro Ser His  Leu Met Arg Tyr Pro  Ala Arg Ala
    1505                 1510                 1515

ata aag  gtt ctc ttg gca ggg  ttt aaa cct ccc tta  agg gat cta      4599
Ile Lys  Val Leu Leu Ala Gly  Phe Lys Pro Pro Leu  Arg Asp Leu
    1520                 1525                 1530
```

-continued

```
ggg gag  aca aga ata cca tat  tgt ccc aaa tgg agc  atg gag gca      4644
Gly Glu  Thr Arg Ile Pro Tyr  Cys Pro Lys Trp Ser  Met Glu Ala
    1535                 1540                 1545

ctg tgg  gct atg ata gac tgt  ctt caa gga aaa caa  ctc tat gct      4689
Leu Trp  Ala Met Ile Asp Cys  Leu Gln Gly Lys Gln  Leu Tyr Ala
    1550                 1555                 1560

gtg tcc  atg gct cca gca cca  gaa cag ata gtg aca  tta tat gac      4734
Val Ser  Met Ala Pro Ala Pro  Glu Gln Ile Val Thr  Leu Tyr Asp
    1565                 1570                 1575

gat gaa  cag cat cca gtt cat  atg ccg ttg gta gaa  atg ggg ctt      4779
Asp Glu  Gln His Pro Val His  Met Pro Leu Val Glu  Met Gly Leu
    1580                 1585                 1590

gca gat  aaa gat gaa taa                                            4797
Ala Asp  Lys Asp Glu
    1595
```

<210> SEQ ID NO 34
<211> LENGTH: 1598
<212> TYPE: PRT
<213> ORGANISM: Homo sapiens

<400> SEQUENCE: 34

```
Met Ala Ala Glu Ala Ser Lys Thr Gly Pro Ser Arg Ser Ser Tyr Gln
1               5                   10                  15

Arg Met Gly Arg Lys Ser Gln Pro Trp Gly Ala Ala Glu Ile Gln Cys
            20                  25                  30

Thr Arg Cys Gly Arg Arg Val Ser Arg Ser Ser Gly His His Cys Glu
        35                  40                  45

Leu Gln Cys Gly His Ala Phe Cys Glu Leu Cys Leu Leu Met Thr Glu
    50                  55                  60

Glu Cys Thr Thr Ile Ile Cys Pro Asp Cys Glu Val Ala Thr Ala Val
65                  70                  75                  80

Asn Thr Arg Gln Arg Tyr Tyr Pro Met Ala Gly Tyr Ile Lys Glu Asp
                85                  90                  95

Ser Ile Met Glu Lys Leu Gln Pro Lys Thr Ile Lys Asn Cys Ser Gln
            100                 105                 110

Asp Phe Lys Lys Thr Ala Asp Gln Leu Thr Thr Gly Leu Glu Arg Ser
        115                 120                 125

Ala Ser Thr Asp Lys Thr Leu Leu Asn Ser Ser Ala Val Met Leu Asp
    130                 135                 140

Thr Asn Thr Ala Glu Glu Ile Asp Glu Ala Leu Asn Thr Ala His His
145                 150                 155                 160

Ser Phe Glu Gln Leu Ser Ile Ala Gly Lys Ala Leu Glu His Met Gln
                165                 170                 175

Lys Gln Thr Ile Glu Glu Arg Glu Arg Val Ile Glu Val Val Glu Lys
            180                 185                 190

Gln Phe Asp Gln Leu Leu Ala Phe Phe Asp Ser Arg Lys Lys Asn Leu
        195                 200                 205

Cys Glu Glu Phe Ala Arg Thr Thr Asp Asp Tyr Leu Ser Asn Leu Ile
    210                 215                 220

Lys Ala Lys Ser Tyr Ile Glu Glu Lys Lys Asn Asn Leu Asn Ala Ala
225                 230                 235                 240

Met Asn Ile Ala Arg Ala Leu Gln Leu Ser Pro Ser Leu Arg Thr Tyr
                245                 250                 255

Cys Asp Leu Asn Gln Ile Ile Arg Thr Leu Gln Leu Thr Ser Asp Ser
            260                 265                 270
```

-continued

```
Glu Leu Ala Gln Val Ser Ser Pro Gln Leu Arg Asn Pro Pro Arg Leu
        275                 280                 285

Ser Val Asn Cys Ser Glu Ile Ile Cys Met Phe Asn Asn Met Gly Lys
    290                 295                 300

Ile Glu Phe Arg Asp Ser Thr Lys Cys Tyr Pro Gln Glu Asn Glu Ile
305                 310                 315                 320

Arg Gln Asn Val Gln Lys Lys Tyr Asn Asn Lys Lys Glu Leu Ser Cys
                325                 330                 335

Tyr Asp Thr Tyr Pro Pro Leu Glu Lys Lys Lys Val Asp Met Ser Val
            340                 345                 350

Leu Thr Ser Glu Ala Pro Pro Pro Pro Leu Gln Pro Glu Thr Asn Asp
        355                 360                 365

Val His Leu Glu Ala Lys Asn Phe Gln Pro Gln Lys Asp Val Ala Thr
    370                 375                 380

Ala Ser Pro Lys Thr Ile Ala Val Leu Pro Gln Met Gly Ser Ser Pro
385                 390                 395                 400

Asp Val Ile Ile Glu Glu Ile Ile Glu Asp Asn Val Glu Ser Ser Ala
                405                 410                 415

Glu Leu Val Phe Val Ser His Val Ile Asp Pro Cys His Phe Tyr Ile
            420                 425                 430

Arg Lys Tyr Ser Gln Ile Lys Asp Ala Lys Val Leu Glu Lys Lys Val
        435                 440                 445

Asn Glu Phe Cys Asn Arg Ser Ser His Leu Asp Pro Ser Asp Ile Leu
    450                 455                 460

Glu Leu Gly Ala Arg Ile Phe Val Ser Ser Ile Lys Asn Gly Met Trp
465                 470                 475                 480

Cys Arg Gly Thr Ile Thr Glu Leu Ile Pro Ile Glu Gly Arg Asn Thr
                485                 490                 495

Arg Lys Pro Cys Ser Pro Thr Arg Leu Phe Val His Glu Val Ala Leu
            500                 505                 510

Ile Gln Ile Phe Met Val Asp Phe Gly Asn Ser Glu Val Leu Ile Val
        515                 520                 525

Thr Gly Val Val Asp Thr His Val Arg Pro Glu His Ser Ala Lys Gln
    530                 535                 540

His Ile Ala Leu Asn Asp Leu Cys Leu Val Leu Arg Lys Ser Glu Pro
545                 550                 555                 560

Tyr Thr Glu Gly Leu Leu Lys Asp Ile Gln Pro Leu Ala Gln Pro Cys
                565                 570                 575

Ser Leu Lys Asp Ile Val Pro Gln Asn Ser Asn Glu Gly Trp Glu Glu
            580                 585                 590

Glu Ala Lys Val Glu Phe Leu Lys Met Val Asn Asn Lys Ala Val Ser
        595                 600                 605

Met Lys Val Phe Arg Glu Glu Asp Gly Val Leu Ile Val Asp Leu Gln
    610                 615                 620

Lys Pro Pro Pro Asn Lys Ile Ser Ser Asp Met Pro Val Ser Leu Arg
625                 630                 635                 640

Asp Ala Leu Val Phe Met Glu Leu Ala Lys Phe Lys Ser Gln Ser Leu
                645                 650                 655

Arg Ser His Phe Glu Lys Asn Thr Thr Leu His Tyr His Pro Pro Ile
            660                 665                 670

Leu Pro Lys Glu Met Thr Asp Val Ser Val Thr Val Cys His Ile Asn
        675                 680                 685

Ser Pro Gly Asp Phe Tyr Leu Gln Leu Ile Glu Gly Leu Asp Ile Leu
```

-continued

```
    690                 695                 700

Phe Leu Leu Lys Thr Ile Glu Glu Phe Tyr Lys Ser Glu Asp Gly Glu
705                 710                 715                 720

Asn Leu Glu Ile Leu Cys Pro Val Gln Asp Gln Ala Cys Val Ala Lys
                725                 730                 735

Phe Glu Asp Gly Ile Trp Tyr Arg Ala Lys Val Ile Gly Leu Pro Gly
            740                 745                 750

His Gln Glu Val Glu Val Lys Tyr Val Asp Phe Gly Asn Thr Ala Lys
        755                 760                 765

Ile Thr Ile Lys Asp Val Arg Lys Ile Lys Asp Glu Phe Leu Asn Ala
    770                 775                 780

Pro Glu Lys Ala Ile Lys Cys Lys Leu Ala Tyr Ile Glu Pro Tyr Lys
785                 790                 795                 800

Arg Thr Met Gln Trp Ser Lys Glu Ala Lys Glu Lys Phe Glu Glu Lys
                805                 810                 815

Ala Gln Asp Lys Phe Met Thr Cys Ser Val Ile Lys Ile Leu Glu Asp
            820                 825                 830

Asn Val Leu Leu Val Glu Leu Phe Asp Ser Leu Gly Ala Pro Glu Met
        835                 840                 845

Thr Thr Thr Ser Ile Asn Asp Gln Leu Val Lys Glu Gly Leu Ala Ser
    850                 855                 860

Tyr Glu Ile Gly Tyr Ile Leu Lys Asp Asn Ser Gln Lys His Ile Glu
865                 870                 875                 880

Val Trp Asp Pro Ser Pro Glu Glu Ile Ile Ser Asn Glu Val His Asn
                885                 890                 895

Leu Asn Pro Val Ser Ala Lys Ser Leu Pro Asn Glu Asn Phe Gln Ser
            900                 905                 910

Leu Tyr Asn Lys Glu Leu Pro Val His Ile Cys Asn Val Ile Ser Pro
        915                 920                 925

Glu Lys Ile Tyr Val Gln Trp Leu Leu Thr Glu Asn Leu Leu Asn Ser
    930                 935                 940

Leu Glu Glu Lys Met Ile Ala Ala Tyr Glu Asn Ser Lys Trp Glu Pro
945                 950                 955                 960

Val Lys Trp Glu Asn Asp Met His Cys Ala Ile Lys Ile Gln Asp Lys
                965                 970                 975

Asn Gln Trp Arg Arg Gly Gln Ile Ile Arg Met Val Thr Asp Thr Leu
            980                 985                 990

Val Glu Val Leu Leu Tyr Asp Val  Gly Val Glu Leu Val  Val Asn Val
        995                 1000                1005

Asp Cys  Leu Arg Lys Leu Glu  Glu Asn Leu Lys Thr  Met Gly Arg
    1010                1015                1020

Leu Ser  Leu Glu Cys Ser Leu  Val Asp Ile Arg Pro  Ala Gly Gly
    1025                1030                1035

Ser Asp  Lys Trp Thr Ala Thr  Ala Cys Asp Cys Leu  Ser Leu Tyr
    1040                1045                1050

Leu Thr  Gly Ala Val Ala Thr  Ile Ile Leu Gln Val  Asp Ser Glu
    1055                1060                1065

Glu Asn  Asn Thr Thr Trp Pro  Leu Pro Val Lys Ile  Phe Cys Arg
    1070                1075                1080

Asp Glu  Lys Gly Glu Arg Val  Asp Val Ser Lys Tyr  Leu Ile Lys
    1085                1090                1095

Lys Gly  Leu Ala Leu Arg Glu  Arg Arg Ile Asn Asn  Leu Asp Asn
    1100                1105                1110
```

```
Ser His  Ser Leu Ser Glu Lys  Ser Leu Glu Val Pro  Leu Glu Gln
    1115                 1120                 1125

Glu Asp  Ser Val Val Thr Asn  Cys Ile Lys Thr Asn  Phe Asp Pro
    1130                 1135                 1140

Asp Lys  Lys Thr Ala Asp Ile  Ile Ser Glu Gln Lys  Val Ser Glu
    1145                 1150                 1155

Phe Gln  Glu Lys Ile Leu Glu  Pro Arg Thr Thr Arg  Gly Tyr Lys
    1160                 1165                 1170

Pro Pro  Ala Ile Pro Asn Met  Asn Val Phe Glu Ala  Thr Val Ser
    1175                 1180                 1185

Cys Val  Gly Asp Asp Gly Thr  Ile Phe Val Val Pro  Lys Leu Ser
    1190                 1195                 1200

Glu Phe  Glu Leu Ile Lys Met  Thr Asn Glu Ile Gln  Ser Asn Leu
    1205                 1210                 1215

Lys Cys  Leu Gly Leu Leu Glu  Pro Tyr Phe Trp Lys  Lys Gly Glu
    1220                 1225                 1230

Ala Cys  Ala Val Arg Gly Ser  Asp Thr Leu Trp Tyr  Arg Gly Lys
    1235                 1240                 1245

Val Met  Glu Val Val Gly Gly  Ala Val Arg Val Gln  Tyr Leu Asp
    1250                 1255                 1260

His Gly  Phe Thr Glu Lys Ile  Pro Gln Cys His Leu  Tyr Pro Ile
    1265                 1270                 1275

Leu Leu  Tyr Pro Asp Ile Pro  Gln Phe Cys Ile Pro  Cys Gln Leu
    1280                 1285                 1290

His Asn  Thr Thr Pro Val Gly  Asn Val Trp Gln Pro  Asp Ala Ile
    1295                 1300                 1305

Glu Val  Leu Gln Gln Leu Leu  Ser Lys Arg Gln Val  Asp Ile His
    1310                 1315                 1320

Ile Met  Ala Tyr Tyr Lys Tyr  Cys Thr Ser Glu His  Thr Glu Glu
    1325                 1330                 1335

Met Leu  Lys Glu Lys Pro Arg  Ser Asp His Asp Lys  Lys Tyr Glu
    1340                 1345                 1350

Glu Glu  Gln Trp Glu Ile Arg  Phe Glu Glu Leu Leu  Ser Ala Glu
    1355                 1360                 1365

Thr Asp  Thr Pro Leu Leu Pro  Pro Tyr Leu Ser Ser  Ser Leu Pro
    1370                 1375                 1380

Ser Pro  Gly Glu Leu Tyr Ala  Val Gln Val Lys His  Val Val Ser
    1385                 1390                 1395

Pro Asn  Glu Val Tyr Ile Cys  Leu Asp Ser Ile Glu  Thr Ser Asn
    1400                 1405                 1410

Gln Ser  Asn Gln His Ser Asp  Thr Asp Asp Ser Gly  Val Ser Gly
    1415                 1420                 1425

Glu Ser  Glu Ser Glu Ser Leu  Asp Glu Ala Leu Gln  Arg Val Asn
    1430                 1435                 1440

Lys Lys  Val Glu Ala Leu Pro  Pro Leu Thr Asp Phe  Arg Thr Glu
    1445                 1450                 1455

Met Pro  Cys Leu Ala Glu Tyr  Asp Asp Gly Leu Trp  Tyr Arg Ala
    1460                 1465                 1470

Lys Ile  Val Ala Ile Lys Glu  Phe Asn Pro Leu Ser  Ile Leu Val
    1475                 1480                 1485

Gln Phe  Val Asp Tyr Gly Ser  Thr Ala Lys Leu Thr  Leu Asn Arg
    1490                 1495                 1500
```

-continued

```
Leu Cys  Gln Ile Pro Ser His  Leu Met Arg Tyr Pro  Ala Arg Ala
    1505                 1510                 1515

Ile Lys  Val Leu Leu Ala Gly  Phe Lys Pro Pro Leu  Arg Asp Leu
    1520                 1525                 1530

Gly Glu  Thr Arg Ile Pro Tyr  Cys Pro Lys Trp Ser  Met Glu Ala
    1535                 1540                 1545

Leu Trp  Ala Met Ile Asp Cys  Leu Gln Gly Lys Gln  Leu Tyr Ala
    1550                 1555                 1560

Val Ser  Met Ala Pro Ala Pro  Glu Gln Ile Val Thr  Leu Tyr Asp
    1565                 1570                 1575

Asp Glu  Gln His Pro Val His  Met Pro Leu Val Glu  Met Gly Leu
    1580                 1585                 1590

Ala Asp  Lys Asp Glu
    1595
```

<210> SEQ ID NO 35
<211> LENGTH: 30
<212> TYPE: DNA
<213> ORGANISM: Artificial
<220> FEATURE:
<223> OTHER INFORMATION: primer

<400> SEQUENCE: 35
agattcattt acttcaccgc tccatcatac 30

<210> SEQ ID NO 36
<211> LENGTH: 28
<212> TYPE: DNA
<213> ORGANISM: Artificial
<220> FEATURE:
<223> OTHER INFORMATION: primer

<400> SEQUENCE: 36
tcctggtaat aaaattccgt cgctgttg 28

<210> SEQ ID NO 37
<211> LENGTH: 70
<212> TYPE: DNA
<213> ORGANISM: Artificial
<220> FEATURE:
<223> OTHER INFORMATION: primer

<400> SEQUENCE: 37
ccgctcgaag tggccttgcg cgagaccctg gggcccgggt gtagatgtgt tggcagaaca 60
tatccatcgc 70

<210> SEQ ID NO 38
<211> LENGTH: 74
<212> TYPE: DNA
<213> ORGANISM: Artificial
<220> FEATURE:
<223> OTHER INFORMATION: primer

<400> SEQUENCE: 38
gtggaatata tgacatcaaa tacaaccagc agtcgtccat caggggatga ctatcaacag 60
gttgaactga tggc 74

<210> SEQ ID NO 39
<211> LENGTH: 74
<212> TYPE: DNA
<213> ORGANISM: Artificial
<220> FEATURE:

-continued

<223> OTHER INFORMATION: primer

<400> SEQUENCE: 39
ctgggagtaa aatgaaactg tttccttgct aaaggagtaa atcgtctcag ccctatgcta 60
ctccgtcgaa gttc 74

<210> SEQ ID NO 40
<211> LENGTH: 74
<212> TYPE: DNA
<213> ORGANISM: Artificial
<220> FEATURE:
<223> OTHER INFORMATION: primer

<400> SEQUENCE: 40
actactgcca gttgatgact gctggagcac ggagagccat cagcagtcag ctggcagttt 60
atggcgggcg tcct 74

<210> SEQ ID NO 41
<211> LENGTH: 28
<212> TYPE: DNA
<213> ORGANISM: Artificial
<220> FEATURE:
<223> OTHER INFORMATION: primer

<400> SEQUENCE: 41
gctccaaatg accacaagac taacaggc 28

<210> SEQ ID NO 42
<211> LENGTH: 28
<212> TYPE: DNA
<213> ORGANISM: Artificial
<220> FEATURE:
<223> OTHER INFORMATION: primer

<400> SEQUENCE: 42
gtgcacattc ctccaagtag gtatgaaa 28

<210> SEQ ID NO 43
<211> LENGTH: 25
<212> TYPE: DNA
<213> ORGANISM: Artificial
<220> FEATURE:
<223> OTHER INFORMATION: primer

<400> SEQUENCE: 43
agaagagaag aatgagcgtt acaat 25

<210> SEQ ID NO 44
<211> LENGTH: 25
<212> TYPE: DNA
<213> ORGANISM: Artificial
<220> FEATURE:
<223> OTHER INFORMATION: primer

<400> SEQUENCE: 44
ggattctaaa ttccttccta acaaa 25

<210> SEQ ID NO 45
<211> LENGTH: 25
<212> TYPE: DNA
<213> ORGANISM: Artificial
<220> FEATURE:
<223> OTHER INFORMATION: primer

<400> SEQUENCE: 45

-continued

```
atgaatacag tgtatttacc agtgt                                          25


<210> SEQ ID NO 46
<211> LENGTH: 25
<212> TYPE: DNA
<213> ORGANISM: Artificial
<220> FEATURE:
<223> OTHER INFORMATION: primer

<400> SEQUENCE: 46

gagctactac tgccagttga tgact                                          25


<210> SEQ ID NO 47
<211> LENGTH: 25
<212> TYPE: DNA
<213> ORGANISM: Artificial
<220> FEATURE:
<223> OTHER INFORMATION: primer

<400> SEQUENCE: 47

gtccttagaa gttgctgtaa tgtaa                                          25


<210> SEQ ID NO 48
<211> LENGTH: 25
<212> TYPE: DNA
<213> ORGANISM: Artificial
<220> FEATURE:
<223> OTHER INFORMATION: primer

<400> SEQUENCE: 48

tcacataatt atgattttaa caggc                                          25


<210> SEQ ID NO 49
<211> LENGTH: 25
<212> TYPE: DNA
<213> ORGANISM: Artificial
<220> FEATURE:
<223> OTHER INFORMATION: probe

<400> SEQUENCE: 49

cgggtgtaga tgtgttagga gagga                                          25


<210> SEQ ID NO 50
<211> LENGTH: 22
<212> TYPE: DNA
<213> ORGANISM: Artificial
<220> FEATURE:
<223> OTHER INFORMATION: probe

<400> SEQUENCE: 50

cctgcagctg aactgactgc tg                                             22


<210> SEQ ID NO 51
<211> LENGTH: 25
<212> TYPE: DNA
<213> ORGANISM: Artificial
<220> FEATURE:
<223> OTHER INFORMATION: probe

<400> SEQUENCE: 51

tgaatcgaac taacgtctgg acgtc                                          25


<210> SEQ ID NO 52
<211> LENGTH: 28
<212> TYPE: DNA
```

-continued

```
<213> ORGANISM: Artificial
<220> FEATURE:
<223> OTHER INFORMATION: primer

<400> SEQUENCE: 52

caccatggag actgctggag acaagaag                                      28


<210> SEQ ID NO 53
<211> LENGTH: 24
<212> TYPE: DNA
<213> ORGANISM: Artificial
<220> FEATURE:
<223> OTHER INFORMATION: primer

<400> SEQUENCE: 53

ttatccttcg aggctcttag tcaa                                          24


<210> SEQ ID NO 54
<211> LENGTH: 28
<212> TYPE: DNA
<213> ORGANISM: Artificial
<220> FEATURE:
<223> OTHER INFORMATION: primer

<400> SEQUENCE: 54

caccatgtca tacttcggcc tggagact                                      28


<210> SEQ ID NO 55
<211> LENGTH: 24
<212> TYPE: DNA
<213> ORGANISM: Artificial
<220> FEATURE:
<223> OTHER INFORMATION: primer

<400> SEQUENCE: 55

tgtctacggc ggcatatttg gggg                                          24
```